(12) United States Patent
Zhang et al.

(10) Patent No.: US 9,752,148 B2
(45) Date of Patent: Sep. 5, 2017

(54) EXTRACTION, PREPARATION, AND APPLICATION OF PLANT MICRO-RIBONUCLEIC ACID

(71) Applicant: MICROMEDMARK BIOTECH CO., LTD., Beijing (CN)

(72) Inventors: Chenyu Zhang, Beijing (CN); Junfeng Zhang, Beijing (CN); Ke Zeng, Beijing (CN); Lei Dong, Beijing (CN)

(73) Assignee: Micromedmark Biotech Co., Ltd., Beijing (CN)

( * ) Notice: Subject to any disclaimer, the term of this patent is extended or adjusted under 35 U.S.C. 154(b) by 0 days.

(21) Appl. No.: 14/422,117

(22) PCT Filed: Aug. 15, 2013

(86) PCT No.: PCT/CN2013/081583
§ 371 (c)(1),
(2) Date: Feb. 17, 2015

(87) PCT Pub. No.: WO2014/026627
PCT Pub. Date: Feb. 20, 2014

(65) Prior Publication Data
US 2015/0291962 A1      Oct. 15, 2015

(30) Foreign Application Priority Data
Aug. 15, 2012   (CN) .......................... 2012 1 0291378

(51) Int. Cl.
| | |
|---|---|
| *C12N 15/82* | (2006.01) |
| *A61K 36/355* | (2006.01) |
| *A61K 48/00* | (2006.01) |
| *C12N 15/113* | (2010.01) |
| *A61K 36/35* | (2006.01) |
| *A61K 31/713* | (2006.01) |
| *C12Q 1/68* | (2006.01) |
| *A61K 31/7105* | (2006.01) |

(52) U.S. Cl.
CPC ........ *C12N 15/1131* (2013.01); *A61K 31/713* (2013.01); *A61K 31/7105* (2013.01); *A61K 36/35* (2013.01); *A61K 36/355* (2013.01); *C12N 15/113* (2013.01); *C12N 15/8218* (2013.01); *C12Q 1/6895* (2013.01); *C12N 2310/113* (2013.01); *C12N 2310/141* (2013.01); *C12N 2320/30* (2013.01); *C12Q 2600/178* (2013.01)

(58) Field of Classification Search
USPC ....... 435/6.11, 6.12, 235.1, 375, 91.1, 91.31, 435/6.1; 506/2, 9; 514/44; 536/23.1, 536/24.5
See application file for complete search history.

(56) References Cited

U.S. PATENT DOCUMENTS

| | | | |
|---|---|---|---|
| 2009/0004668 A1* | 1/2009 | Chen ..................... | C12N 15/111 435/6.14 |
| 2014/0317781 A1* | 10/2014 | Maor ................... | C12N 15/113 800/286 |

FOREIGN PATENT DOCUMENTS

| | | |
|---|---|---|
| CN | 102697832 | 10/2012 |
| WO | 2010/130155 | 11/2010 |
| WO | 2011/067745 | 6/2011 |

OTHER PUBLICATIONS

J. Wei et al, Cotton Science, vol. 23, No. 5, pp. 433-439 (Mar. 23, 2011).*
Li et al, Biochem. Biophys. Res. Comm., vol. 388, pp. 272-277 (2009).*
Li et al , Biochem. Biophys. Res. Comm., vol. 388, pp. 272-277: BBRC Supplemental data (2009).*
Li et al , Biochem. Biophys. Res. Comm., vol. 388, pp. 272-277: BBRC Accession No. for miR 2911 (2009).*
Ko et al, J. Ethnopharmacol., vol. 107, pp. 205-210 (2006).*
Zhang et al, Cell Res., vol. 22, pp. 107-126 (s012, Publ. online Sep. 20, 2011).*
International search report for application No. PCT/CN2013/081583, dated Nov. 14, 2013 (13 pages).
B. Li et al., "Identification of microRNAs and their targets from *Populus euphratica*," Biochemical and Biophysical Research Communications, vol. 388 (2009), p. 272-277.
J. Wei et al., "Analysis of microRNAs at Cotton Microsporocyte Stage," Cotton Science, vol. 23, No. 5 (2011), p. 433-439.
L. Zhang et al., "Exogenous plant MIR168a specifically targets mammalian LDLRAP1: evidence of cross-kingdom regulation by microRNA," Cell Research, vol. 22 (2012), p. 107-126.

* cited by examiner

*Primary Examiner* — Jane Zara
(74) *Attorney, Agent, or Firm* — Hamre, Schumann, Mueller & Larson, P.C.

(57) ABSTRACT

An isolated plant-functional microRNA or an extract containing said plant-functional microRNA, a preparation method therefor, and an application thereof are provided. The plant-functional microRNA originates from the endogenous microRNA of a plant, is present in a water-soluble and/or fat-soluble extract of said plant, and is capable of regulating non-plant target-genes.

11 Claims, 11 Drawing Sheets

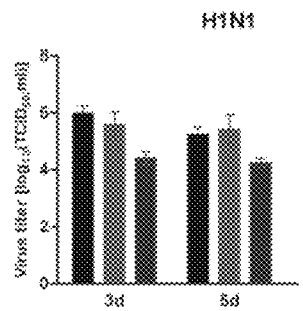
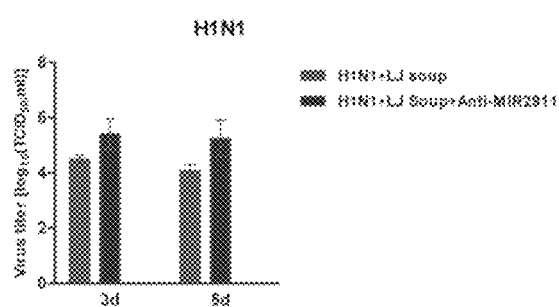
Figure 21     Figure 22
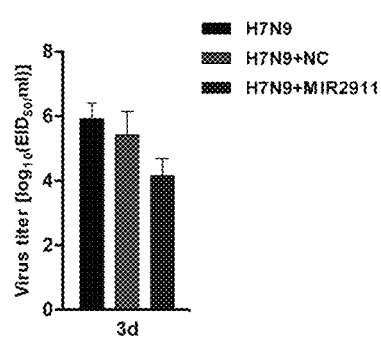
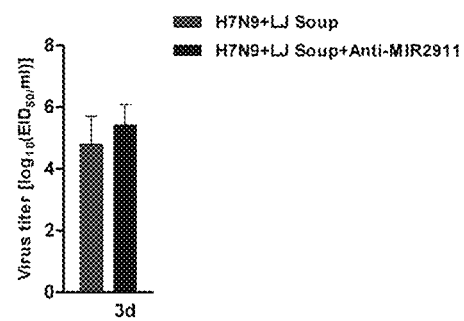
Figure 23     Figure 24
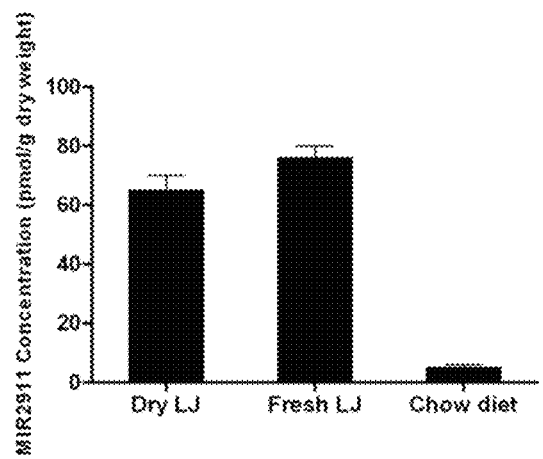
Figure 25

SEQUENCE LISTING

```
<160> NUMBER OF SEQ ID NOS: 102

<210> SEQ ID NO 1
<211> LENGTH: 21
<212> TYPE: RNA
<213> ORGANISM: Lonicera japonica

<400> SEQUENCE: 1
uugacagaag auagagagca c                                        21

<210> SEQ ID NO 2
<211> LENGTH: 21
<212> TYPE: RNA
```

-continued

```
<213> ORGANISM: Lonicera japonica

<400> SEQUENCE: 2
ucggaccagg cuucauuccc c                                        21

<210> SEQ ID NO 3
<211> LENGTH: 21
<212> TYPE: RNA
<213> ORGANISM: Lonicera japonica

<400> SEQUENCE: 3
uuccacagcu uucuugaacu g                                        21

<210> SEQ ID NO 4
<211> LENGTH: 21
<212> TYPE: RNA
<213> ORGANISM: Lonicera japonica

<400> SEQUENCE: 4
ucggaccagg cuucauuccc c                                        21

<210> SEQ ID NO 5
<211> LENGTH: 21
<212> TYPE: RNA
<213> ORGANISM: Lonicera japonica

<400> SEQUENCE: 5
ucgcuuggug caggucggga a                                        21

<210> SEQ ID NO 6
<211> LENGTH: 20
<212> TYPE: RNA
<213> ORGANISM: Lonicera japonica

<400> SEQUENCE: 6
ugcucaaaua ccacucuccu                                          20

<210> SEQ ID NO 7
<211> LENGTH: 21
<212> TYPE: RNA
<213> ORGANISM: Lonicera japonica

<400> SEQUENCE: 7
uaguuggugg agcgauuugu c                                        21

<210> SEQ ID NO 8
<211> LENGTH: 20
<212> TYPE: RNA
<213> ORGANISM: Lonicera japonica

<400> SEQUENCE: 8
ggccggggga cgggcuggga                                          20

<210> SEQ ID NO 9
<211> LENGTH: 20
<212> TYPE: RNA
<213> ORGANISM: Lonicera japonica

<400> SEQUENCE: 9
cccgucuagc ucaguuggua                                          20

<210> SEQ ID NO 10
<211> LENGTH: 22
```

-continued

<212> TYPE: RNA
<213> ORGANISM: Lonicera japonica

<400> SEQUENCE: 10 ugggacucg aagacgauca ua                                          22

<210> SEQ ID NO 11
<211> LENGTH: 22
<212> TYPE: RNA
<213> ORGANISM: Lonicera japonica

<400> SEQUENCE: 11
aaucccuuau auuaugggac gg                                         22

<210> SEQ ID NO 12
<211> LENGTH: 21
<212> TYPE: RNA
<213> ORGANISM: Lonicera japonica

<400> SEQUENCE: 12
auugguuuga agggagcucc a                                          21

<210> SEQ ID NO 13
<211> LENGTH: 21
<212> TYPE: RNA
<213> ORGANISM: Lonicera japonica

<400> SEQUENCE: 13
auuggauuga agggagcucc a                                          21

<210> SEQ ID NO 14
<211> LENGTH: 20
<212> TYPE: RNA
<213> ORGANISM: Lonicera japonica

<400> SEQUENCE: 14
ugacagaaga gagagagcac                                            20

<210> SEQ ID NO 15
<211> LENGTH: 21
<212> TYPE: RNA
<213> ORGANISM: Lonicera japonica

<400> SEQUENCE: 15
cucaggagag augacaccga c                                          21

<210> SEQ ID NO 16
<211> LENGTH: 21
<212> TYPE: RNA
<213> ORGANISM: Lonicera japonica

<400> SEQUENCE: 16
ucggaccagg cuucauuccc c                                          21

<210> SEQ ID NO 17
<211> LENGTH: 21
<212> TYPE: RNA
<213> ORGANISM: Lonicera japonica

<400> SEQUENCE: 17
ugaagcugcc agcaugaucu a                                          21

<210> SEQ ID NO 18

```
<211> LENGTH: 21
<212> TYPE: RNA
<213> ORGANISM: Lonicera japonica

<400> SEQUENCE: 18
uuccacagcu uucuugaacu u                                              21

<210> SEQ ID NO 19
<211> LENGTH: 21
<212> TYPE: RNA
<213> ORGANISM: Lonicera japonica

<400> SEQUENCE: 19
ugacagaaga gagugagcac a                                              21

<210> SEQ ID NO 20
<211> LENGTH: 21
<212> TYPE: RNA
<213> ORGANISM: Lonicera japonica

<400> SEQUENCE: 20
uagccaagga ugacuugccu g                                              21

<210> SEQ ID NO 21
<211> LENGTH: 21
<212> TYPE: RNA
<213> ORGANISM: Lonicera japonica

<400> SEQUENCE: 21
uaagcugcca gcaugaucuu g                                              21

<210> SEQ ID NO 22
<211> LENGTH: 21
<212> TYPE: RNA
<213> ORGANISM: Lonicera japonica

<400> SEQUENCE: 22
ugccuggcuc ccuguaugcc a                                              21

<210> SEQ ID NO 23
<211> LENGTH: 21
<212> TYPE: RNA
<213> ORGANISM: Lonicera japonica

<400> SEQUENCE: 23
ugccaaagga gaauugcccu g                                              21

<210> SEQ ID NO 24
<211> LENGTH: 20
<212> TYPE: RNA
<213> ORGANISM: Lonicera japonica

<400> SEQUENCE: 24
ugacagaaga gagugagcac                                                20

<210> SEQ ID NO 25
<211> LENGTH: 21
<212> TYPE: RNA
<213> ORGANISM: Lonicera japonica

<400> SEQUENCE: 25
ugccuggcuc ccuguaugcc a                                              21
```

-continued

<210> SEQ ID NO 26
<211> LENGTH: 21
<212> TYPE: RNA
<213> ORGANISM: Lonicera japonica

<400> SEQUENCE: 26
ugagccaagg augacuugcc g                                              21

<210> SEQ ID NO 27
<211> LENGTH: 21
<212> TYPE: RNA
<213> ORGANISM: Lonicera japonica

<400> SEQUENCE: 27
ucggaccagg cuucaauccc u                                              21

<210> SEQ ID NO 28
<211> LENGTH: 21
<212> TYPE: RNA
<213> ORGANISM: Lonicera japonica

<400> SEQUENCE: 28
uuuggauuga agggagcucu g                                              21

<210> SEQ ID NO 29
<211> LENGTH: 21
<212> TYPE: RNA
<213> ORGANISM: Lonicera japonica

<400> SEQUENCE: 29
ucggaccagg cuucauuccc c                                              21

<210> SEQ ID NO 30
<211> LENGTH: 21
<212> TYPE: RNA
<213> ORGANISM: Lonicera japonica

<400> SEQUENCE: 30
uuuggauuga agggagcucu g                                              21

<210> SEQ ID NO 31
<211> LENGTH: 21
<212> TYPE: RNA
<213> ORGANISM: Lonicera japonica

<400> SEQUENCE: 31
ucggaucagg cuucauuccu c                                              21

<210> SEQ ID NO 32
<211> LENGTH: 21
<212> TYPE: RNA
<213> ORGANISM: Lonicera japonica

<400> SEQUENCE: 32
ugaagcugcc agcaugaucu g                                              21

<210> SEQ ID NO 33
<211> LENGTH: 21
<212> TYPE: RNA
<213> ORGANISM: Lonicera japonica

<400> SEQUENCE: 33
cagccaagga ugacuugccg g                                              21

```
<210> SEQ ID NO 34
<211> LENGTH: 21
<212> TYPE: RNA
<213> ORGANISM: Lonicera japonica

<400> SEQUENCE: 34
uggagaagca gggcacgugc a                                              21

<210> SEQ ID NO 35
<211> LENGTH: 21
<212> TYPE: RNA
<213> ORGANISM: Lonicera japonica

<400> SEQUENCE: 35
ugaagcugcc agcaugaucu g                                              21

<210> SEQ ID NO 36
<211> LENGTH: 21
<212> TYPE: RNA
<213> ORGANISM: Lonicera japonica

<400> SEQUENCE: 36
ugaagcugcc agcaugaucu g                                              21

<210> SEQ ID NO 37
<211> LENGTH: 21
<212> TYPE: RNA
<213> ORGANISM: Lonicera japonica

<400> SEQUENCE: 37
ugccuggcuc ccuguaugcc a                                              21

<210> SEQ ID NO 38
<211> LENGTH: 21
<212> TYPE: RNA
<213> ORGANISM: Lonicera japonica

<400> SEQUENCE: 38
ugccaaagga gauuugcccg g                                              21

<210> SEQ ID NO 39
<211> LENGTH: 21
<212> TYPE: RNA
<213> ORGANISM: Lonicera japonica

<400> SEQUENCE: 39
ugccaaagga gauuugcccg g                                              21

<210> SEQ ID NO 40
<211> LENGTH: 21
<212> TYPE: RNA
<213> ORGANISM: Lonicera japonica

<400> SEQUENCE: 40
agaagagaga gaguacagcu u                                              21

<210> SEQ ID NO 41
<211> LENGTH: 21
<212> TYPE: RNA
<213> ORGANISM: Lonicera japonica

<400> SEQUENCE: 41
uggagaagca ggacacguga g                                              21
```

```
<210> SEQ ID NO 42
<211> LENGTH: 21
<212> TYPE: RNA
<213> ORGANISM: Lonicera japonica

<400> SEQUENCE: 42
ucggaccagg cuucauuccc c                                              21

<210> SEQ ID NO 43
<211> LENGTH: 21
<212> TYPE: RNA
<213> ORGANISM: Lonicera japonica

<400> SEQUENCE: 43
ucggaccagg cuucauuccc c                                              21

<210> SEQ ID NO 44
<211> LENGTH: 21
<212> TYPE: RNA
<213> ORGANISM: Lonicera japonica

<400> SEQUENCE: 44
uggagaagca gggcacgugc a                                              21

<210> SEQ ID NO 45
<211> LENGTH: 20
<212> TYPE: RNA
<213> ORGANISM: Lonicera japonica

<400> SEQUENCE: 45
ugacagaaga gagugagcac                                                20

<210> SEQ ID NO 46
<211> LENGTH: 21
<212> TYPE: RNA
<213> ORGANISM: Lonicera japonica

<400> SEQUENCE: 46
uggagaagca gggcacgugc a                                              21

<210> SEQ ID NO 47
<211> LENGTH: 21
<212> TYPE: RNA
<213> ORGANISM: Lonicera japonica

<400> SEQUENCE: 47
uagccaagga ugacuugccu g                                              21

<210> SEQ ID NO 48
<211> LENGTH: 21
<212> TYPE: RNA
<213> ORGANISM: Lonicera japonica

<400> SEQUENCE: 48
ucggaccagg cuucauuccc u                                              21

<210> SEQ ID NO 49
<211> LENGTH: 21
<212> TYPE: RNA
<213> ORGANISM: Lonicera japonica

<400> SEQUENCE: 49
```
uggagaagca gggcacgugc u     21

<210> SEQ ID NO 50
<211> LENGTH: 20
<212> TYPE: RNA
<213> ORGANISM: Lonicera japonica

<400> SEQUENCE: 50
ugacagaaga gagggagcac     20

<210> SEQ ID NO 51
<211> LENGTH: 21
<212> TYPE: RNA
<213> ORGANISM: Lonicera japonica

<400> SEQUENCE: 51
ucggaccagg cuucauuccc c     21

<210> SEQ ID NO 52
<211> LENGTH: 21
<212> TYPE: RNA
<213> ORGANISM: Lonicera japonica

<400> SEQUENCE: 52
ucggaccagg cuucauuccc c     21

<210> SEQ ID NO 53
<211> LENGTH: 21
<212> TYPE: RNA
<213> ORGANISM: Lonicera japonica

<400> SEQUENCE: 53
ugccuggcuc ccuguaugcc a     21

<210> SEQ ID NO 54
<211> LENGTH: 21
<212> TYPE: RNA
<213> ORGANISM: Lonicera japonica

<400> SEQUENCE: 54
ucggaccagg cuucauuccc c     21

<210> SEQ ID NO 55
<211> LENGTH: 21
<212> TYPE: RNA
<213> ORGANISM: Lonicera japonica

<400> SEQUENCE: 55
cuuggauuga agggagcucc u     21

<210> SEQ ID NO 56
<211> LENGTH: 22
<212> TYPE: RNA
<213> ORGANISM: Lonicera japonica

<400> SEQUENCE: 56
aaucccuuau auuaugggac gg     22

<210> SEQ ID NO 57
<211> LENGTH: 21
<212> TYPE: RNA
<213> ORGANISM: Lonicera japonica

<400> SEQUENCE: 57

```
agaaucuuga ugaugcugca u                                              21

<210> SEQ ID NO 58
<211> LENGTH: 20
<212> TYPE: RNA
<213> ORGANISM: Lonicera japonica

<400> SEQUENCE: 58
ugacagaaga gagugagcac                                                20

<210> SEQ ID NO 59
<211> LENGTH: 21
<212> TYPE: RNA
<213> ORGANISM: Lonicera japonica

<400> SEQUENCE: 59
ugccaaagga gauuugccca g                                              21

<210> SEQ ID NO 60
<211> LENGTH: 21
<212> TYPE: RNA
<213> ORGANISM: Lonicera japonica

<400> SEQUENCE: 60
cagccaagga ugacuugccg g                                              21

<210> SEQ ID NO 61
<211> LENGTH: 21
<212> TYPE: RNA
<213> ORGANISM: Lonicera japonica

<400> SEQUENCE: 61
ugccaaagga gauuugccca g                                              21

<210> SEQ ID NO 62
<211> LENGTH: 21
<212> TYPE: RNA
<213> ORGANISM: Lonicera japonica

<400> SEQUENCE: 62
ugaagcugcc agcaugaucu a                                              21

<210> SEQ ID NO 63
<211> LENGTH: 20
<212> TYPE: RNA
<213> ORGANISM: Lonicera japonica

<400> SEQUENCE: 63
uuggcauucu guccaccucc                                                20

<210> SEQ ID NO 64
<211> LENGTH: 20
<212> TYPE: RNA
<213> ORGANISM: Lonicera japonica

<400> SEQUENCE: 64
ugacagaaga gagugagcac                                                20

<210> SEQ ID NO 65
<211> LENGTH: 21
<212> TYPE: RNA
<213> ORGANISM: Lonicera japonica
```

```
<400> SEQUENCE: 65
ucggaucagg cuucauuccu c                                              21

<210> SEQ ID NO 66
<211> LENGTH: 21
<212> TYPE: RNA
<213> ORGANISM: Lonicera japonica

<400> SEQUENCE: 66
ugaagcugcc agcaugaucu g                                              21

<210> SEQ ID NO 67
<211> LENGTH: 21
<212> TYPE: RNA
<213> ORGANISM: Lonicera japonica

<400> SEQUENCE: 67
agcugccgaa ucauccauuc a                                              21

<210> SEQ ID NO 68
<211> LENGTH: 20
<212> TYPE: RNA
<213> ORGANISM: Lonicera japonica

<400> SEQUENCE: 68
ugacagaaga gagugagcac                                                20

<210> SEQ ID NO 69
<211> LENGTH: 21
<212> TYPE: RNA
<213> ORGANISM: Lonicera japonica

<400> SEQUENCE: 69
ucggaccagg cuucauuccc c                                              21

<210> SEQ ID NO 70
<211> LENGTH: 21
<212> TYPE: RNA
<213> ORGANISM: Lonicera japonica

<400> SEQUENCE: 70
ugccaaagga gaauugcccu g                                              21

<210> SEQ ID NO 71
<211> LENGTH: 21
<212> TYPE: RNA
<213> ORGANISM: Lonicera japonica

<400> SEQUENCE: 71
ugccuggcuc ccuguaugcc a                                              21

<210> SEQ ID NO 72
<211> LENGTH: 21
<212> TYPE: RNA
<213> ORGANISM: Lonicera japonica

<400> SEQUENCE: 72
uuuggauuga agggagcucu g                                              21

<210> SEQ ID NO 73
<211> LENGTH: 20
<212> TYPE: RNA
<213> ORGANISM: Lonicera japonica
```

<400> SEQUENCE: 73
ugacagaaga gagugagcac                                                    20

<210> SEQ ID NO 74
<211> LENGTH: 20
<212> TYPE: RNA
<213> ORGANISM: Lonicera japonica

<400> SEQUENCE: 74
uuggacugaa gggugcuccc                                                    20

<210> SEQ ID NO 75
<211> LENGTH: 21
<212> TYPE: RNA
<213> ORGANISM: Lonicera japonica

<400> SEQUENCE: 75
uagccaagaa ugacuugccu a                                                  21

<210> SEQ ID NO 76
<211> LENGTH: 21
<212> TYPE: RNA
<213> ORGANISM: Lonicera japonica

<400> SEQUENCE: 76
ugaagcugcc agcaugaucu g                                                  21

<210> SEQ ID NO 77
<211> LENGTH: 20
<212> TYPE: RNA
<213> ORGANISM: Lonicera japonica

<400> SEQUENCE: 77
ugacagaaga gagugagcac                                                    20

<210> SEQ ID NO 78
<211> LENGTH: 21
<212> TYPE: RNA
<213> ORGANISM: Lonicera japonica

<400> SEQUENCE: 78
ugaagcugcc agcaugaucu g                                                  21

<210> SEQ ID NO 79
<211> LENGTH: 21
<212> TYPE: RNA
<213> ORGANISM: Lonicera japonica

<400> SEQUENCE: 79
cagccaagga ugacuugccg a                                                  21

<210> SEQ ID NO 80
<211> LENGTH: 21
<212> TYPE: RNA
<213> ORGANISM: Lonicera japonica

<400> SEQUENCE: 80
agaaucuuga ugaugcugca u                                                  21

<210> SEQ ID NO 81
<211> LENGTH: 22
<212> TYPE: RNA

<213> ORGANISM: Lonicera japonica

<400> SEQUENCE: 81
aaucccuuau auuaugggac gg                                    22

<210> SEQ ID NO 82
<211> LENGTH: 21
<212> TYPE: RNA
<213> ORGANISM: Lonicera japonica

<400> SEQUENCE: 82
uggagaagca gggcacgugc u                                     21

<210> SEQ ID NO 83
<211> LENGTH: 21
<212> TYPE: RNA
<213> ORGANISM: Lonicera japonica

<400> SEQUENCE: 83
ugaagcugcc agcaugaucu g                                     21

<210> SEQ ID NO 84
<211> LENGTH: 21
<212> TYPE: RNA
<213> ORGANISM: Lonicera japonica

<400> SEQUENCE: 84
uuccacagcu uucuugaacu g                                     21

<210> SEQ ID NO 85
<211> LENGTH: 23
<212> TYPE: RNA
<213> ORGANISM: Lonicera japonica

<400> SEQUENCE: 85
uaugguggug acggugacg gag                                    23

<210> SEQ ID NO 86
<211> LENGTH: 28
<212> TYPE: DNA
<213> ORGANISM: Artificial sequence
<220> FEATURE:
<223> OTHER INFORMATION: oligonucleotide

<400> SEQUENCE: 86
acactccagc tgggggccgg gggacggg                              28

<210> SEQ ID NO 87
<211> LENGTH: 44
<212> TYPE: DNA
<213> ORGANISM: Artificial sequence
<220> FEATURE:
<223> OTHER INFORMATION: oligonucleotide

<400> SEQUENCE: 87
ctcaactggt gtcgtggagt cggcaattca gttgagtccc agcc            44

<210> SEQ ID NO 88
<211> LENGTH: 20
<212> TYPE: DNA
<213> ORGANISM: Artificial sequence
<220> FEATURE:
<223> OTHER INFORMATION: oligonucleotide

<400> SEQUENCE: 88
tcccagcccg tcccccggcc					20

<210> SEQ ID NO 89
<211> LENGTH: 21
<212> TYPE: DNA
<213> ORGANISM: Artificial sequence
<220> FEATURE:
<223> OTHER INFORMATION: oligonucleotide

<400> SEQUENCE: 89
caaagacttc tcatcggttg c					21

<210> SEQ ID NO 90
<211> LENGTH: 20
<212> TYPE: DNA
<213> ORGANISM: Artificial sequence
<220> FEATURE:
<223> OTHER INFORMATION: oligonucleotide

<400> SEQUENCE: 90
aatgcaacac tcggttcaca					20

<210> SEQ ID NO 91
<211> LENGTH: 20
<212> TYPE: DNA
<213> ORGANISM: Artificial sequence
<220> FEATURE:
<223> OTHER INFORMATION: oligonucleotide

<400> SEQUENCE: 91
tcaggccccc tcaaagccga					20

<210> SEQ ID NO 92
<211> LENGTH: 20
<212> TYPE: DNA
<213> ORGANISM: Artificial sequence
<220> FEATURE:
<223> OTHER INFORMATION: oligonucleotide

<400> SEQUENCE: 92
cccaaagtga gggatcaaga					20

<210> SEQ ID NO 93
<211> LENGTH: 20
<212> TYPE: DNA
<213> ORGANISM: Artificial sequence
<220> FEATURE:
<223> OTHER INFORMATION: oligonucleotide

<400> SEQUENCE: 93
cccttgggtg tctgacaagt					20

<210> SEQ ID NO 94
<211> LENGTH: 24
<212> TYPE: DNA
<213> ORGANISM: Artificial sequence
<220> FEATURE:
<223> OTHER INFORMATION: oligonucleotide

<400> SEQUENCE: 94
tcaacagtgg cgagttccct agca				24

<210> SEQ ID NO 95
<211> LENGTH: 1107
<212> TYPE: DNA

<213> ORGANISM: Human adenovirus C
<220> FEATURE:
<221> NAME/KEY: misc_feature
<223> OTHER INFORMATION: ADV1
<220> FEATURE:
<221> NAME/KEY: misc_feature
<222> LOCATION: (899)..(923)
<223> OTHER INFORMATION: targeting position

<400> SEQUENCE: 95

```
atgtccaagc gcaaaatcaa agaagagatg ctccaggtca tcgcgccgga gatctatggc        60
cccccgaaga aggaagagca ggattacaag ccccgaaagc taaagcgggt caaaaagaaa       120
aagaaagatg atgatgatga acttgacgac gaggtgaaac tgctgcacgc taccgcgccc       180
aggcgacggg tacagtggaa aggtcgacgc gtaaaacgtg ttttgcgacc cggcaccacc       240
gtagtcttta cgcccggtga gcgctccacc cgcacctaca agcgcgtgta tgatgaggtg       300
tacggcgacg aggacctgct tgagcaggcc aacgagcgcc tcggggagtt tgcctacgga       360
aagcggcata aggacatgct ggcgttgccg ctggacgagg caacccaac acctagccta        420
aagcccgtaa cactgcagca ggtgctgccc gcgcttgcac cgtccgaaga aaagcgcggc       480
ctaaagcgcg agtctggtga cttggcaccc accgtgcagc tgatggtacc caagcgccag       540
cgactggaag atgtcttgga aaaaatgacc gtggaacctg gctggagcc cgaggtccgc        600
gtgcggccaa tcaagcaggt ggcgccggga ctgggcgtgc agaccgtgga cgttcagata       660
cccactacca gtagcaccag tattgccacc gccacagagg gcatggagac acaaacgtcc       720
ccggttgcct cagcggtggc ggatgccgcg gtgcaggcgg tcgctgcggc cgcgtccaag       780
acctctacgg aggtgcaaac ggacccgtgg atgtttcgcg tttcagcccc ccggcgcccg       840
cgccgttcga ggaagtacgg cgccgccagc gcgctactgc ccgaatatgc cctacatcct       900
tccattgcgc ctaccccgg ctatcgtggc tacacctacc gccccagaag acgagcaact       960
acccgacgcc gaaccaccac tggaacccgc cgccgccgtc gccgtcgcca gcccgtgctg      1020
gccccgattt ccgtgcgcag ggtggctcgc gaaggaggca ggaccctggt gctgccaaca      1080
gcgcgctacc accccagcat cgtttaa                                          1107
```

<210> SEQ ID NO 96
<211> LENGTH: 453
<212> TYPE: DNA
<213> ORGANISM: Human adenovirus C
<220> FEATURE:
<221> NAME/KEY: misc_feature
<223> OTHER INFORMATION: ADV2
<220> FEATURE:
<221> NAME/KEY: misc_feature
<222> LOCATION: (382)..(401)
<223> OTHER INFORMATION: targeting position

<400> SEQUENCE: 96

```
atgactacgt ccggcgttcc atttggcatg acactacgac caacacgatc tcggttgtct        60
cggcgcactc cgtacagtag ggatcgtcta cctccttttg agacagaaac ccgcgctacc       120
atactggagg atcatccgct gctgcccgaa tgtaacactt tgacaatgca caacgcgtgg       180
acttctcctt cgccgcccgt taagcaaccg caagttggac agcagcctgt ggctcagcag       240
ctggacagcg acatgaactt aagtgagctg cccggggagt ttattaatat cactgatgag       300
cgtttggctc gacaggaaac cgtgtggaat ataaccccta agaatatgtc tgttacccat       360
gatatgatgc ttttttaaggc cagccgggga gaaaggactg tgtactctgt gtgttgggag      420
ggaggtggca ggttgaatac tagggttctg tga                                    453
```

<210> SEQ ID NO 97
<211> LENGTH: 6672
<212> TYPE: DNA
<213> ORGANISM: human parainfluenza virus type 1
<220> FEATURE:
<221> NAME/KEY: misc_feature
<222> LOCATION: (180)..(197)
<223> OTHER INFORMATION: targeting position

<400> SEQUENCE: 97

```
atggataaac aggagtcaac tcagaattcc tcagacatct tatatccaga atgtcacttg     60
aactctccga ttgtaaaaag caagattgct caacttcacg ttttgctaga tatcaatcaa    120
ccctatgatt taaaagataa cagtataata aatatcacca aatacaaaat cagaaatgga    180
ggtttatcgc cccggcagat caaaatcaga tcgctaggca aaatccttaa acaagaaatt    240
aaggatattg atcgttacac ttttgaacct tatccgattt tctcattaga gttactcaga    300
ctggatatcc cagaaatatg tgacaaaata agatccattt tttcagtctc tgatagatta    360
ataagagaac tatcatctgg atttcaagaa ttgtggttaa atattcttag acaattaggc    420
tgtgttgaag ggaaagaggg atttgactca ttaaaggatg tagatatcat cccagatata    480
actgataaat ataataaaaa cacatggtat cgcccattct taacatggtt tagcatcaaa    540
tatgatatga gatggatgca aaagaataag tcggggaacc atttagatgt ctcaaattct    600
cacaattttc ttgactgtaa atcatatatt ttgattatat atagagattt agtgataaata    660
ataaataaat taaaattaac cggttatgtc cttacacctg aattagtatt aatgtattgt    720
gatgttgtcg aaggaagatg gaatatgtct tcagctggac gactcgataa aaggtcatca    780
aaaataacat gtaaggggga agaattatgg gagcttatcg actctttatt tcccaatctt    840
ggtgaggatg tatataatat tatatcacta ctagaacctt tatcacttgc tttaatacag    900
ttggatgacc ctgtaactaa tttaaaagga gctttcatga gacatgtttt gactgagcta    960
catacaattt taataaaaga taatatatac acagattcag aagcagacag cataatggaa   1020
tcattgataa agattttcag agagacatca attgatgaaa aagcagaaat tttctccttt   1080
tttagaacgt ttggacatcc tagcttagaa gcaataactg ctgccgataa agtaaggaca   1140
catatgtatt cctccaaaaa aatcatacta aagacactat atgagtgtca tgcaatcttc   1200
tgtgcaatta taataaacgg atatagagaa agacacggtg gtcaatggcc gccatgcgaa   1260
ttccccaatc atgtatgtct tgaactcaag aatgcacaag gatccaactc tgcaatttcg   1320
tatgaatgtg ccgtagacaa ttatagtagt tttataggat ttaaattttt aaaatttatt   1380
gagcctcaat tagatgaaga tttgacaatt tatatgaagg ataaggctct atcacctagg   1440
aaagcagcat gggattcagt atatcccgac agtaatttat attacaaagt ccctgaatca   1500
gaagagactc gtaggttaat cgaggttttt ataaatgata ataattttaa ccctgcggat   1560
attattaatt atgtagagtc aggagaatgg ttaaatgacg atagcttcaa catatcttac   1620
agtctcaaag aaaaagaaat taaacaagag ggtcgactct ttgccaagat gacatataag   1680
atgagagcag tccaggtatt agcagaaaca ctactagcaa aaggagtagg tgagttattc   1740
agtgaaaatg ggatggtaaa gggagaaatt gacctactaa agagactgac tacattatct   1800
gtctcaggtg ttccaagatc caactcagtt tacaataatc ccatattaca tgagaaattg   1860
atcaaaaata tgaataagtg caattcaaat gggtattggg atgaaagaaa gaaatctaaa   1920
aatgaattca aagctgcaga ctcatcaacc gaggggtatg agactctgag ctgtttttta   1980
```

```
accaccgatt tgaaaaaata ctgtctcaac tggagatttg aaagtacagc gttgttcggt    2040
caaagatgta atgagatatt cgggtttaaa actttcttta actggatgca ccctattcta    2100
gaaaaaagta caatttatgt aggagatcct tactgtccag tacctgatag aatgcacaaa    2160
gaactccaag atcatgatga taccggaatc tttatccata atccaagagg gggaatagag    2220
ggttattgcc agaaattatg gacactaatc tctattagtg caatccatct tgcagctgtt    2280
aaagttggtg tcagagtgtc agcaatggta caaggagaca atcaagctat agcagtgaca    2340
tccagagttc ctgtcacaca aacctataag caaaaaaaga ctcacgtcta tgaagaaatc    2400
acaagatatt tcggtgcctt gagagaagtt atgtttgata ttggacatga attaaaatta    2460
aatgagacca ttataagtag caaaatgttt gtatacagca acggatata ttatgatggg     2520 aaaatcctcc cacagtgcct caaagcttta acaagatgtg tattttggtc agagactctt    2580
gtagatgaaa acaggtcagc atgctcaaac attgcaacat ctatagccaa agctattgag    2640
aatggatatt caccatatctt aggctattgt attgctcttt ttaaaacttg ccaacaggta    2700
tgtatatcat taggaatgac cattaatcct actattacgt caactatcaa agatcaatat    2760
tttaaaggga aaaattggtt aagatgtgca atattgatcc cagctaacat aggagggttc    2820
aactatatgt ctacagctag atgttttgtc agaaatatag gtgatccagc agttgcagct    2880
ctagcagact taaagagatt catcaaagca ggtctgttag ataaacaggt attatatcgt    2940
gtgatgaatc aagaaccagg agactcaagc ttcttagatt gggcatcaga cccttattca    3000
tgcaatctcc cacactcaca aagtataaca actataatca aaaatgtaac agctagatca    3060
gtattgcagg aatcacctaa tcctctccta tcaggtctct tttcagaatc aagtagtgaa    3120
gaagatctca acttagcatc atttttgatg gataggaaag ccatattgcc cagagtagct    3180
cacgagatct tagataactc acttacaggt gtaagagaag ctatagccgg gatgcttgat    3240
acaacgaaat ctctagtaag agctagtgtc aggagaggag gattatcata tagtatctta    3300
agaagactta taaattatga tctattacaa tatgagacct taacaaggac actcagaaaa    3360
ccggttaagg ataatataga atatgagtat atgtgttcag tagaattggc aataggattg    3420
aggcaaaaaa tgtggttttca tctaacttat ggaagaccaa tccacggttt agaaactcca    3480
gacccgttag aattattaag aggatcattt attgaaggct cagaaatatg taaattttgt    3540
agatcagaag ggaataaccc tatgtatact tggttctatc ttcctgacaa catcgactta    3600
gatacactta gcaatggaag tcctgccata cgtatccctt attttggttc tgctactgat    3660
gaaagatcag aggctcaact aggttatgtt aagaacttaa gcaagccggc aaaagcagca    3720
ataagaatcg caatggttta cacttgggct tatggaactg atgaaatatc atggatggaa    3780
gcagcactta tagctcaaac cagggctaac ttaagtttag agaatttgaa gttactcacc    3840
cctgtatcga cttctacaaa tttgtcccac agattgagag atactgctac acagatgaaa    3900
ttttcaagtg ctactttagt tcgagcgagt cgatttatta ccatatctaa tgataatatg    3960
gcattaaaag aggcaggaga gtctaaagat actaatttag tttatcaaca aattatgtta    4020
accggattga gcttatttga attcaatatg aggtataaac aaggatcatt atctaaacct    4080
atgatattac acttacattt gaataataaa tgctgtatca tagaatctcc tcaagaattg    4140
aatattcctc ctagatctac attggactta gagatcactc aggaaaataa caagttaatc    4200
tatgatcctg atcctctcaa ggacatagat ctagagttat ttagtaaggt tagggatgta    4260
gtacacacaa ttgatatgaa ttattggtct gatgatgaaa taattagagc aactagtata    4320
tgtacagcta tgactattgc agacacaatg tctcaattag atagagacaa tcttaaagaa    4380
```

```
atgatagcac tgataaatga tgatgatata aatagtttaa tcaccgaatt tatggttatt      4440 gatatacect tattttgttc cactttcggg ggtattctaa tcaatcaatt tgcatattca      4500
ctttacgggt taaacgtcag agggagggat gaaatatggg gatatgtgat acgcataatt      4560
aaagacacat cacatgcagt cctaaaagta ctgtccaatg cattatcaca tcctaaaata      4620
ttcaaacgat tctgggatgc aggagttgta gagcctgttt atggacctaa cttgtccaat      4680
caagacaaga tactgttagc catttcagta tgtgaatact ctgttgacct cttcatgcgt      4740
gattggcaag agggcatacc gcttgaaata tttatttgtg ataacgaccc aaatatagca      4800
gaaatgagaa aactttcatt tttagctaga catctagcat acttgtgtag tttggcagag      4860
atagctaaag agggaccaaa attggaatct atgacatctc tcgaacgact cgaatcattg      4920
aaagagtatc tagaacttac ttttttagac gatcctatat aagatatag tcaattgaca      4980 ggcttagtta ttaagatatt cccttcaacg ttaacttaca tcaggaaatc ttcaattaag      5040
gtgttgagag taagaggtat agggatacca gaagtcttag aggactggga tcctgatgcc      5100
gatagtatgc tactagataa tataactgct gaggttcaac acaatatacc tttaaagaag      5160
aacgaaagaa ctcccttctg ggggttaagg gtatcaaaat cacaagttct gcgacttaga      5220
ggttatgaag agataaaaag ggaagaaaga ggaagatcag gtgtaggatt aactctacct      5280
tttgatgggc gatatttatc acaccaattg agacttttcg ggattaatag caccagttgt      5340
ttgaaagcat tggaacttac ctatttactg aatcctctag tcaataagga taaagataga      5400
ttatatctcg gagaaggtgc aggtgcaatg ctgtcttgtt atgatgctac attaggaccc      5460
tgcatgaact attataattc aggtgttaat tcttgtgatc tcaacggaca aagagaatta      5520
aatatttatc cttcagaagt ggcactggta gggaagaaat tgaataatgt cacgagttta      5580
tgtcaaagag ttaaggtttt attcaatggg aatcctggat caacttggat agggaatgat      5640
gaatgtgaaa cactaatctg gaatgaatta cagaataatt caataggt tattcattgt      5700 gacatggaag gtggagaaca caaatgtgat caggtggtct acatgaaca ttatagtgtg      5760 atcaggattg cataccttgt tgggataag gacgttatct tagtaagcaa aattgcacca      5820
agattaggta cagactggac aaaacaatta agtttgtatt taagatactg gagagatgtc      5880
agcttaatag tgttgaaaac atctaaccca gcctctacag aaatgtatct gatatcaaaa      5940
gatcctaaat ctgatattat agaggatagt aatacagtat tggcaaacct tcttccatta      6000
tctaaagagg atagtattaa gatagaaaaa tggattctag ttgagaaagc caaagttcat      6060
gattggatag ttagagaatt aaaggaaggg agtgcatcgt caggtatgct aagaccttac      6120
catcaagcat tacaaatctt cggatttgag cctaatttaa acaaattatg tagagatttc      6180
ttatctacac taaatatagt agacacaaaa aattgtatta tcacatttga tagagtatta      6240
agagatacaa tctttgagtg gactcggata aaagacgcag ataagaagct aagacttaca      6300
ggtaaatatg atctatatcc tcttagagat tcaggtaagt taaagttatt ttctagaagg      6360
cttgtaatat cttggatagc attgtctatg tctacaagac tagtaacagg gtcattttcca     6420 gacattaaat ttgaatcaag actccaatta ggtatagtat caatatcctc tcgtgaaatc      6480
aaaaatctta gggttatatc aaagattgtc attgacaaat ttgaagatat tatacatagt      6540
gtgacctata ggttcttgac taaagaaata aaaatattga tgaaaatttt gggagcagtc      6600
aaattatttg gggcaagaca gagcacatct gctgatatca ctaatatcga tacatcggac      6660
tccatacaat ga                                                         6672
```

<210> SEQ ID NO 98
<211> LENGTH: 2280
<212> TYPE: DNA
<213> ORGANISM: Influenza A virus
<220> FEATURE:
<221> NAME/KEY: misc_feature
<223> OTHER INFORMATION: Influenza A virus (H1N1-1) polymerase PB2 (PB2) gene
<220> FEATURE:
<221> NAME/KEY: misc_feature
<222> LOCATION: (260)..(286)
<223> OTHER INFORMATION: targeting position

<400> SEQUENCE: 98

```
atggagagaa taaaagaact aagagatcta atgtcacaat cccgcacccg cgagatactc     60
actaagacca ctgtggacca tatggccata atcaaaaaat acacatcagg aaggcaagag    120
aagaaccccg cactcaggat gaagtggatg atggcaatga aatatccaat tacagcagac    180
aagagaataa tggaaatgat tcctgagagg aacgaacagg ggcaaaccct ctggagtaaa    240
acaaatgatg ccggctcaga ccgagtgatg gtatcacctc tggccgtaac gtggtggaat    300
aggaatggac caacaacaag cacagttcac tatccaaagg tatataaaac ttatttcgaa    360
aaagtagaaa ggttaaaaca tggaccttt ggccccgtcc acttcagaaa tcaagttaaa     420
ataagaagga gagtcgacat taaccctggc cacgcagatc tcagtgccaa ggaggcgcag    480
gatgtgatca tggaagttgt cttcccaaat gaagtaggag ctagaatact aacatcggag    540
tcacagctga caataacaaa ggagaagaaa gaagagctcc aggattgtaa aattgccccc    600
ttgatggtag catacatgct agaaagagag ttggtccgca aaacgaggtt cctaccagtg    660
gctggtggaa caagcagtgt ctatattgaa gtgctgcatt taacccaagg aacatgctgg    720
gagcaaatgt acactccagg aggggaggtg agaaatgatg atattgacca aagtttgatt    780
atcgctgcca ggaacatagt aagaagagca acggtatcgg cagacccatt agcatctctg    840
ttggaaatgt gccacagcac gcagattgga ggaataagga tggtggacat ccttaggcag    900
aatccaacag aggaacaagc cgtggacata tgcaaggcag caatgggatt gaggattagc    960
tcatctttca gcttcggcgg attcactttc aaaagaacaa gcggatcgtc agtcaagaaa   1020
gaagaagaag tgcttacagg caaccttcaa acactgaaaa taagagtgca tgaggggtat   1080
gaagaattca caatggttgg gagaagagca acggccattc tcagaaaggc aaccagaaga   1140
ttgatccagc taatagtaag tgggagagat gagcagtcaa ttgctgaggc aataattgtg   1200
gccatggtat tttcacaaga ggattgcatg atcaaagcag tccgaggcga tctgaacttt   1260
gtcaataggg caaaccagcg actgaatccc atgcatcaac tcttgagaca tttccaaaaa   1320
gatgcaaaag tgcttttcca gaactgggga attgaaccca tcgacaatgt aatgggaatg   1380
atcggaatat tacccgatat gaccccaagc actgagatgt cgctgagggg gataagagtc   1440
agcaaaatgg gagtagatga gtactccagc acggagagag tggtggtgag cattgaccga   1500
tttttgaggg ttcgggatca acgggggaac gtactattgt ctcccgaaga agtcagtgag   1560
acacaaggaa cagagaagct gacaataact tattcgtcat caatgatgtg ggagatcaac   1620
ggtcctgagt cggtgctggt caacacttat cagtggatca ttaggaactg ggaaactgtg   1680
aaaatccaat ggtcacaaga tcccacaatg ttatacaata agatggaatt cgaaccattt   1740
cagtcccttg tccctaaagc ggccagaagt caatacagcg gattcgtgag aacactgttc   1800
caacagatgc gagatgtgct tggaacattt gacactgttc aaataataaa acttctccct   1860
tttgctgctg ctccaccaga gcagagtagg atgcaattct cctcactgac tgtgaatgtg   1920
```
agaggatcag gaatgaggat actggtaaga ggcaattctc cagtgttcaa ttacaacaaa 1980
gccaccaaga ggcttacagt tcttgggaaa gatgcaggtg cattgaccga agatcctgat 2040
gaaggcacag ctggagtgga atctgctgtc ctgagaggat tcctcatttt gggcaaagaa 2100
gacaagagat atggcccagc attaagtatc aatgaattga gcaatcttgc aaaaggagag 2160
aaggctaatg tgttaattgg gcaaggagac gtagtgttgg taatgaaacg gaaacgggac 2220
tctagcatac ttactgacag ccagacagcg accaaaaagga ttcggatggc catcaattag 2280

<210> SEQ ID NO 99
<211> LENGTH: 2274
<212> TYPE: DNA
<213> ORGANISM: Influenza A virus
<220> FEATURE:
<221> NAME/KEY: misc_feature
<223> OTHER INFORMATION: Influenza A virus (H1N1-2) polymerase PB1
<220> FEATURE:
<221> NAME/KEY: misc_feature
<222> LOCATION: (941)..(961)
<223> OTHER INFORMATION: targeting position

<400> SEQUENCE: 99
atggatgtca atccgacatt acttttctta aaagtgccag cacaaaatgc tataagcaca 60
acttttcctt atactggtga ccctccttac agccatggga caggaacagg gtacaccatg 120
gatacagtca acaggacaca ccagtactca gaaagaggaa gatggacaaa aaataccgaa 180
acgggagcac cgcaacttaa cccaattgat ggtcccttac cggaagacaa tgaaccaagt 240
ggctatgccc aaacagattg tgtattagaa gcaatggctt tccttgaaga atcccatccc 300
ggtatctttg aaaactcttg tattgaaaca atggaggttg ttcaacaaac aagggtggac 360
aaactgacac aaggcagaca gacctatgac tggactctaa ataggaacca gcctgctgcc 420
acagcattgg caaacactat agaagtattc agatcaaacg gcctcatagc aaatgaatct 480
ggaaggctaa tagacttcct taaagatgta atggagtcga tggacagagg cgaagtagag 540
gtcacaactc attttcaaag aaagaggaga gtgagagaca atgtaactaa aaaaatggtg 600
acccaaagaa caataggcaa aaagaaacat aaattagaca aaagaagtta cctaattagg 660
gcattaaccc tgaacacaat gaccaaagat gctgagaggg ggaaactaaa acgcagagca 720
attgcaaccc caggaatgca aataaggggg tttgtatact ttgttgagac actggcaaga 780
agcatatgtg aaaagcttga acaatcagga ttgccagttg gaggaaatga gaagaaagca 840
aagttagcaa atgttgtaag gaagatgatg accaactccc aggacactga aatttctttc 900
accataaccg gagacaacac aaaatggaac gaaaatcaaa accctagaat gttcttggcc 960
atgatcacat atataaccaa aaatcagcct gaatggttca gaaatattct aagtattgct 1020
ccaataatgt tttcaaacaa gatggcgaga ctaggtaagg ggtacatgtt tgaaagcaag 1080
agtatgaaac tgagaactca aatacctgca gagatgctag ccaacataga cttgaaatat 1140
ttcaatgatt caactaaaaa gaaaattgaa aaaatccgac cattattaat agatggaact 1200
gcatcattga gtcctggaat gatgatgggc atgttcaata tgttgagcac cgtattgggc 1260
gtctccattc tgaatcttgg gcaaaagaga tacaccaaga ctacttactg gtgggatggt 1320
cttcaatcgt ctgatgattt tgctttaatt gtgaacgcac ccaactatgc aggaattcaa 1380
gctggagttg acaggtttta tcgaacctgt aagctgctcg gaattaatat gagcaaaaag 1440
aagtcttaca taaacagaac aggtaccttt gaattcacga gctttttcta tcgtcatggg 1500
tttgttgcca atttcagcat ggagcttcct agttttgggg tgtctggggt caatgaatct 1560
gcagacatga gtattggagt cactgtcatc aaaaacaata tgataaacaa tgaccttggc 1620
ccagcaactg ctcaaatggc ccttcagtta tttataaaag attacaggta cacttatcga 1680
tgccaccgag gtgacacaca aatacaaacc cgaagatcat ttgagataaa gaaactatgg 1740
gaccaaaccc gctcaaaagc tggactgttg gtctctgatg gaggccccaa tttgtataac 1800
attagaaatc tccatattcc tgaagtttgc ttgaaatggg agttgatgga tgaggattac 1860
caggggcgtt tatgcaaccc attaaacccg tttgtcagcc acaaagagat tgaatcagtg 1920
aacagtgcag tgataatgcc ggcacatggt ccagccaaaa atatggagta tgacgctgtt 1980
gcaacaacac actcctgggt ccccaaaaga aatcgatcca ttttgaacac gagccaaagg 2040
gggatacttg aagatgagca aatgtatcag aggtgctgca atttatttga aaaattcttc 2100
ccaagtagct catacagaag accagttgga atatccagta tggtagaggc tatggtctca 2160
agagcccgaa ttgatgcacg gattgatttc gaatctggaa ggataaagaa agaggaattt 2220
gctgagatca tgaagatctg ttccaccatt gaagacctca gacggcaaaa atga 2274

<210> SEQ ID NO 100
<211> LENGTH: 1701
<212> TYPE: DNA
<213> ORGANISM: Influenza A virus
<220> FEATURE:
<221> NAME/KEY: misc_feature
<223> OTHER INFORMATION: Influenza A virus (H3N2) hemagglutinin (HA)
<220> FEATURE:
<221> NAME/KEY: misc_feature
<222> LOCATION: (29)..(50)
<223> OTHER INFORMATION: targeting position

<400> SEQUENCE: 100
atgaagacta tcattgcttt gagctacatt ttctgtctgg ttctcggcca agattttcca 60
ggaaatgaca acagcacagc aacgctgtgc ctgggacatc atgcggtgcc aaacggaaca 120
ctagtgaaaa caatcacaaa tgatcagatt gaagtgacta atgctactga gctggttcag 180
agttcctcaa cggggaaaat atgcaacaat cctcatcgaa tccttgatgg aatagactgc 240
acactgatag atgctctatt gggggaccct cattgtgatg gctttcaaaa tgagacatgg 300
gaccttttcg ttgaacgcag caaagctttc agcaactgtt acccttatga tgtgccagat 360
tatgcctccc ttaggtcact agttgcctcg tcaggcactc tggagtttat caatgaaggc 420
ttcacttgga ctggggtcac tcagaatggg ggaagcaatg cttgcaaaag gggacctgat 480
aacggttttt tcagtagact gaactggttg tacaaatcag gaagcacata tccagtgctg 540
aacgtgacta tgccaaacaa tgacaatttt gacaaactat acatttgggg ggttcaccac 600
ccgagcacgg accaagaaca aaccagccta tatgttcaag catcagggag agtcacagtc 660
tctaccaaga gaagccagca aactataatc ccgaatatcg ggtctagacc ctgggtaagg 720
ggtctgtcta gtagaataag catctattgg acaatagtta aaccaggaga catactggta 780
attaatagta atgggaacct aattgctcct cggggttatt tcaaaatgcg cactgggaaa 840
agctcaataa tgaggtcaga tgcacctatt ggcacctgca tttctgaatg catcactcca 900
aatggaagca ttcccaatga caagcccttt caaaacgtaa acaagatcac atatggagca 960
tgtcccaagt atgttaagca aaacaccctg aagttggcaa cagggatgcg aaatgtacca 1020
gagaaacaaa ctagaggcct attcggcgca atagcaggtt tcatagaaaa tggttgggag 1080
ggaatgatag acggttggta cggtttcagg catcaaaatt ctgagggcac aggacaagca 1140
gcagatctta aaagcactca agcagccatc gaccaaatca atgggaaact gaatagggta 1200

| | | | | |
|---|---|---|---|---|
| atcgagaaga | cgaacgagaa | attccatcaa | atcgaaaagg aattctcaga agtagaaggg | 1260 |
| agaattcagg | acctcgagaa | atacgttgaa | gacactaaaa tagatctctg gtcttacaat | 1320 |
| gcggagcttc | ttgtcgctct | ggagaaccaa | catacaattg atctgactga ctcggaaatg | 1380 |
| aacaaactgt | ttgaaaaaac | aaggaggcaa | ctgagggaaa atgctgagga catgggcaat | 1440 |
| ggttgcttca | aaatatacca | caaatgtgac | aatgcttgca tagggtcaat cagaaatggg | 1500 |
| acttatgacc | atgatgtata | cagagacgaa | gcattaaaca accggtttca gatcaaaggt | 1560 |
| gttgaactga | agtcaggata | caaagactgg | atcctgtgga tttcctttgc catatcatgc | 1620 |
| ttttttgcttt | tgtgttgtttt | gctggggttc | atcatgtggg cctgccagaa aggcaacatt | 1680 |
| aggtgcaaca | tttgcatttg | a | | 1701 |

<210> SEQ ID NO 101
<211> LENGTH: 1497
<212> TYPE: DNA
<213> ORGANISM: Influenza A virus
<220> FEATURE:
<221> NAME/KEY: misc_feature
<223> OTHER INFORMATION: Influenza A virus (H5N1) segment 5
      nucleocapsid protein (NP)
<220> FEATURE:
<221> NAME/KEY: misc_feature
<222> LOCATION: (1222)..(1242)
<223> OTHER INFORMATION: targeting position

<400> SEQUENCE: 101

| | | | | |
|---|---|---|---|---|
| atggcgtctc | aaggcaccaa | acgatcttat | gaacaaatgg aaactggtgg agagcgccag | 60 |
| aatgctactg | agatcagggc | atctgttgga | agaatggtta gtggcattgg gaggttctac | 120 |
| atacagatgt | gcacagaact | caaactcagt | gactatgaag ggagactgat ccagaacagc | 180 |
| ataacaatag | aaaggatggt | actttctgca | tttgatgaaa gaaggaacag gtacctggaa | 240 |
| gaacacccca | gtgcggggaa | ggaccccaag | aaaactggag gcccaattta tcggaggaga | 300 |
| gacggaaagt | gggtgaggga | gctgattctg | tacgacaaag aggagatcag gaggatttgg | 360 |
| cgtcaagcga | acaatggaga | ggacgcaact | gctggtctta cccacctgat gatatggcat | 420 |
| tccaatctaa | atgatgccac | atatcagaga | acgagagctc tagtgcgtac tgggatggac | 480 |
| cccaggatgt | gctctctgat | gcaagggtca | actctcccga ggagatctgg agctgccggt | 540 |
| gcagcagtga | aggggtagg | acaatggtg | atggagctga ttaggatgat aaaacgaggg | 600 |
| gtcaacgacc | ggaatttctg | gagaggcgaa | aatggaagaa gaactaggat tgcatatgag | 660 |
| agaatgtgca | acatcctcaa | agggaaattc | caaacagcag cacaaagagc aatgatggat | 720 |
| caagtgcgag | agagcagaaa | tcctggaaat | gctgaaattg aagatctcat ttttctggca | 780 |
| cggtctgcac | tcatcctgag | aggatcagtg | gcccataagt cctgcttgcc tgcttgtgta | 840 |
| tacggacttg | cagtggccag | tggatatgac | tttgagagag aagggtactc tctggttgga | 900 |
| atagatcctt | tccgtctgct | tcaaaacagc | caggtcttta gtctcattag gccaaacgag | 960 |
| aatccagcac | ataagagtca | attagtgtgg | atggcatgtc actctgcagc atttgaggac | 1020 |
| cttagagtct | caagcttcat | cagaggaaca | agagtggtcc caagaggaca gctatccacc | 1080 |
| agaggggttc | aaattgcttc | aaatgagaac | atggaagtaa tggactccaa cactcttgaa | 1140 |
| ctgaggagta | gatattgggc | tataagaacc | agaagcgggg gaaacaccaa ccagcagaag | 1200 |
| gcatctgcag | ggcagatcag | cgttcagccc | actttctcgg tacagagaaa ccttcccttc | 1260 |
| gaaagagcga | ccattatggc | agcatttaca | ggaaatgctg aggcagaac gtctgacatg | 1320 |

-continued

```
aggactgaaa tcataagaat gatggaaagt gccagaccag aagatgtgtc attccagggg   1380
cggggagtct tcgagctctc ggacgaaaag gcaacgaacc cgatcgtgcc ttcctttgac   1440
atgaataatg aaggatctta tttcttcgga gacaatgcag aggagtatga caattaa      1497

<210> SEQ ID NO 102
<211> LENGTH: 1683
<212> TYPE: DNA
<213> ORGANISM: Influenza A virus
<220> FEATURE:
<221> NAME/KEY: misc_feature
<223> OTHER INFORMATION: Influenza A virus (H7N9) segment 4
      hemagglutinin (HA)
<220> FEATURE:
<221> NAME/KEY: misc_feature
<222> LOCATION: (196)..(212)
<223> OTHER INFORMATION: targeting position

<400> SEQUENCE: 102
atgaacactc aaatcctggt attcgctctg attgcgatca ttccaacaaa tgcagacaaa     60
atctgcctcg gacatcatgc cgtgtcaaac ggaaccaaag taaacacatt aactgaaaga    120
ggagtggaag tcgtcaatgc aactgaaaca gtggaacgaa caaacatccc caggatctgc    180
tcaaaaggga aaaggacagt tgacctcggt caatgtggac tcctggggac aatcactgga    240
ccacctcaat gtgaccaatt cctagaattt tcagccgatt taattattga gaggcgagaa    300
ggaagtgatg tctgttatcc tgggaaattc gtgaatgaag aagctctgag gcaaattctc    360
agagaatcag gcggaattga caaggaagca atgggattca catacagtgg aataagaact    420
aatggagcaa ccagtgcatg taggagatca ggatcttcat tctatgcaga aatgaaatgg    480
ctcctgtcaa acacagataa tgctgcattc ccgcagatga ctaagtcata taaaaataca    540
agaaaaagcc cagctctaat agtatggggg atccatcatt ccgtatcaac tgcagagcaa    600
accaagctat atgggagtgg aaacaaactg gtgacagttg ggagttctaa ttatcaacaa    660
tcttttgtac cgagtccagg agcgagacca caagttaatg gtctatctgg aagaattgac    720
tttcattggc taatgctaaa tcccaatgat acagtcactt tcagtttcaa tggggctttc    780
atagctccag accgtgcaag cttcctgaga ggaaaatcta tgggaatcca gagtggagta    840
caggttgatg ccaattgtga aggggactgc tatcatagtg gagggacaat aataagtaac    900
ttgccatttc agaacataga tagcagggca gttggaaaat gtccgagata tgttaagcaa    960
aggagtctgc tgctagcaac agggatgaag aatgttcctg agattccaaa gggaagaggc   1020
ctatttggtg ctatagcggg tttcattgaa aatggatggg aaggcctaat tgatggttgg   1080
tatggtttca gacaccagaa tgcacaggga gagggaactg ctgcagatta caaaagcact   1140
caatcggcaa ttgatcaaat aacaggaaaa ttaaaccggc ttatagaaaa aaccaaccaa   1200
caatttgagt tgatagacaa tgaattcaat gaggtagaga agcaaatcgg taatgtgata   1260
aattggacca gagattctat aacagaagtg tggtcataca atgctgaact cttggtagca   1320
atggagaacc agcatacaat tgatctggct gattcagaaa tggacaaact gtacgaacga   1380
gtgaaaagac agctgagaga gaatgctgaa gaagatggca ctggttgctt tgaaatattt   1440
cacaagtgtg atgatgactg tatggccagt attagaaata acacctatga tcacagcaaa   1500
tacagggaag aggcaatgca aaatagaata cagattgacc cagtcaaact aagcagcggc   1560
tacaaagatg tgatactttg gtttagcttc ggggcatcat gtttcatact tctagccatt   1620
```

```
gtaatgggcc ttgtcttcat atgtgtaaag aatggaaaca tgcggtgcac tatttgtata    1680
taa                                                                  1683
```

EXTRACTION, PREPARATION, AND APPLICATION OF PLANT MICRO-RIBONUCLEIC ACID

TECHNICAL FIELD

The present invention belongs to the field of biology. In particular, the present invention relates to a method of extracting plant microRNAs and application thereof.

BACKGROUND ART

Micro ribonucleic acids (microRNA, miRNA or miR) are a class of non-coding, single stranded, small ribonucleic acid molecules with 19-23 nucleotides in length. They exist extensively in the cells of animals and plants and are highly conserved in evolution. MicroRNA inhibits the translation of corresponding proteins through recognizing the 3' end non-translated sequence of target messenger RNA (mRNA) and imcompletely complementing thereto. As a powerful regulatory factor for mRNA, microRNAs are closely related to physiological activities, which relates to life activities such as the individual development, tissue differentiation, apoptosis and energy metabolism of organisms and the like; and meanwhile, microRNAs are also closely related to the occurrence and development of many diseases.

Currently, the research on plant microRNAs focuses on the regulatory effects of microRNAs on plants per se, including the effects on the growth and development, signal transduction, and behaviours under stress of plants. The application of research achievements focuses on the improvement of plant species, for example, the regulation of the expression of nutrient elements in edible parts of crops.

Patent PCT/CN 2010/000677 discloses the regulatory effects of MIR164 derived from *Oryza sativa* on the root system of plants, and proposes the construction of a nucleic acid fragment comprising the MIR164 sequence, which is transformed into *Oryza sativa* plants, thus obtaining transgenic *Oryza sativa* having a root system more powerful than that of general *Oryza sativa*. Patent PCT/IB 2010/055600 discloses that the up-regulation of several microRNAs comprising MIR156 can improve the tolerance of plants to the stress factors in environment, and then improve the biomass, vigor and yield of the plants.

Currently, the existing researches are merely limited to the regulatory effects of plant microRNAs on the physiological activities of plants per se, and the regulatory effects of plant microRNAs on the physiological activities of animals and the extraction of plant microRNAs still need investigation.

Contents of the Invention

One of the objects of the present invention is to provide a plant microRNA having the function of regulating non-plant target genes, or a plant extract containing said microRNA and preparation method and use thereof.

Another object of the present invention is to provide a method of identifying plant functional microRNAs.

In a first aspect of the present invention, provided is an isolated plant functional microRNA or an extract containing said plant functional microRNA, said plant functional microRNA is an endogenous microRNA derived from a certain plant and exists in the water-soluble and/or liposoluble extracts of said plants, moreover, said plant functional microRNA has the function of regulating non-plant target genes.

In another preferred example, said plant functional microRNAs include MIR2911; and the content of MIR2911 in said isolated plant functional microRNAs or the extract containing said plant functional microRNAs is greater than or equal to 70% by the total amount of microRNAs.

In another preferred example, the content of MIR2911 is greater than or equal to 80%; preferably, greater than or equal to 90%; and more preferably is 100%.

In another preferred example, said total amount of microRNAs refers to the sum of the amount of microRNAs of 18-24 nt in length.

In another preferred example, said regulation includes inhibition (down-regulation) of the expression of the target gene, and promotion (up-regulation) of the expression of the target gene.

In another preferred example, said non-plant target gene includes bacterial gene, viral gene, chlamydial gene, yeast gene, and animal gene.

In another preferred example, said plant includes medicinal plants, fruit and vegetable plants, and ornamental plants; preferably includes *Lonicera japonica*, *Isatis tinctoria*, *Isatis indigotica*, *Baphicacanthus cusia*, *Populus diversifolia*, *Vigna unguiculata*, cotton, Chinese cabbage or *Solanum tuberosum*. Preferably, said plant is *Lonicera japonica*, *Isatis tinctoria*, *Isatis indigotica*, *Baphicacanthus cusia* or *Populus diversifolia*; and more preferably, said plant is *Lonicera japonica*.

In another preferred example, said plant functional microRNAs are microRNA species enriched in the water-soluble and/or liposoluble extracts of said plant (for example, microRNA species having an abundance of top 20, and more preferably top 10).

In another preferred example, said plant functional microRNAs further include one or more selected from the group comprising: MIR156h, MIR166f, MIR396a, MIR166a, MIR168a, MIR1440, MIR2910, MIR2915, MIR2916, MIR818d, MIR159e, MIR159c, MIR156j, MIR1432, MIR166k, MIR167b, MIR396c, MIR156e, MIR169k, MIR167c, MIR160d, MIR399a, MIR156d, MIR160e, MIR169n, MIR166l, MIR159f, MIR166c, MIR159b, MIR166j, MIR167i, MIR169c, MIR164c, MIR167j, MIR167g, MIR160c, MIR399e, MIR399b, MIR529b, MIR164e, MIR166d, MIR166h, MIR164b, MIR156f, MIR164a, MIR169l, MIR166m, MIR164f, MIR156k, MIR166g, MIR166b, MIR160b, MIR166e, MIR159d, MIR818e, MIR172a, MIR156b, MIR399g, MIR169b, MIR399f, MIR167a, MIR394, MIR156a, MIR166i, MIR167f, MIR319a, MIR156g, MIR166n, MIR399c, MIR160a, MIR159a.1, MIR156c, MIR319b, MIR169o, MIR167h, MIR156i, MIR167d, MIR169a, MIR172d, MIR818b, MIR164d, MIR167e, MIR396b, MIR2914 (Table 1).

In another preferred example, said plant extract includes the water-soluble and/or liposoluble extract of plants.

In another preferred example, said plant extract includes the extracts of branches, leaves, roots, flowers, fruits, and/or stems of plants.

In a second aspect of the present invention, provided is the use of the isolated plant functional microRNAs or an extract containing said plant functional microRNAs as described in the first aspect of the present invention in (a) preparing a composition for regulating non-plant target genes; or (b) preparing a pharmaceutical for treating diseases associated with non-plant target genes.

In another preferred example, said non-plant target gene includes bacterial gene, viral gene, chlamydial gene, yeast gene, and animal gene.

In another preferred example, said non-plant target gene is a gene of a pathogen (including bacteria, viruses, and chlamydia, etc.).

In another preferred example, said diseases associated with non-plant target genes include: tumors (such as liver cancer and lung cancer), acute and chronic infectious diseases (for example, viral diseases such as viral influenza, viral hepatitis, acquired immunodeficiency syndrome, and SARS; bacterial diseases such as tuberculosis and bacterial pneumonia; and acute and chronic infectious diseases caused by pathogenic microorganisms); and other acute and chronic diseases (for example, respiratory system diseases, immune system diseases, blood and hematopoietic system diseases such as circulatory diseases including cardiovascular and cerebrovascular diseases, metabolic diseases related to endocrine system, digestive system diseases, nervous system diseases, urinary system diseases, reproductive system diseases and motor system diseases).

In another preferred example, said plant functional microRNAs include MIR2911. More preferably, said pharmaceutical is used for treating viral influenza.

In a third aspect of the present invention, provided is a composition which comprises (a) a carrier acceptable in pharmaceutics or bromatology and (b) the isolated plant functional microRNAs and/or the plant extract containing said plant functional microRNAs as described in the first aspect of the present invention.

In another preferred example, said composition consists of or substantially consists of components (a) and (b).

In another preferred example, the content of component (b) accounts for 0.01%-99 wt % of the total weight of the composition, more preferably 0.1%-90 wt % (calculated as microRNA).

In another preferred example, said composition includes a pharmaceutical composition, a food composition or a health care product composition.

In another preferred example, the method for preparing said composition comprises the step of mixing said plant functional microRNAs or the plant extract containing said functional microRNAs with a carrier acceptable in pharmaceutics or bromatology to form said composition.

In another preferred example, said plant functional microRNAs are derived from the following plants: medicinal plants, fruit and vegetable plants, and ornamental plants, and regulates the non-plant target genes selected from the group comprising bacterial gene, viral gene, chlamydial gene, yeast gene, and animal gene.

In another preferred example, said plant functional microRNAs are derived from *Lonicera japonica, Isatis tinctoria, Isatis indigotica, Baphicacanthus cusia* or *Populus diversifolia*. More preferably, plant functional microRNAs includes MIR2911.

In a fourth aspect of the present invention, provided is a method for in vitro non-therapeutic regulation of the expression of non-plant target genes, wherein the non-plant target genes include bacterial gene, viral gene, chlamydial gene, yeast gene, and animal gene, said method comprises the step of culturing a biological material containing said target genes in the presence of the isolated plant functional microRNAs or an extract containing said plant functional microRNAs as described in the first aspect of the present invention to regulate the expression of said non-plant target genes.

In another preferred example, said target gene is a gene of a pathogen (including bacteria, viruses, and chlamydia, etc.).

In another preferred example, said biological material includes viruses, cells and tissues.

In another preferred example, said plant functional microRNAs are derived from the following plants: medicinal plants, fruit and vegetable plants, and ornamental plants.

In another preferred example, said plant functional microRNAs are derived from *Lonicera japonica, Isatis tinctoria, Isatis indigotica, Baphicacanthus cusia* or *Populus diversifolia*. More preferably, plant functional microRNAs include MIR2911.

In a fifth aspect of the present invention, provided is a method of identifying plant functional microRNAs, wherein said plant functional microRNAs have the function of regulating non-plant target genes, said method comprising the steps of:
(1) Providing an extract of a certain plant;
(2) Determining the species or levels of the plant endogenous microRNAs in said extract; and
(3) Performing alignment and analysis on the sequences of the determined plant microRNAs and non-plant target genes to identify the plant functional microRNAs having the function of regulating the non-plant target genes.

In another preferred example, said non-plant target gene includes the genes in a gene database.

In another preferred example, said non-plant target gene includes bacterial gene, viral gene, chlamydial gene, yeast gene, and animal gene.

In another preferred example, said non-plant target gene is a gene of a pathogen.

In another preferred example, said plant includes medicinal plants, and fruit and vegetable plants.

In another preferred example, microRNA species having an abundance in the extract of top 20 (more preferably top 10) are picked out in step (3) for alignment and analysis.

In another preferred example, plant microRNA species having a Lm/La ratio greater than or equal to 130% (more preferably greater than or equal to 150%; and still more preferably greater than or equal to 200%) are picked out in step (3) for alignment and analysis, wherein Lm is the abundance (or level) of a certain plant microRNA in the extract, and La is the average abundance (or level) of said plant total microRNAs.

In a sixth aspect of the present invention, provided is a plant functional microRNA molecule which is identified by the method as described in the fifth aspect of the present invention.

In another preferred example, said microRNA molecule includes MIR2911.

In a seventh aspect of the present invention, provided is a method of preparing a composition which comprises the steps of:
artificially synthesizing the plant functional microRNA molecule as described in the sixth aspect of the present invention; and
mixing said plant functional microRNA molecule with a carrier acceptable in pharmaceutics or bromatology to form the composition.

In an eighth aspect of the present invention, provided is the use of a microRNA molecule MIR2911 or an extract containing MIR2911 for preparing a pharmaceutical for treating viral influenza.

In another preferred example, said extract (unconcentrated or concentrated) contains 0.01-100 nM (preferably 0.1-20 nM) MIR2911; or In said extract (unconcentrated or concentrated), the content of MIR2911 is greater than or equal to 70%; preferably greater than or equal to 80%; more preferably greater than or equal to 90%; and most preferably is 100% by the total amount of microRNAs.

In a ninth aspect of the present invention, provided is a method of preventing or treating diseases, wherein said diseases are diseases associated with non-plant target genes, said method comprises the step of administering the isolated plant functional microRNAs or the extract containing said plant functional microRNAs as described in the first aspect of the present invention or the composition in the third aspect of the present invention to a subject in need thereof to prevent or treat said diseases, wherein said plant functional microRNAs have the function of regulating non-plant target genes.

In another preferred example, said subject includes mammals (such as human).

In another preferred example, said non-plant target gene includes bacterial gene, viral gene, chlamydial gene, yeast gene, and animal gene.

In another preferred example, said non-plant target gene is a gene of a pathogen.

In a tenth aspect of the present invention, provided is a method of screening candidate substances of antiviral active ingredients, which comprises the steps of:

(a) Providing isolated plant functional microRNAs or an extract containing said plant functional microRNAs;

(b) Determining the stability of each microRNA in said plant functional microRNAs to select the microRNA species having high stability;

(c) Aligning said microRNAs having high stability which are selected in the above step with non-plant target genes to determine whether said microRNAs of high stability match with or bind with the non-plant target genes;

wherein, if the aligning results indicate that said microRNAs of high stability can match with or bind with the non-plant target genes, the microRNA species are selected as the candidate antiviral active ingredients.

In another preferred example, said method also comprises the steps of:

(d) Verifying whether the candidate antiviral active ingredients has an antiviral activity or not in in vitro tests or animal tests.

In another preferred example, said microRNAs of high stability are selected from the group comprising:

(i) A microRNA having the stability of top 5, preferably top 3, and more preferably top 1 among said plant functional microRNAs, or the extract containing said plant functional microRNAs;

(ii) A microRNA whose stability meets the following equation $C_{12}/C_0$ greater than or equal to 80% wherein $C_0$ is the concentration when placed for 0 hour; $C_{12}$ is the concentration when placed for 12 hours.

More preferably, $C_0$ is other than 0.

In another preferred example, said non-plant target gene is a viral gene.

In another preferred example, in step (a), said miRNA is a species having a ranking of abundance in fresh plants (from high to low) after the fifth and preferably after the tenth.

In an eleventh aspect of the present invention, provided is a method of preparing a composition which comprises the steps of:

artificially synthesizing plant functional microRNA molecules, wherein said plant functional microRNA molecules are candidate antiviral active ingredients screened using the method described in the tenth aspect; and mixing said plant functional microRNA molecules with a carrier acceptable in pharmaceutics or bromatology to form the composition.

In a twelfth aspect of the present invention, provided is a method of improving the abundance of MIR2911 which comprises the steps of:

(a) Providing an extract containing plant functional microRNAs, wherein said plant functional microRNAs include n microRNA species, wherein n is a positive integer greater than or equal to 2 (preferably greater than or equal to 5 or greater than or equal to 10), and wherein one microRNA is MIR2911;

(b) Subjecting said extract to aging treatment (such as placement) to obtain an aged extract and determining the abundance of MIR2911 in said aged extract, comparing the abundance with a preset value, and terminating the aging treatment when the abundance of MIR2911 is greater than or equal to the preset value to obtain an extract having an improved abundance of MIR2911.

In another preferred example, said extract is a water extract or an alcohol extract.

In another preferred example, said aging treatment is placement at 20° C.-50° C. for 2 hours to 10 days.

In another preferred example, said method also comprises using the obtained extract having an improved abundance of MIR2911 to prepare pharmaceuticals or placing same at a low temperature (such as 0° C. to −4° C. or a lower temperature) for storage.

In another preferred example, said preset value is 60%, 70%, 80%, 90%, 95%, or 99%.

In another preferred example, said abundance is calculated as the following equation abundance=$S_1/\Sigma Si \times 100\%$ wherein $S_1$ is the amount (or concentration) of MIR2911, i=1 to n, Si is the amount (or concentration) of the $i^{th}$ microRNA, wherein microRNA is RNA of 18-26 nt in length.

It should be understood that all of the various technical features described above and the various technical features specifically described hereinafter (such as examples) can be combined with one another within the scope of the present invention, so as to form new or preferred technical solutions. Due to space limitations, this is no longer tired out one by one.

DESCRIPTION OF DRAWINGS

In FIG. 5A, FIG. 5B, and FIG. 5C, "uninfected" represents the cells not infested by influenza viruses; "infected and untreated" represents the cells infested by influenza viruses and not treated with any pharmaceutical; "MIR2911" represents the cells infested by influenza viruses and treated with MIR2911; "NC" represents the cells infested by influenza viruses and treated with a nonsense sequence RNA of MIR2911; "Tamiflu" represents the cells infested by influenza viruses and treated with Tamiflu (Oseltamivir, a specific influenza virus neuraminidase inhibitor).

In FIG. 7A and FIG. 7B, after infecting with influenza viruses, the non-treated HEK 293T cells are used as blank control and the HEK 293T cells treated with cell microvesicles not carrying MIR2911 are used as negative control.

The time points for detection are 0 h (0 hour), 1 h (1 hour), 2 h (2 hour), 3 h (3 hour), 4 h (4 hour), 5 h (5 hour), and 6 h (6 hour).

Figure 10:
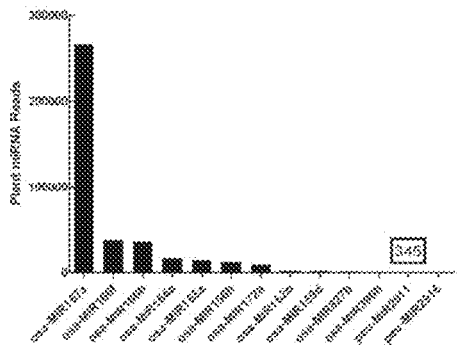

FIG. 10 shows the Solexa sequencing results of the plant miRNA in fresh *Lonicera japonica*.

Figure 11:
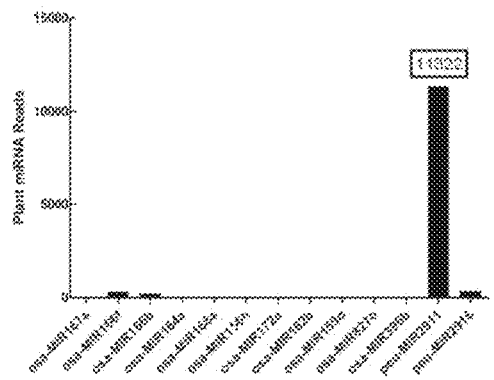

FIG. 11 shows the Solexa sequencing results of the plant miRNA in *Lonicera japonica* water extract.

Figure 12:
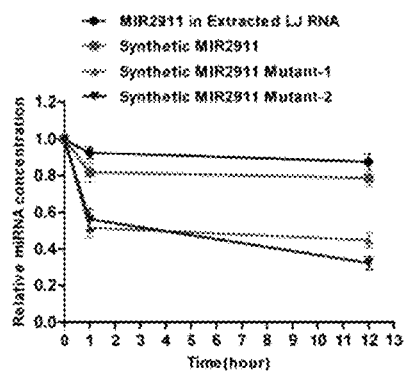

FIG. 12 shows the real-time PCR results of MIR2911 in *Lonicera japonica* water extract or synthetic MIR2911.

Figure 13:
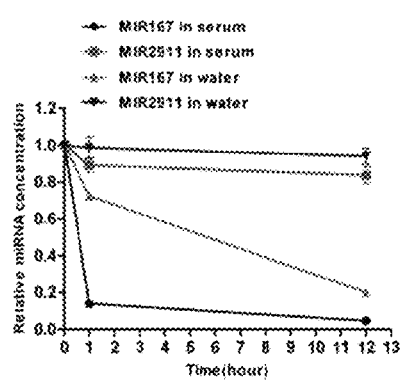

FIG. 13 shows the real-time PCR results of the expression amount of MIR2911 or MIR167 in sera or water.

Figure 14A:
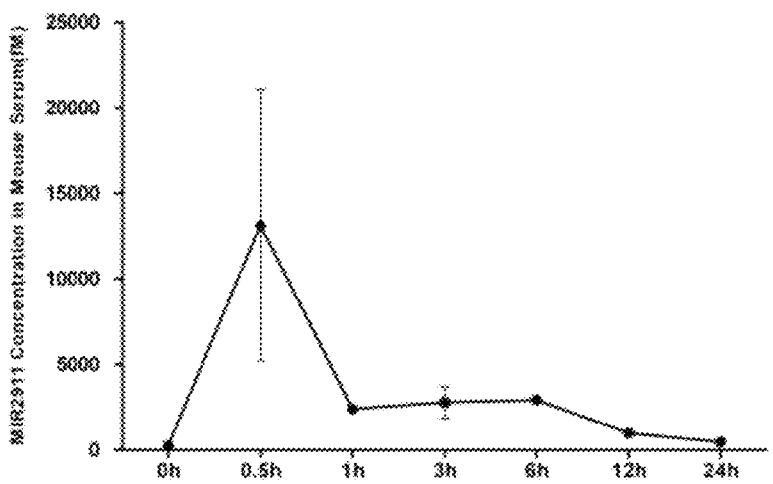

FIG. 14A shows the real-time PCR results of the expression amount of MIR2911 in mice sera at different time points after intragastrical administration of synthetic MIR2911. The time points for detection are 0 h (0 hour), 0.5 h (0.5 hour), 1 h (1 hour), 3 h (3 hour), 6 h (6 hour), 12 h (12 hour), and 24 h (24 hour).

Figure 14B:
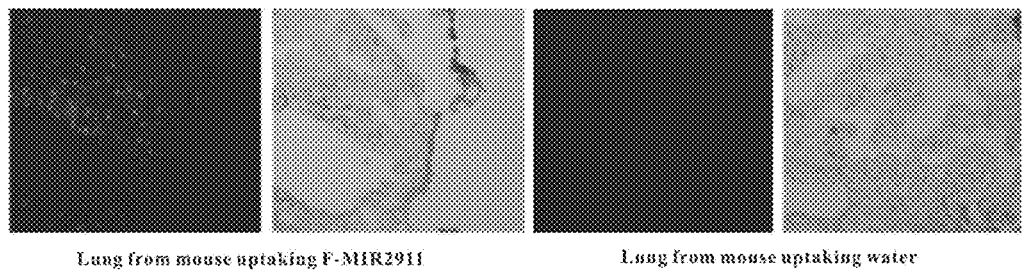

FIG. 14B shows the distribution of MIR2911 in mice organs after intragastrical administration of *Lonicera japonica* water extract.

Figure 15:
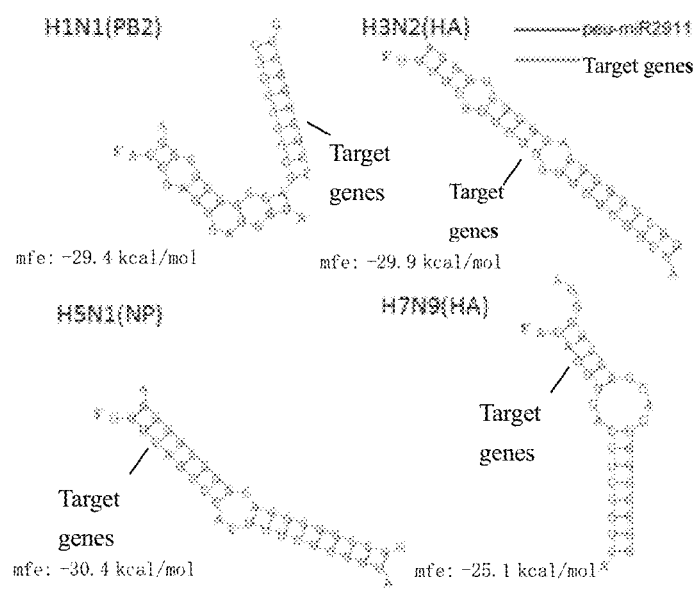

FIG. 15 shows the sequence analysis results of the predicted target genes of MIR2911. mfe represents the minimal folding free energy of the candidate target gene, the greater the absolute value of mfe, the higher the matching rate of the candidate target gene with Peu-MIR2911 sequence.

Figure 16:
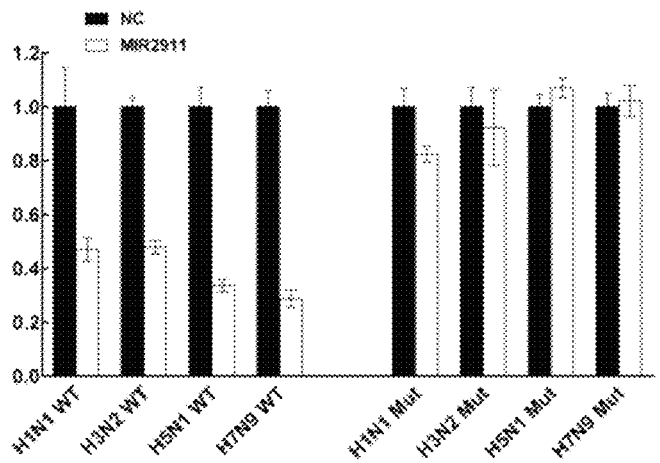

FIG. 16 shows the results of the detection of the predicted target genes by luciferase. The predicted genes include H3N2 gene, H71N9 gene, H1N1 gene, and H5N1 gene.

Figure 17:
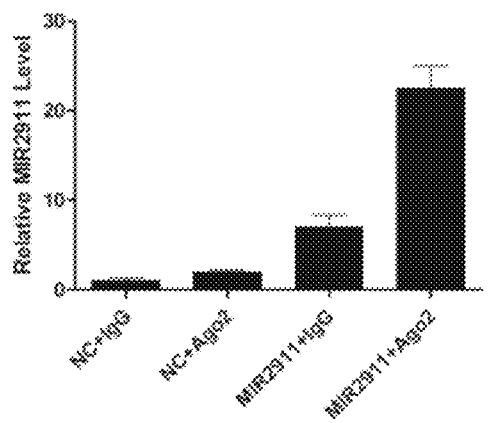

FIG. 17 shows the real-time PCR results of MIR2911 in MDCK cells after introducing the complex of MIR2911 and AGO2 in combination into the MDCK cells.

Figure 18:
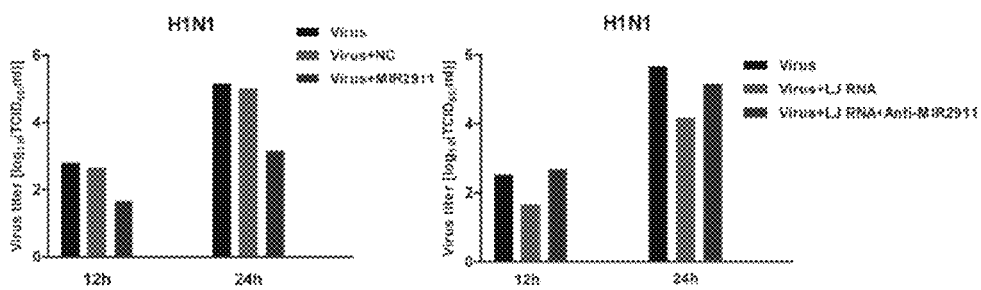

FIG. 18 shows the virus titer of influenza virus H1N1 in the MDCK cells transfected with the complex of MIR2911 and AGO2.

Figure 19:
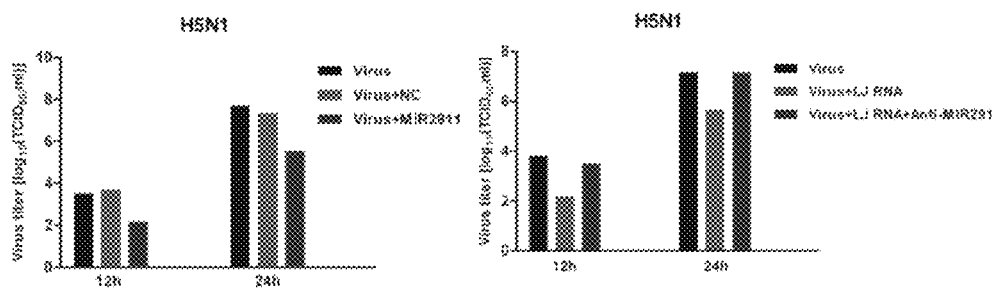

FIG. 19 shows the virus titer of influenza virus H5N1 in the MDCK cells transfected with the complex of MIR2911 and AGO2.

Figure 20:
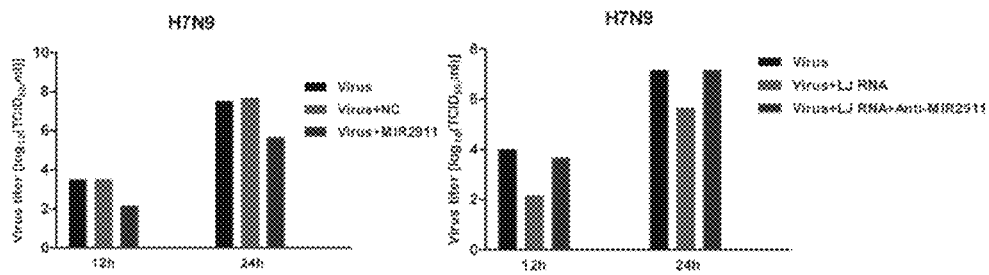

FIG. 20 shows the virus titer of influenza virus H7N9 in the MDCK cells transfected with the complex of MIR2911 and AGO2.

FIG. 21 shows the changes of virus titer EID50 at different time points in lungs of mice infected with H1N1 viruses after drinking MIR2911 solution.

FIG. 22 shows the changes of virus titer EID50 at different time points in lungs of mice infected with H1N1 viruses after drinking *Lonicera japonica* decoction+anti-MIR2911.

FIG. 23 shows the changes of virus titer EID50 at different time points in lungs of mice infected with H1N1 viruses after drinking MIR2911 solution.

FIG. 24 shows the changes of virus titer EID50 at different time points in lungs of mice infected with H1N1 viruses after drinking *Lonicera japonica* decoction+anti-MIR2911.

FIG. 25 shows the real-time PCR results of MIR2911 in fresh *Lonicera japonica*, dry *Lonicera japonica*, and mouse feed.

PARTICULAR EMBODIMENTS

After conducting long-term deep research, the inventors have unexpectedly found that an isolatable plant endogenous microRNA which stably exists in a plant extract or a plant extract containing said microRNA can be used for regulating the expression of the target gene of said endogenous microRNA in animal body and then used for regulating the physiological and pathological activities of animals. Therefore, the research can be used for guiding the preparation of pharmaceuticals or functional foods and the like. The present invention is accomplished by the inventors on this basis.

The present inventors also found that microRNA species such as MIR2911 have unusually high stability (far above a general microRNA), which can exist stably for a long term, and thus are particularly suitable for use as an active ingredient and applied in pharmaceuticals or other products.

As used herein, "osa" represents *Oryza sativa*; and "peu" represents *Populus diversifolia*.

Isolated Plant Functional microRNAs

The plant functional microRNAs described in the present invention are said plant endogenous microRNAs, which can stably exist in the water-soluble and/or liposoluble extracts of plants. Preferably, said plant functional microRNAs are microRNA species enriched in the water-soluble and/or liposoluble extracts of said plant (for example, microRNA species having an abundance of top 20, and more preferably top 10). In addition, the microRNAs in the present invention are of various forms, for example, pri-microRNAs, pre-microRNAs and mature microRNAs.

The examples of said plant functional microRNAs include (but not limited to) one or more microRNAs selected from Table 1, especially selected from the group comprising MIR156h, MIR166f, MIR396a, MIR166a, MIR168a, MIR1440, MIR2910, MIR2911, MIR2915, and MIR2916.

In another preferred example, said plant includes medicinal plants, fruit and vegetable plants, and ornamental plants; preferably includes *Lonicera japonica, Isatis tinctoria, Isatis indigotica, Baphicacanthus cusia, Populus diversifolia, Vigna unguiculata*, cotton, Chinese cabbage or *Solanum tuberosum*; more preferably, said plant is *Lonicera japonica, Isatis tinctoria, Isatis indigotica, Baphicacanthus cusia* or *Populus diversifolia*; and most preferably, said plant is *Lonicera japonica*.

The extracts containing said plant functional microRNAs described in the present invention include the water-soluble and/or liposoluble extracts of plants, for example, the extracts of branches, leaves, roots, flowers, fruits, and/or stems of the plants.

Extraction Method (Preparation Method of Plant Extracts)

The extraction method of the plant microRNAs described in the present invention mainly employs a solvent extraction method, that is, a solvent is employed to extract microRNAs from plants. In this case, said solvent includes water, a hydrophilic solvent, or a combination thereof. Said combination includes adding an appropriate amount of a hydrophilic solvent to water or adding an appropriate amount of water to a hydrophilic solvent. It should be understood that an appropriate amount of an auxiliary reagent such as a pH regulator (such as an acid or a base) and the like can also be added to the solvent.

The extraction can be carried out under any appropriate temperature (for example, from normal temperature to the temperature for solvent refluxing); and preferably employed are impregnation method, percolation method, decoction method, refluxing extraction method, continuous extraction method and the like.

During the extraction process, the plants can be pre-treated, for example, the plants are pulverized or subjected to enzyme treatment (such as cellulase, hemicellulase, pectinase, xylanase, neutral protease, papain, glucanase, and complex enzymes) and the like; and also, the extracted mixture can be subjected to a post-treatment, for example, a hydrophilic solvent (such as ethanol and the like) can be added to the extracted mixture after extracting the plants with water, which allows the mixture to precipitate via aging.

The obtained liquid after extraction can be used directly and can also be treated via filtration, concentration, and drying (such as freeze drying) to yield a solid for subsequent use.

Preferably, the extraction method for plant microRNAs described in the present invention is a water extraction method.

For instance, the method comprises the steps of taking an appropriate amount of *Lonicera japonica*, pulverizing same, placing *Lonicera japonica* powder in a water bath under a certain temperature (for example, from room temperature to a temperature for refluxing), heating same for several times (such as 1-5 times) with each time incubating for a period of time (such as 0.1-10 hours), and collecting liquid ready for use.

Alternatively, the method comprises the steps of taking an appropriate amount of *Lonicera japonica*, pulverizing same, placing *Lonicera japonica* powder in a water bath under a certain temperature (for example, from room temperature to a temperature for refluxing), heating same for several times (such as 1-5 times) with each time incubating for a period of time (such as 0.1-10 hours), concentrating the extracted liquid to a certain volume, adding an appropriate amount of ethanol to precipitate out a majority of mucilaginous substances, filtrating, and collecting filtrates ready for use.

Determination

The plant extracts are collected after extracting the plants, and the species and contents of the plant microRNAs in the extracts are determined. The test method of use can be a conventional method in the art, for example (but not limited to): Solexa sequencing technology, real-time PCR, RT-PCR, microarray chip, hybridization in situ, Northern blotting, isothermal rolling circle amplification, microRNA detection based on conjugated polymer and the like.

Said method of Solexa sequencing technology preferably comprises the steps of:

collecting *Lonicera japonica* tissue or soup samples;

extracting total RNA from the samples with Trizol reagent;

performing PAGE electrophoresis and recovering the RNA molecules of 17-27 nt;

enzyme-linking adaptor primers to the 3' and 5' ends of the small RNA molecules respectively; and performing cluster generation directly using purified DNA, and conducting sequencing analysis utilizing Illumina Genome Analyzer.

Real-time PCR method preferably comprises the steps of:

extracting the total RNA from samples, and obtaining cDNA samples by RNA reverse transcription reaction;

designing primers using plant microRNAs;

adding TaqMan probes or fluorescent dye to perform PCR reaction; and determining the changes of the amount of plant microRNAs in the samples.

Identification

The present invention provides a method of identifying plant functional microRNAs, wherein said plant functional microRNAs have the function of regulating non-plant target genes, said method comprising the steps of:

(1) Providing an extract of a certain plant (including medicinal plants, and fruit and vegetable plants);

(2) Determining the species or levels of the plant endogenous microRNAs in said extract; and (3) Performing alignment and analysis of the sequences of the determined plant microRNAs and non-plant target genes to identify the plant functional microRNAs having the function of regulating the non-plant target genes.

In another preferred example, said non-plant target gene includes the genes in a gene database. Preferably, said non-plant target gene includes bacterial gene, viral gene, chlamydial gene, yeast gene, and animal gene; or said non-plant target gene is a gene of a pathogen.

In another preferred example, microRNA species having an abundance in the extract of top 20 (more preferably top 10) are picked out in step (3) for alignment and analysis.

In another preferred example, plant microRNA species having a Lm/La ratio greater than or equal to 130% (more preferably greater than or equal to 150% and still more preferably greater than or equal to 200%) are picked out in step (3) for performing alignment and analysis, wherein Lm is the abundance (or level) of a certain plant microRNA in the extract, and La is the average abundance (or level) of said plant total microRNAs.

The plant functional microRNA molecules identified by said method include MIR2911.

Uses

The plant functional microRNAs or the plant extract containing said plant functional microRNAs described in the present invention have multiple uses as follows:

I. Guiding the Development or Manufacture of Functional Compositions

The active ingredients of the composition described in the present invention are said plant functional microRNAs or the plant extract containing said plant functional microRNAs, wherein, said plant functional microRNAs (such as MIR2911 and the like) have the function of regulating non-plant target genes. It can be used for (a) preparing a composition for regulating non-plant target genes; or (b) preparing a pharmaceutical for treating diseases associated with non-plant target genes, wherein said regulating includes inhibition (down-regulation) of the expression of the target gene, and promotion (up-regulation) of the expression of the target gene.

In another preferred example, said non-plant target gene includes bacterial gene, viral gene, chlamydial gene, yeast gene, and animal gene; or said non-plant target gene is a gene of a pathogen (including bacteria, viruses, and chlamydia, etc.).

In another preferred example, said diseases associated with non-plant target genes include: tumors (such as liver cancer and lung cancer), acute and chronic infectious diseases (for example, viral diseases such as viral influenza, viral hepatitis, acquired immunodeficiency syndrome, and SARS; bacterial diseases such as tuberculosis and bacterial pneumonia; and acute and chronic infectious diseases caused by pathogenic microorganisms); and other acute and chronic diseases (for example, respiratory system diseases, immune system diseases, blood and hematopoietic system diseases such as circulatory diseases including cardiovascular and cerebrovascular diseases, metabolic diseases related to endocrine system, digestive system diseases, nervous system diseases, urinary system diseases, reproductive system diseases and motor system diseases).

Compositions

The composition described in the present invention (including a pharmaceutical composition, a food composition or a health care product composition) may comprises (a) a carrier acceptable in pharmaceutics or bromatology; and (b) an active ingredient.

Preferably, said composition consists of or substantially consists of components (a) and (b).

In another preferred example, the content of component (b) accounts for 0.01-99 wt % of the total weight of the composition, more preferably 0.1-90 wt % (calculated as microRNA).

The method for preparing said composition comprises the step of mixing said plant functional microRNAs or the plant extract containing said functional microRNAs with a carrier acceptable in pharmaceutics or bromatology to form said composition.

The composition is further described with a pharmaceutical composition as an example: the pharmaceutical composition of the present invention comprises an active ingredient within the scope of a safe and effective amount and a pharmaceutically acceptable excipient or carrier. The "safe and effective amount" herein means that the amount of the active ingredient can obviously relieve pathogenic condition without causing severe side effect. Generally, a pharmaceutical composition contains 1-2000 mg active ingredient/dose, and preferably contains 10-200 mg active ingredient/dose. Alternatively, a pharmaceutical composition contains 0.01-100 micromoles of active ingredient/dose, preferably 0.1-10 micromoles of active ingredient/dose; and more preferably, said "a dose" is an oral solution.

"A carrier acceptable in pharmaceutics" means one or more compatible solid or liquid fillers or gel substances which are suitable for human use and moreover must have sufficient purity and low enough toxicity. "Compatibility" herein means that individual components in the composition can be incorporated with the compounds of the present invention and incorporated with one another without obviously reducing the drug effect of the compounds. The examples of the pharmaceutically acceptable carrier include cellulose and derivatives thereof (such as sodium carboxymethylcellulose, sodium ethyl cellulose, cellulose acetate and the like), gelatin, talc, solid lubricant (such as stearic acid, magnesium stearate), calcium sulfate, a vegetable oil (such as soybean oil, sesame oil, peanut oil, olive oil and the like), polyols (such as propylene glycol, glycerine, mannitol, sorbitol and the like), an emulsifying agent (such as Tween®), a wetting agent (such as sodium lauryl sulfate), a colorant, a flavoring agent, a stabilizing agent, an antioxidant, a preservative, pyrogen-free water and the like.

The administration mode of the composition of the present invention includes oral, respiratory tract, injection, transdermal, mucosal, or cavity administration.

The dosage form of the composition of the present invention includes a tablet, a capsule, a powder, a pill, a granule, a syrup, a solution, a suspension liquid, an emulsion, a suspension, a spray, an aerosol, a powder spray, a volatile liquid, an injection solution, a powder for injection, a topical solution, a lotion, a pour agent, a liniment, a cataplasma, a medicinal paste, a rubber paste, an ointment, a plaster, a paste, an eye drop, a nasal drop, an ophthalmic ointment, a mouth wash, a sublingual tablet, or a suppository.

Preferably, the present invention provides the use of a microRNA molecule MIR2911 or an extract containing MIR2911 for preparing a pharmaceutical for treating viral influenza. Preferably, said extract (unconcentrated or concentrated) contains 0.01-100 nM (preferably 0.1-20 nM) MIR2911.

II. Guiding the Artificial Synthesis of Plant Functional microRNAs

The plant functional microRNAs which exist in plants (particularly in plant extracts) can be identified through the method described in the present invention, which can directly guide a person skilled in the art to artificially synthesize said microRNAs so as to improve the production of said microRNAs. The synthesized plant functional microRNA molecules are mixed with a carrier acceptable in pharmaceutics or bromatology to form a composition.

The method for artificially synthesizing microRNA can be a method well known to a person skilled in the art. For example, for artificially synthesizing MIR2911, the preferable method comprises:

1. Method for chemical synthesis of MIR2911, the particular operating steps thereof comprising:

(1) Preparing monomers of methoxy phosphoramidite diisopropylamine of four deoxynucleosides (deoxyadenosine dA, deoxyguanosine dG, deoxycytidine dC, deoxythymidine dT);

(2) Initiating the protected deoxynucleosides to connect to a carrier after activation with tetrazole; and (3) Extending the nucleotide strands one nucleotide by one nucleotide on the carrier using solid phosphoramidite method to synthesize MIR2911;

2. Other synthesis method of MIR2911, the particular operating steps thereof comprising:

(1) Designing the Primers for Synthesizing MIR2911:

Two universal primers A, B are synthesized according to the template plasmid sequence of MIR2911, and 4 specific oligonucleotide primer sequences (I, II, III, IV) are designed according to the MIR2911 sequence;

(2) First Round of PCR Amplification:

PCR amplification is performed using a plasmid containing MIR2911 as template, and A and IV, III and II, I and B as primer combinations, respectively; PCR reaction conditions are: 95° C., 2 minutes for 1 cycle→95° C., 30 seconds, 55° C., 30 seconds, 72° C., 40 seconds for 24 cycles→72° C., 7 minutes; product 1, product 2, and product 3 are obtained, respectively;

(3) Second Round of PCR Amplification:

With the product 1, product 2, and product 3 obtained in the first round of PCR amplification as templates, PCR amplification is performed using A and B as primers; PCR reaction conditions are: 95° C., 2 minutes for 1 cycle→95° C., 30 seconds, 55° C., 30 seconds, 72° C., 1 minute 30 seconds for 24 cycles→72° C., 7 minutes, and PCR products are recovered via agarose gel to obtain synthesized MIR2911;

(4) Methylating the Synthesized MIR2911 to Form a Stable Methylated Product MIR2911.

III. In Vitro Non-Therapeutic Regulation of the Expression of Non-Plant Target Genes The biological material (including viruses, cells, and tissues) containing non-plant target genes (such as bacterial gene, viral gene, chlamydial gene, yeast gene, and animal gene) is cultured in the presence of the isolated plant functional microRNAs or the extract containing said plant functional microRNAs described in the present invention so as to realize the in vitro regulation of the expression of said non-plant target genes.

In another preferred example, said target gene is a gene of a pathogen (including bacteria, viruses, and chlamydia, etc.).

In another preferred example, said plant functional microRNAs are derived from the following plants: medicinal plants, fruit and vegetable plants, and ornamental plants; preferably, derived from *Lonicera japonica, Isatis tinctoria, Isatis indigotica, Baphicacanthus cusia* or *Populus diversifolia*; and more preferably, said plant functional microRNAs include MIR2911.

IV. Disease Prevention or Treatment Method

The isolated plant functional microRNAs or the extract containing said plant functional microRNAs described in the present invention or the composition described in the present invention are applied to a subject (such as a mammal or human) in need to realize the prevention or treatment of diseases associated with non-plant target genes, wherein said plant functional microRNAs have the function of regulating non-plant target genes (including bacterial gene, viral gene, chlamydial gene, yeast gene, and animal gene).

In another preferred example, said non-plant target gene is a gene of a pathogen.

Through a series of studies on plant functional microRNAs and their existing forms after entering animal body, delivery pathways, and functions, the inventors have 1. established a set of efficient and stable methods for extracting plant functional microRNAs and provided a plant extract containing plant functional microRNAs; 2. found that plant (such as *Lonicera japonica*, etc.) functional microRNAs can enter animal body through a variety of pathways (such as food intake or intravenous injection, etc.) and enrich in blood, regulate non-plant target genes, and then participate in the physiological and pathological activities of animal body (such as human); 3. formed a set of methods for identifying plant functional microRNAs, which can be used for guiding the method for selective synthesis of plant functional microRNAs, thus facilitating the faster production of the microRNAs; and also can be used for guiding the screening of medicinal materials rich in plant functional microRNAs, thus facilitating the identification between the good and bad medicinal materials; 4. formed a set of methods for guiding the manufacture of functional foods or pharmaceuticals: 4.1 said methods can be used for manufacturing compositions such as functional foods or pharmaceuticals and the like using isolated plant functional microRNAs or a plant extract containing plant functional microRNAs or the screened plants rich in functional microRNAs; 4.2 said methods comprise that plant microRNAs are extracted and plant functional microRNAs are identified, and said plant functional microRNAs are artificially synthesized, and then the artificially synthesized microRNAs are used for manufacturing functional foods or pharmaceuticals.

The main advantages of the present invention include:

1. Providing an isolated plant functional microRNA and/or an plant extract containing said plant functional microRNA and uses thereof. Said microRNA can regulate the expression of non-plant target genes, and has a variety of uses (for instance, it can be used as the criterion for the active ingredients of Chinese herbal medicines, which facilitates the development and manufacture of functional compositions, etc.).

2. Providing a composition using isolated plant functional microRNAs and/or an plant extract containing said plant functional microRNAs as active ingredients. The mechanism of action of said active ingredient is definite and the effect thereof is significant, which is helpful for discovering the scientific mechanisms of traditional Chinese medicine and is simple in manufacture method, low in cost, and suitable for mass production.

3. Providing a method for identifying plant functional microRNAs.

The present invention is further illustrated in connection with particular embodiments as follows. It should be understood that these embodiments are merely illustrative of the invention and are not intended to limit the scope of the present invention. Where the specific conditions for a experimental method are not specified in the following examples, conventional conditions are generally followed, such as the conditions described in Sambrook et al., *Molecular Cloning: A Laboratory Manual* (New York: Cold Spring Harbor Laboratory Press, 1989), or the conditions recommended by the manufacturer. All percentages and parts are by weight unless otherwise indicated.

Example 1 Detection of Plant microRNAs Stably Existing in *Lonicera japonica* Water Extract Using Solexa Sequencing Technology First of all, *Lonicera japonica* microRNAs are extracted using water extraction method. Appropriate amount (50 grams) of dried *Lonicera japonica* is taken, followed by heating same in 100° C. water bath with the water being 500 ml (the ratio of the mass of *Lonicera japonica* to the volume of water is 1:10) for 0.5 hours, and concentrating the water extract at 60° C. under reduced pressure to ¹⁄₁₀ of its original volume. The concentrated and unconcentrated *Lonicera japonica* water extracts are collected for subsequent experiments.

Afterwards, the plant microRNAs stably existing in the *Lonicera japonica* water extract prepared via the abovementioned steps is detected using Solexa sequencing technology, the loading amount for Solexa sequencing is 10 μg RNA. It is determined that the concentration of total microRNAs in the unconcentrated water extract is approximately 1 nM, and the concentration of total microRNAs in the concentrated water extract is approximately 10 nM.

Figure 1:
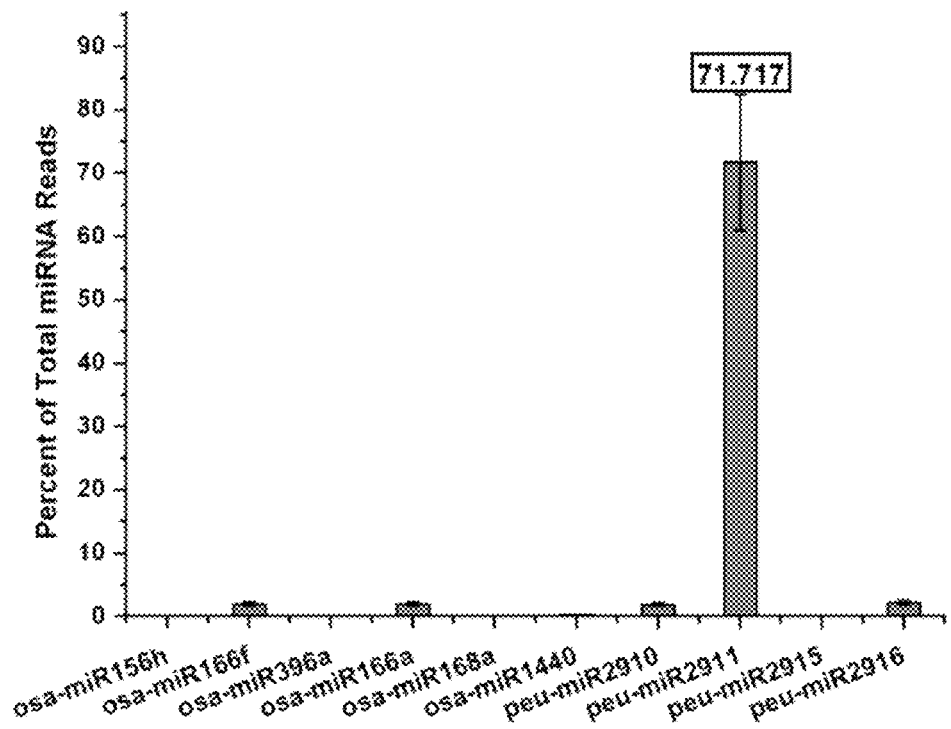
FIG. 1 shows the Solexa sequencing results of the plant microRNAs in *Lonicera japonica* water extract.

The detection results show that there are a variety of plant microRNAs stably existing in *Lonicera japonica* water extract; these can be detected include 85 types of microRNAs listed in Table 1, with their sequences detailed in Table 1. Among them, MIR156h, MIR166f, MIR396a, MIR166a, MIR168a, MIR1440, MIR2910, MIR2911, MIR2915, and MIR2916 are relatively high in content, and the content of MIR2911 is the highest. The particular results are shown in FIG. 1. The copy numbers of the other 75 types of miRNAs in Table 1 are detected in extracts of relatively low copy numbers (all of them is between 2-1000).

TABLE 1

MicroRNAs which stably exist in *Lonicera japonica* and are detectable

| | microRNA name | Corresponding sequence |
|---|---|---|
| SEQ ID NO.: 1 | MIR156h | uugacagaagauagagagcac |
| SEQ ID NO.: 2 | MIR166f | ucggaccaggcuucauucccc |
| SEQ ID NO.: 3 | MIR396a | uuccacagcuuucuugaacug |
| SEQ ID NO.: 4 | MIR166a | ucggaccaggcuucauucccc |
| SEQ ID NO.: 5 | MIR168a | ucgcuuggugcaggucgggaa |
| SEQ ID NO.: 6 | MIR1440 | ugcucaaauaccacucuccu |
| SEQ ID NO.: 7 | MIR2910 | uaguuggugggagcgauuuguc |
| SEQ ID NO.: 8 | MIR2911 | ggccggggacgggcuggga |
| SEQ ID NO.: 9 | MIR2915 | cccgucuagcucaguuggua |
| SEQ ID NO.: 10 | MIR2916 | uggggacucgaagacgaucauau |
| SEQ ID NO.: 11 | MIR818d | aaucccuuauauuaugggacgg |
| SEQ ID NO.: 12 | MIR159e | auugguuugaagggagcucca |
| SEQ ID NO.: 13 | MIR159c | auuggauugaagggagcucca |
| SEQ ID NO.: 14 | MIR156j | ugacagaagagagagagcac |
| SEQ ID NO.: 15 | MIR1432 | cucaggagaugacaccgac |
| SEQ ID NO.: 16 | MIR166k | ucggaccaggcuucauucccc |
| SEQ ID NO.: 17 | MIR167b | ugaagcugccagcaugaucua |
| SEQ ID NO.: 18 | MIR396c | uuccacagcuuucuugaacuu |
| SEQ ID NO.: 19 | MIR156e | ugacagaagagagugagcaca |
| SEQ ID NO.: 20 | MIR169k | uagccaaggaugacuugccg |
| SEQ ID NO.: 21 | MIR167c | uaagcugccagcaugaucuug |
| SEQ ID NO.: 22 | MIR160d | ugccuggcucccuguaugcca |
| SEQ ID NO.: 23 | MIR399a | ugccaaaggagaauugcccug |
| SEQ ID NO.: 24 | MIR156d | ugacagaagagagugagcac |
| SEQ ID NO.: 25 | MIR160e | ugccuggcucccuguaugcca |
| SEQ ID NO.: 26 | MIR169n | ugagccaaggaugacuugccg |
| SEQ ID NO.: 27 | MIR166l | ucggaccaggcuucaaucccu |
| SEQ ID NO.: 28 | MIR159f | uuuggauugaagggagcucug |
| SEQ ID NO.: 29 | MIR166c | ucggaccaggcuucauucccc |
| SEQ ID NO.: 30 | MIR159b | uuuggauugaagggagcucug |
| SEQ ID NO.: 31 | MIR166j | ucggaucaggcuucauuccuc |
| SEQ ID NO.: 32 | MIR167i | ugaagcugccagcaugaucug |
| SEQ ID NO.: 33 | MIR169c | cagccaaggaugacuugccgg |
| SEQ ID NO.: 34 | MIR164c | uggagaagcagggcacgugca |
| SEQ ID NO.: 35 | MIR167j | ugaagcugccagcaugaucua |
| SEQ ID NO.: 36 | MIR167g | ugaagcugccagcaugaucug |
| SEQ ID NO.: 37 | MIR160c | ugccuggcucccuguaugcca |
| SEQ ID NO.: 38 | MIR399e | ugccaaaggagauuugcccgg |
| SEQ ID NO.: 39 | MIR399b | ugccaaaggagauuugcccgg |
| SEQ ID NO.: 40 | MIR529b | agaagagagagaguacagcuu |
| SEQ ID NO.: 41 | MIR164e | uggagaagcaggacacgugag |
| SEQ ID NO.: 42 | MIR166d | ucggaccaggcuucauucccc |
| SEQ ID NO.: 43 | MIR166h | ucggaccaggcuucauucccc |
| SEQ ID NO.: 44 | MIR164b | uggagaagcagggcacgugca |
| SEQ ID NO.: 45 | MIR156f | ugacagaagagagugagcac |
| SEQ ID NO.: 46 | MIR164a | uggagaagcagggcacgugca |
| SEQ ID NO.: 47 | MIR169l | uagccaaggaugacuugccug |
| SEQ ID NO.: 48 | MIR166m | ucggaccaggcuucauucccu |
| SEQ ID NO.: 49 | MIR164f | uggagaagcagggcacgugcu |
| SEQ ID NO.: 50 | MIR156k | ugacagaagagagggagcac |
| SEQ ID NO.: 51 | MIR166g | ucggaccaggcuucauucccc |
| SEQ ID NO.: 52 | MIR166b | ucggaccaggcuucauucccc |
| SEQ ID NO.: 53 | MIR160b | ugccuggcucccuguaugcca |
| SEQ ID NO.: 54 | MIR166e | ucggaccaggcuucauucccc |
| SEQ ID NO.: 55 | MIR159d | cuuggauugaagggagcuccu |
| SEQ ID NO.: 56 | MIR818e | aaucccuuauauuaugggacgg |
| SEQ ID NO.: 57 | MIR172a | agaaucuugaugaugcugcau |
| SEQ ID NO.: 58 | MIR156b | ugacagaagagagugagcac |
| SEQ ID NO.: 59 | MIR399g | ugccaaaggagauuugcccag |
| SEQ ID NO.: 60 | MIR169b | cagccaaggaugacuugccgg |
| SEQ ID NO.: 61 | MIR399f | ugccaaaggagauuugcccag |
| SEQ ID NO.: 62 | MIR167a | ugaagcugccagcaugaucua |

TABLE 1-continued

MicroRNAs which stably exist in *Lonicera japonica* and are detectable

| | microRNA name | Corresponding sequence |
|---|---|---|
| SEQ ID NO.: 63 | MIR394 | uuggcauucuguccaccucc |
| SEQ ID NO.: 64 | MIR156a | ugacagaagagagugagcac |
| SEQ ID NO.: 65 | MIR166i | ucggaucaggcuucauuccuc |
| SEQ ID NO.: 66 | MIR167f | ugaagcugccagcaugaucug |
| SEQ ID NO.: 67 | MIR319a | agcugccgaaucauccauuca |
| SEQ ID NO.: 68 | MIR156g | ugacagaagagagugagcac |
| SEQ ID NO.: 69 | MIR166n | ucggaccaggcuucauucccc |
| SEQ ID NO.: 70 | MIR399c | ugccaaaggagaauugcccug |
| SEQ ID NO.: 71 | MIR160a | ugccuggcucccuguaugcca |
| SEQ ID NO.: 72 | MIR159a.1 | uuuggauugaagggagcucug |
| SEQ ID NO.: 73 | MIR156c | ugacagaagagagugagcac |
| SEQ ID NO.: 74 | MIR319b | uuggacugaagggugcuccc |
| SEQ ID NO.: 75 | MIR169o | uagccaagaaugacuugccua |
| SEQ ID NO.: 76 | MIR167h | ugaagcugccagcaugaucug |
| SEQ ID NO.: 77 | MIR156i | ugacagaagagagugagcac |
| SEQ ID NO.: 78 | MIR167d | ugaagcugccagcaugaucug |
| SEQ ID NO.: 79 | MIR169a | cagccaaggaugacuugccga |
| SEQ ID NO.: 80 | MIR172d | agaaucuugaugaugcugcau |
| SEQ ID NO.: 81 | MIR818b | aaucccuuauauuaugggacgg |
| SEQ ID NO.: 82 | MIR164d | uggagaagcagggcacgugcu |
| SEQ ID NO.: 83 | MIR167e | ugaagcugccagcaugaucug |
| SEQ ID NO.: 84 | MIR396b | uuccacagcuuucuugaacug |
| SEQ ID NO.: 85 | MIR2914 | uaugguggugacgggugacggag |

Example 2 Detection of *Lonicera japonica* microRNAs Entering Animal Body Via Ingestion and Existing Stably Using Real-Time PCR Method This example demonstrated that a *Lonicera japonica* microRNAs can enter animal body via ingestion and exists stably.

*Lonicera japonica* water extract (the concentrated water extract prepared in example 1) is administered intragastrically to mice, and the expression levels of *Lonicera japonica* microRNAs in sera, livers, and lungs are detected.

The particular steps are: firstly, the mice are starved for 12 hours, then the concentrated *Lonicera japonica* water extract is administered in 10 ml per kg of body weight of mice intragastrically to mice, and the expression levels of *Lonicera japonica* microRNA MIR2911 in sera, livers, and lungs in mice at 0 h (0 hours), 2 h (2 hours), 4 h (4 hours), 6 h (6 hours) and the like are detected using real-time PCR.

The primer sequences for detecting MIR2911 by real-time PCR are:

forward primer:
(SEQ ID NO.: 86)
ACACTCCAGCTGGGGGCCGGGGGACGGG;

reverse primer:
(SEQ ID NO.: 87)
CTCAACTGGTGTCGTGGAGTCGGCAATTCAGTTGAGTCCCAG CC;

Probe sequence:
(SEQ ID NO.: 88)
TCCCAGCCCGTCCCCCGGCC.

Figure 2A:
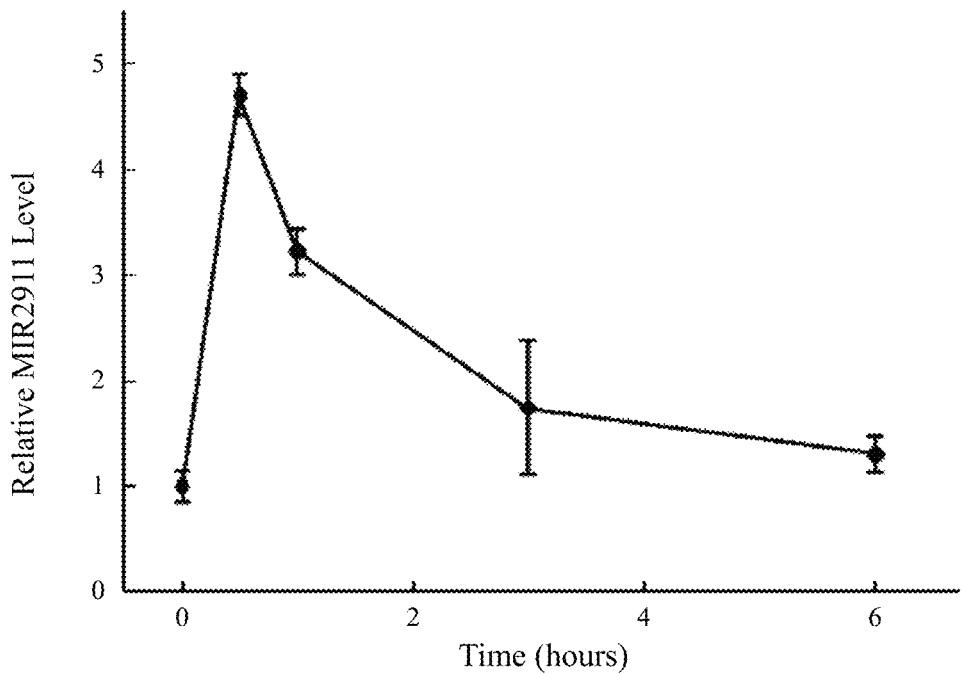
FIG. 2A is the real-time PCR results of the expression amounts of *Lonicera japonica* microRNAs in mice sera at different time points after intragastrical administration of *Lonicera japonica* water extract. The time points for detection are 0 h (0 hour), 2 h (2 hour), 4 h (4 hour), and 6 h (6 hour).
Figure 2B:
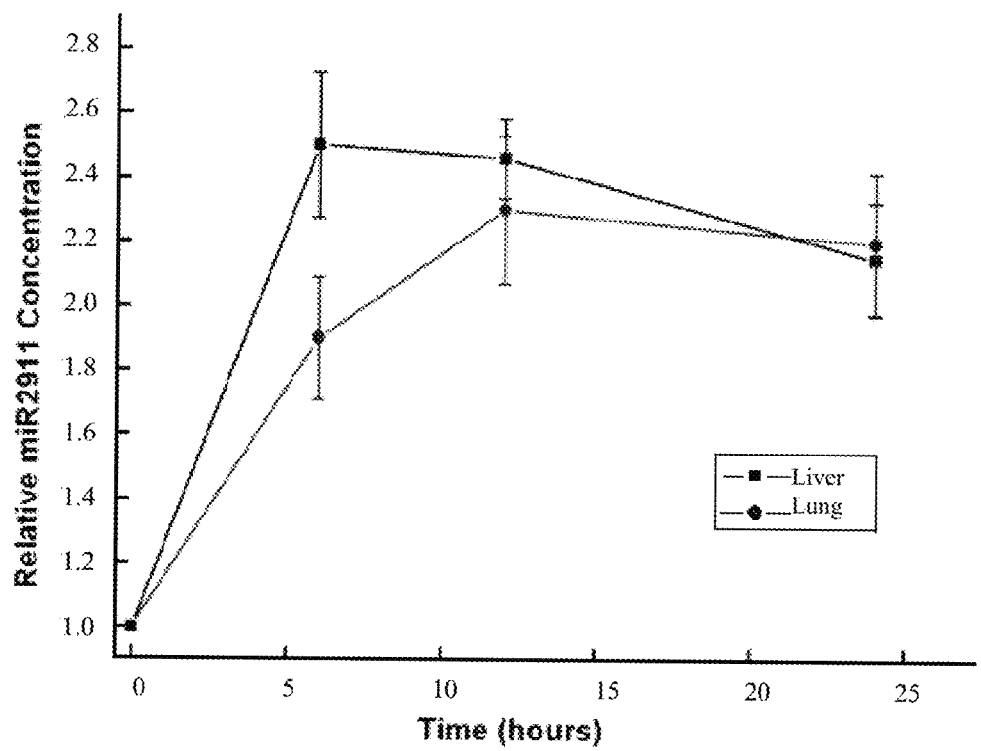
FIG. 2B is the real-time PCR results of the expression amounts of *Lonicera japonica* microRNAs in mice liver and lung at different time points after intragastrical administration of *Lonicera japonica* water extract. The time points for detection are 0 h (0 hour), 5 h (5 hour), 10 h (10 hour), 15 h (15 hour), 20 h (20 hour), and 25 h (25 hour).

The particular results are shown in FIG. 2A and FIG. 2B.

FIG. 2A is the real-time PCR results of the expression amounts of *Lonicera japonica* microRNAs in mice sera at different time points after intragastrical administration of *Lonicera japonica* water extract. It can be seen from the results that the content of MIR2911 in mice sera increases significantly after intragastrical administration of *Lonicera japonica* water extract. The content of MIR2911 in sera reaches the maximum value 1.5 hours after intragastrically administering the *Lonicera japonica* water extract, and the content of MIR2911 in sera decreases to the original level after 6 hours.

FIG. 2B is the real-time PCR results of the expression amounts of *Lonicera japonica* microRNAs in liver and lung at different time points after intragastrically administering the *Lonicera japonica* water extract to mice. It can be seen from the results that the expression levels of MIR2911 in liver and lung increase after intragastrically administering the *Lonicera japonica* water extract to the mice. The expression level of MIR2911 in liver reaches the maximum value 6 hours after intragastrically administering the *Lonicera japonica* water extract to mice, and the expression level of MIR2911 in lung reaches the maximum value 12 hours after intragastrically administering the *Lonicera japonica* water extract.

The results show that *Lonicera japonica* microRNAs can enter animal body via ingestion and exist stably.

Example 3 *Lonicera japonica* microRNAs can Regulate Physiological and Pathological Activities This example demonstrates that *Lonicera japonica* microRNAs can regulate the physiological and pathological activities in animal body.

Figure 3:
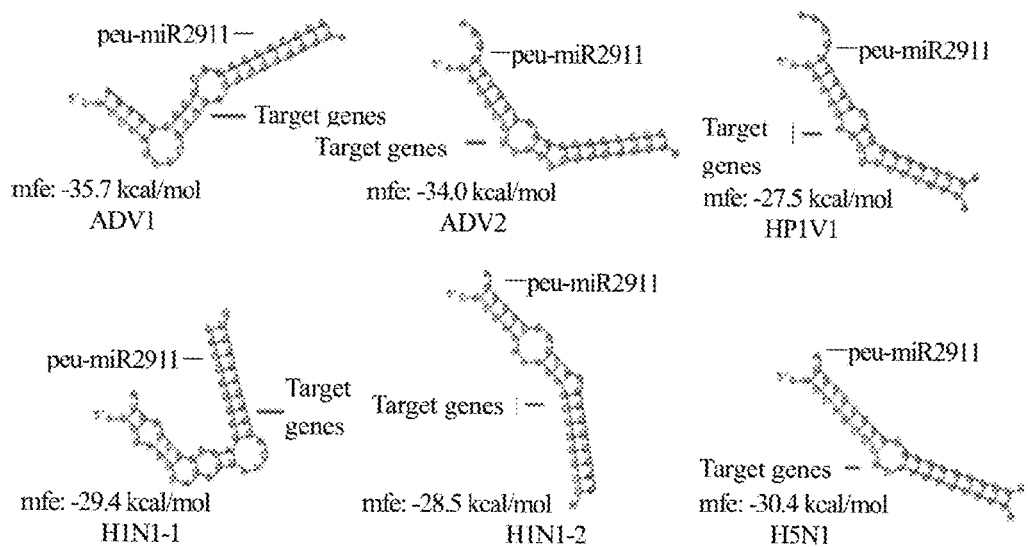
FIG. 3 shows the sequence analysis results of the predicted target genes of MIR2911. mfe represents the minimal folding free energy of the candidate target gene, the greater the absolute value of mfe, the higher the matching rate of the candidate target gene with Peu-MIR2911 sequence.

3.1 Prediction of Target Genes of *Lonicera japonica* microRNAs Using Bioinformatics Multiple target genes in genomes of infectious respiratory disease viruses are predicted to be matched with MIR2911 sequence using bioinformatics. The particular results are shown in FIG. 3. FIG. 3 is the sequence analysis results of the predicted target genes of MIR2911. mfe represents the minimal folding free energy of the candidate target gene, the greater the absolute value of mfe, the higher matching rate of the candidate target gene with Peu-MIR2911 sequence. The results show that ADV genes, HPIV1 gene, H1N1 genes, and H5N1 gene are potential target genes of *Lonicera japonica* microRNAs. The sequences of ADV genes, HPIV1 gene, H1N1 genes, and H5N1 gene are shown in Table 2.

TABLE 2

Viral gene sequences shown in FIGS. 3 and 15

| | Viral genes | Corresponding sequence |
|---|---|---|
| SEQ ID NO.: 95 | ADV1 | atgtccaagcgcaaaatcaaagaagagatgctccaggtcatc<br>gcgccggagatctatggcccccgaagaaggaagagcagg<br>attacaagccccgaaagctaaagcgggtcaaaaagaaaaag<br>aaagatgatgatgatgaacttgacgacgaggtggaactgctg<br>cacgctaccgcgcccaggcgacgggtacagtggaaaggtc<br>gacgcgtaaaacgtgttttgcgacccggcaccaccgtagtctt<br>tacgcccggtgagcgctccacccgcacctacaagcgcgtgta<br>tgatgaggtgtacggcgacgaggacctgcttgagcaggcca<br>acgagcgcctcggggagtttgcctacggaaagcggcataag<br>gacatgctggcgttgccgctggacgagggcaacccaacacc<br>tagcctaaagcccgtaacactgcagcaggtgctgcccgcgct<br>tgcaccgtccgaagaaaagcgcggcctaaagcgcgagtctg<br>gtgacttggcacccaccgtgcagctgatggtacccaagcgcc<br>agcgactggaagatgtcttggaaaaaatgaccgtggaacctg<br>ggctggagcccgaggtccgcgtgcggccaatcaagcaggt<br>ggcgccgggactgggcgtgcagaccgtggacgttcagatac<br>ccactaccagtagcaccagtattgccaccgccacagagggc<br>atggagacacaaacgtccccggttgcctcagcggtggcggat<br>gccgcggtgcaggcggtcgctgcggccgcgtccaagacctc<br>tacggaggtgcaaacggacccgtggatgtttcgcgtttcagcc<br>cccggcgcccgcgccgttcgaggaagtacggcggccgcca<br>gcgcgctactgcccgaatatgccctacatccttccattgcgcct<br>accccggctatcgtggctacacctaccgccccagaagacg<br>agcaactacccgacgccgaaccaccactggaacccgccgc<br>cgccgtcgccgtcgccagcccgtgctggccccgatttccgtg<br>cgcagggtggctcgcgaaggaggcaggaccctggtgctgc<br>caacagcgcgctaccaccccagcatcgttaa |
| SEQ ID NO.: 96 | ADV2 | atgactacgtccggcgttccatttggcatgacactacgaccaa<br>cacgatctcggttgtctcggcgcactccgtacagtagggatcg<br>tctacctcctttttgagacagaaacccgcgctaccatactggag<br>gatcatccgctgctgcccgaatgtaacactttgacaatgcaca<br>acgcgtggacttctccttcgccgcccgttaagcaaccgcaagt<br>tggacagcagcctgtggctcagcagctggacagcgacatga<br>acttaagtgagctgcccggggagtttattaatatcactgatgag<br>cgtttggctcgacaggaaaccgtgtggaatataacacctaaga<br>atatgtctgttacccatgatatgatgcttttttaaggccagccggg<br>gagaaaggactgtgtactctgtgtgttgggagggaggtggca<br>ggttgaatactagggttctgtga |
| SEQ ID NO.: 97 | HIPV1 | atggatacaacaggagtcaactcagaattcctcagacatcttata<br>tccagaatgtcacttgaactctccgattgtaaaaagcaagattg<br>ctcaacttcacgttttgctagatatcaatcaaccctatgatttaaa<br>agataacagtataataaatatcaccaaatacaaaatcagaaatg<br>gaggtttatcgccccggcagatcaaaatcagatcgctaggca<br>aaatccttaaacaagaaattaaggatattgatcgttacacttttga<br>acctttatccgattttctcattagagttactcagactggatatccca<br>gaaatatgtgacaaaataagatccattttttttcagtctctgatagat<br>taataagagaactatcatctggatttcaagaattgtggttaaatat<br>tcttagacaattaggctgtgttgaagggaaagagggatttgact<br>cattaaaggatgtagatatcatcccagatataactgataaatata<br>ataaaaacacatggtatcgcccattcttaacatggtttagcatca<br>aatatgatatgagatggatgcaaaagaataagtcggggaacc<br>atttagatgtctcaaattctcacaattttcttgactgtaaatcatata<br>ttttgattatatatagagatttagtgataataatgataaatttaaaat<br>taaccggttatgtccttacacctgaattagtattaatgtattgtgat<br>gttgtcgaaggaagatggaatatgtcttcagctggacgactcg<br>ataaaaggtcatcaaaaataacatgtaaggggaagaattatg<br>ggagcttatcgactctttatttcccaatcttggtgaggatgtatat<br>aatattatatcactactagaaccttttatcacttgctttaatacagtt<br>ggatgaccctgtaactaatttaaaaggagctttcatgagacatg<br>ttttgactgagctacatacaattttaataaaagataatatatacac<br>agattcagaagcagacagcatatggaatcattgataaagattt<br>tcagagagacatcaattgatgaaaaagcagaaattttctcctttt<br>ttagaacgtttggacatcctagcttagaagcaataactgctgcc<br>gataaagtaaggacacatatgtattcctccaaaaaaatcatact<br>aaagacactatatgagtgtcatgcaatcttctgtgcaattataat<br>aaacggatatagagaaagacacggtggtcaatggccgccat<br>gcgaattccccaatcatgtatgtcttgaactcaagaatgcacaa<br>ggatccaactctgcaatttcgtatgaatgtgccgtagacaattat<br>agtagttttataggatttaaattttttaaaattttattgagcctcaatta<br>gatgaagatttgacaatttatatgaaggataaggctctatcacct<br>aggaaagcagcatgggattcagtatatcccgacagtaatttata<br>ttacaaagtccctgaatcagaagagactcgtaggttaatcgag<br>gttttttataaatgataataattttaaccctgcggatattattaattat<br>gtagagtcaggagaatggttaaatgacgatagcttcaacatat |

TABLE 2-continued

Viral gene sequences shown in FIGS. 3 and 15

| Viral genes | Corresponding sequence |
|---|---|
| | cttacagtctcaaagaaaaagaaattaaacaagagggtcgact
cttttgccaagatgacatataagatgagagcagtccaggtatta
gcagaaacactactagcaaaaggagtaggtgagttattcagtg
aaaatgggatggtaaagggagaaattgacctactaaagagac
tgactacattatctgtctcaggtgttccaagatccaactcagttta
caataatcccatattacatgagaaattgatcaaaaatatgaataa
gtgcaattcaaatgggtattgggatgaaagaaagaaatctaaa
aatgaattcaaagctgcagactcatcaaccgaggggtatgag
actctgagctgttttttaaccaccgatttgaaaaaatactgtctca
actgagatttgaaagtacagcgttgttcggtcaaagatgtaat
gagatattcgggtttaaaactttcttaactggatgcaccctattc
tagaaaaaagtacaatttatgtaggagatccttactgtccagtac
ctgatagaatgcacaaagaactccaagatcatgatgataccgg
aatctttatccataatccaagaggggaatagagggttattgcc
agaaattatggacactaatctctattagtgcaatccatcttgcag
ctgttaaagttggtgtcagagtgtcagcaatggtacaaggaga
caatcaagctatagcagtgacatccagagttcctgtcacacaa
acctataagcaaaaaaagactcacgtctatgaagaaatcacaa
gatatttcggtgccttgagagaagttatgtttgatattggacatg
aattaaaattaaatgagaccattataagtagcaaaatgtttgtata
cagcaaacggatatattatgatgggaaaatcctcccacagtgc
ctcaaagctttaacaagatgtgtattttggtcagagactcttgta
gatgaaaacaggtcagcatgctcaaacattgcaacatctatag
ccaaagctattgagaatggatattcacctatcttaggctattgtat
tgctcttttaaaacttgccaacaggtatgtatatcattaggaatg
accattaatcctactattacgtcaactatcaaagatcaatatttta
aagggaaaaattggttaagatgtgcaatattgatcccagctaac
ataggagggttcaactatatgtctacagctagatgttttgtcaga
aatataggtgatccagcagttgcagctctagcagacttaaaga
gattcatcaaagcaggtctgttagataaacaggtattatatcgtg
tgatgaatcaagaaccaggagactcaagcttcttagattgggc
atcagacccttattcatgcaatctcccacactcacaaagtataa
caactataatcaaaaatgtaacagctagatcagtattgcaggaa
tcacctaatcctctcctatcaggtctcttttcagaatcaagtagtg
aagaagatctcaacttagcatcattttttgatggataggaaagcc
atattgcccagagtagctcacgagatcttagataactcacttac
aggtgtaagagaagctatagccgggatgcttgatacaacgaa
atctctagtaagagctagtgtcaggagaggaggattatcatata
gtatcttaagaagacttataaattatgatctattacaatatgagac
cttaacaaggacactcagaaaaccggttaaggataatatagaa
tatgagtatatgtgttcagtagaattggcaataggattgaggca
aaaaatgtggtttcatctaacttatggaagaccaatccacggttt
agaaactccagacccgttagaattattaagaggatcatttattga
aggctcagaaatatgtaaattttgtagatcagaagggaataacc
ctatgtatacttggttctatcttcctgacaacatcgacttagatac
acttagcaatggaagtcctgccatacgtatcccttatttttggttct
gctactgatgaaagatcagaggctcaactaggttatgttaaga
acttaagcaagccggcaaaagcagcaataagaatcgcaatg
gtttacacttgggcttatggaactgatgaaatatcatggatgga
agcagcacttatagctcaaaccagggctaacttaagtttagag
aatttgaagttactcaccccctgtatcgacttctacaaatttgtccc
acagattgagagatactgctacacagatgaaattttcaagtgct
actttagttcgagcgagtcgatttattaccatatctaatgataatat
ggcattaaaagaggcaggagagtctaaagatactaatttagttt
atcaacaaattatgttaaccggattgagcttatttgaattcaatat
gaggtataaacaaggatcattatctaaacctatgatattacactt
acatttgaataataaatgctgtatcatagaatctcctcaagaattg
aatattcctcctagatctacattggacttagagatcactcaggaa
aataacaagttaatctatgatcctgatcctctcaaggacatagat
ctagagttatttagtaaggttagggatgtagtacacacaattgat
atgaattattggtctgatgatgaaataattagagcaactagtatat
gtacagctatgactattgcagacacaatgtctcaattagataga
gacaatcttaaagaaatgatagcactgataaatgatgatgatat
aaatagtttaatcaccgaatttatggttattgatataccttattttg
ttccactttcgggggtattctaatcaatcaatttgcatattcacttt
acgggttaaacgtcagagggagggatgaaatatgggatat
gtgatacgcataattaaagacacatccatgcagtcctaaaagt
actgtccaatgcattatccacatcctaaaatattcaaacgattctg
ggatgcaggagttgtagagcctgtttatggacctaacttgtcca
atcaagacaagatactgttagccatttcagtatgtgaatactctg
ttgacctcttcatgcgtgattggcaagagggcataccgcttgaa
atatttatttgtgataacgacccaaatatagcagaaatgagaaa
actttcattttttagctagacatctagcatacttgtgtagtttggcag
agatagctaaagagggaccaaaattggaatctatgacatctct
cgaacgactcgaatcattgaaagagtatctagaacttactttttt
agacgatcctatattaagatatagtcaattgacaggcttagttatt |

TABLE 2-continued

Viral gene sequences shown in FIGS. 3 and 15

| Viral genes | Corresponding sequence |
|---|---|
| | aagatattccdtcaacgttaacttacatcaggaaatcttcaatta
aggtgttgagagtaagaggtatagggataccagaagtcttag
aggactgggatcctgatgccgatagtatgctactagataatata
actgctgaggttcaacacaatatacctttaaagaagaacgaaa
gaactcccttctgggggttaagggtatcaaaatcacaagttctg
cgacttagaggttatgaagagataaaaagggaagaaagagg
aagatcaggtgtaggattaactctacctttgatgggcgatattt
atcacaccaattgagacttttcgggattaatagcaccagttgttt
gaaagcattggaacttacctatttactgaatcctctagtcaataa
ggataaagatagattatatctcggagaaggtgcaggtgcaatg
ctgtcttgttatgatgctacattaggaccctgcatgaactattata
attcaggtgttaattcttgtgatctcaacggacaaagagaattaa
atatttatccttcagaagtggcactggtagggaagaaattgaat
aatgtcacgagtttatgtcaaagagttaaggttttattcaatggg
aatcctggatcaacttggatagggaatgatgaatgtgaaacac
taatctggaatgaattacagaataattcaatagggtttattcattg
tgacatggaaggtggagaacacaaatgtgatcaggtggtctta
catgaacattatagtgtgatcaggattgcataccttgttggggat
aaggacgttatcttagtaagcaaaattgcaccaagattaggtac
agactggacaaaacaattaagtttgtatttaagatactggagag
atgtcagcttaatagtgttgaaaacatctaacccagcctctaca
gaaatgtatctgatcaaaagatcctaaatctgatattatagag
gatagtaatacagtattggcaaaccttcttccattatctaaagag
gatagtattaagatagaaaatggattctagttgagaaagccaa
agttcatgattggatagttagagaattaaaggaagggagtgca
tcgtcaggtatgctaagaccttaccatcaagcattacaaatcttc
ggatttgagcctaatttaaacaaattatgtagagatttcttatctac
actaaatatagtagacacaaaaaattgtattatcacatttgatag
agtattaagagatacaatctttgagtggactcggataaaagac
gcagataagaagctaagacttacaggtaaatatgatctatatcc
tcttagagattcaggtaagttaaaagttatttctagaaggcttgta
atatcttggatagcattgtctatgtctacaagactagtaacaggg
tcatttccagacattaaatttgaatcaagactccaattaggtatag
tatcaatatcctctcgtgaaatcaaaaatcttagggttatatcaaa
gattgtcattgacaaatttgaagatattatacatagtgtgacctat
aggttcttgactaaagaaataaaaatattgatgaaaattttggga
gcagtcaaattatttggggcaagacagagcacatctgctgata
tcactaatatcgatacatcggactccatacaatga |
| SEQ ID NO.: 98    H1N1-1 | atggagagaataaaagaactaagagatctaatgtcacaatccc
gcacccgcgagatactcactaagaccactgtggaccatatgg
ccataatcaaaaaatacacatcaggaaggcaagagaagaac
cccgcactcaggatgaagtggatgatggcaatgaaatatcca
attacagcagacaagagaataatggaaatgattcctgagagg
aacgaacaggggcaaaccctctggagtaaaacaaatgatgc
cggctcagaccgagtgatggtatcacctctggccgtaacgtg
gtggaataggaatggaccaacaacaagcacagttcactatcc
aaaggtatataaaacttatttcgaaaaagtagaaaggttaaaac
atgggaccttggccccgtccacttcagaaatcaagttaaaata
agaaggagagtcgacattaaccctggccacgcagatctcagt
gccaaggaggcgcaggatgtgatcatggaagttgtcttccca
aatgaagtaggagctagaatactaacatcggagtcacagctg
acaataacaaaggagaagaaagaagagctccaggattgtaa
aattgccccctgatggtagcatacatgctagaaagagagttg
gtccgcaaaacgaggttcctaccagtggctggtggtggaacaagc
agtgtctatattgaagtgctgcatttaacccaaggaacatgctg
ggagcaaatgtacactccaggaggggaggtgagaaatgatg
atattgaccaaagtttgattatcgctgccaggaacatagtaaga
agagcaacggtatcggcagacccattagcatctctgttggaaa
tgtgccacagcacgcagattggaggaataaggatggtggac
atccttaggcagaatccaacagaggaacaagccgtggacata
tgcaaggcagcaatgggattgaggattagctcatctttcagctt
cggcggattcactttcaaaagaacaagcggatcgtcagtcaa
gaaagaagaagaagtgcttacaggcaaccttcaaacactgaa
aataagagtgcatgaggggtatgaagaattcacaatggttgg
gagaaagcaacggccattctcagaaaggcaaccagaagat
tgatccagctaatagtaagtgggagagatgagcagtcaattgc
tgaggcaataattgtggccatggtatttcacaagaggattgca
tgatcaaagcagtccgaggcgatctgaactttgtcaataggc
aaaccagcgactgaatcccatgcatcaactcttgagacatttcc
aaaaagatgcaaaagtgcttttccagaactgggaattgaacc
catcgacaatgtaatgggaatgatcggaatattacccgatatga
ccccaagcactgagatgtcgctgagggggataagagtcagc
aaaatgggagtagatgagtactccagcacggagagagtggt
ggtgagcattgaccgattttgagggttcgggatcaacgggg
gaacgtactattgtctcccgaagaagtcagtgagacacaagg |

TABLE 2-continued

Viral gene sequences shown in FIGS. 3 and 15

| Viral genes | Corresponding sequence |
|---|---|
| | aacagagaagctgacaataacttattcgtcatcaatgatgtggg<br>agatcaacggtcctgagtcggtgctggtcaacacttatcagtg<br>gatcattaggaactgggaaactgtgaaaatccaatggtcacaa<br>gatcccacaatgttatacaataagatggaattcgaaccatttca<br>gtcccttgtccctaaagcggccagaagtcaatacagcggattc<br>gtgagaacactgttccaacagatgcgagatgtgcttggaacat<br>ttgacactgttcaaataataaaacttctccctttgctgctgctcc<br>accagagcagagtaggatgcaattctcctcactgactgtgaat<br>gtgagaggatcaggaatgaggatactggtaagaggcaattct<br>ccagtgttcaattacaacaaagccaccaagaggcttacagttct<br>tgggaaagatgcaggtgcattgaccgaagatcctgatgaagg<br>cacagctggagtggaatctgctgtcctgagaggattcctcattt<br>tgggcaaagaagacaagagatatggcccagcattaagtatca<br>atgaattgagcaatcttgcaaaaggagagaaggctaatgtgtt<br>aattgggcaaggagacgtagtgttggtaatgaaacggaaacg<br>ggactctagcatacttactgacagccagacagcgaccaaaag<br>gattcggatggccatcaattag |
| SEQ ID NO.: 99    H1N1-2 | atggatgtcaatccgacattacttttcttaaaagtgccagcacaa<br>aatgctataagcacaacttttccttatactggtgaccctccttaca<br>gccatgggacaggaacagggtacaccatggatacagtcaac<br>aggacacaccagtactcagaaagaggaagatggacaaaaaa<br>taccgaaacgggagcaccgcaacttaacccaattgatggtcc<br>cttaccggaagacaatgaaccaagtggctatgcccaaacaga<br>ttgtgtattagaagcaatggctttccttgaagaatcccatcccgg<br>tatctttgaaaactcttgtattgaaacaatggaggttgttcaacaa<br>acaagggtggacaaactgacacaaggcagacagacctatga<br>ctggactctaaataggaaccagcctgctgccacagcattggc<br>aaacactatagaagtattcagatcaaacggcctcatagcaaat<br>gaatctggaaggctaatagacttccttaaagatgtaatggagtc<br>gatggacagaggcgaagtagaggtcacaactcattttcaaag<br>aaagaggagagtgagagacaatgtaactaaaaaaatggtga<br>cccaaagaacaataggcaaaaagaaacataaattagacaaaa<br>gaagttacctaattagggcattaaccctgaacacaatgaccaa<br>agatgctgagaggggaaactaaaacgcagagcaattgcaa<br>ccccaggaatgcaaataaggggtttgtatactttgttgagaca<br>ctggcaagaagcatatgtgaaaagcttgaacaatcaggattgc<br>cagttggaggaaatgagaagaaagcaaagttagcaaatgttg<br>taaggaagatgatgaccaactcccaggacactgaaatttcttc<br>accataaccggagacaacacaaaatggaacgaaaatcaaaa<br>ccctagaatgttcttggccatgatcacatatataaccaaaaatca<br>gcctgaatggttcagaaatattctaagtattgctccaataatgttt<br>tcaaacaagatggcgagactaggtaaggggtacatgtttgaa<br>agcaagagtatgaaactgagaactcaaatacctgcagagatg<br>ctagccaacatagacttgaaatatttcaatgattcaactaaaaag<br>aaaattgaaaaaatccgaccattattaatagatggaactgcatc<br>attgagtcctggaatgatgatgggcatgttcaatatgttgagca<br>ccgtattgggcgtctccattctgaatcttgggcaaaagagatac<br>accaagactacttactggtgggatggtcttcaatcgtctgatgat<br>tttgctttaattgtgaacgcacccaactatgcaggaattcaagct<br>ggagttgacaggttttatcgaacctgtaagctgctcggaattaa<br>tatgagcaaaaagaagtcttacataaacagaacaggtaccttt<br>gaattcacgagcttttctatcgtcatgggttgttgccaatttca<br>gcatggagcttcctagttttggggtgtctggggtcaatgaatct<br>gcagacatgagtattggagtcactgtcatcaaaaacaatatgat<br>aaacaatgaccttggcccagcaactgctcaaatggcccttcag<br>ttatttataaaagattacaggtacacttatcgatgccaccgagt<br>gacacacaaatacaaacccgaagatcatttgagataaagaaa<br>ctatgggaccaaacccgctcaaaagctggactgttggtctctg<br>atggaggcccccaatttgtataacattagaaatctccatattcctg<br>aagtttgcttgaaatgggagttgatggatgaggattaccaggg<br>gcgtttatgcaacccattaaacccgtttgtcagccacaaagag<br>attgaatcagtgaacagtgcagtgatgatgccggcacatggtc<br>cagccaaaaatatggagtatgacgctgttgcaacaacacactc<br>ctgggtccccaaaagaaatcgatccattttgaacacgagccaa<br>aggggatacttgaagatgagcaaatgtatcagaggtgctgc<br>aattatttgaaaaattcttcccaagtagctcatacagaagacca<br>gttggaatatccagtatggtagaggctatggtctcaagagccc<br>gaattgatgcacggattgatttcgaatctggaaggataaagaa<br>agaggaatttgctgagatcatgaagatctgttccaccattgaag<br>acctcagacggcaaaaatga |
| SEQ ID NO.: 100    H3N2 | atgaagactatcattgctttgagctacattttctgtctggttctcg<br>gccaagattttccaggaaatgacaacagcacagcaacgctgt<br>gcctgggacatcatgcggtgccaaacggaacactagtgaaa<br>acaatcacaaatgatcagattgaagtgactaatgctactgagct |

TABLE 2-continued

Viral gene sequences shown in FIGS. 3 and 15

| Viral genes | Corresponding sequence |
|---|---|
| | ggttcagagttcctcaacggggaaaatatgcaacaatcctcat
cgaatccttgatggaatagactgcacactgatagatgctctatt
gggggaccctcattgtgatggctttcaaaatgagacatgggac
cttttcgttgaacgcagcaaagctttcagcaactgttacccttat
gatgtgccagattatgcctcccttaggtcactagttgcctcgtca
ggcactctggagtttatcaatgaaggcttcacttggactggggt
cactcagaatggggaagcaatgcttgcaaaaggggacctg
ataacggttttttcagtagactgaactggttgtacaaatcaggaa
gcacatatccagtgctgaacgtgactatgccaaacaatgacaa
ttttgacaaactatacatttgggggggttcaccacccgagcacg
gaccaagaacaaaccagcctatatgttcaagcatcagggaga
gtcacagtctctaccaagagaagccagcaaactataatcccg
aatatcgggtctagaccctgggtaaggggtctgtctagtagaa
taagcatctattggacaatagttaaaccaggagacatactggta
attaatagtaatgggaacctaattgctcctcggggttatttcaaa
atgcgcactgggaaaagctcaataatgaggtcagatgcacct
attggcacctgcatttctgaatgcatcactccaaatggaagcatt
cccaatgacaagccctttcaaaacgtaaacaagatcacatatg
gagcatgtcccaagtatgttaagcaaaacacccctgaagttggc
aacagggatgcgaaatgtaccagagaaacaaactagaggcc
tattcggcgcaatagcaggttcatagaaaatggttgggaggg
aatgatagacggttggtacggtttcaggcatcaaaattctgag
ggcacaggacaagcagcagatcttaaaagcactcaagcagc
catcgaccaaatcaatgggaaactgaataggtaatcgagaa
gacgaacgagaaattccatcaaatcgaaaaggaattctcaga
agtagaaggagaattcaggacctcgagaaatacgttgaaga
cactaaaatagatctctggtcttacaatgcggagcttcttgtcgc
tctggagaaccaacatacaattgatctgactgactcggaaatg
aacaaactgtttgaaaaaacaaggaggcaactgagggaaaat
gctgaggacatgggcaatggttgcttcaaaatataccacaaat
gtgacaatgcttgcatagggtcaatcagaaatgggacttatga
ccatgatgtatacagagacgaagcattaaacaaccggtttcag
atcaaaggtgttgaactgaagtcaggatacaaagactggatcc
tgtggatttcctttgccatatcatgcttttttgctttgtgttgttttgct
ggggttcatcatgtgggcctgccagaaaggcaacattaggtg
caacatttgcatttga |
| SEQ ID NO.: 101 H5N1 | atggcgtctcaaggcaccaaacgatcttatgaacaaatggaaa
ctggtggagagcgccagaatgctactgagatcagggcatctg
ttggaagaatggttagtggcattgggaggttctacatacagatg
tgcacagaactcaaactcagtgactatgaaggagactgatc
cagaacagcataacaatagaaaggatggtactttctgcatttga
tgaaagaaggaacaggtacctggaagaacaccccagtgcgg
ggaaggacccgaagaaaactggaggcccaatttatcggagg
agagacggaaagtgggtgagggagctgattctgtacgacaa
agaggagatcaggaggatttggcgtcaagcgaacaatggag
aggacgcaactgctggtcttacccacctgatgatatggcattcc
aatctaaatgatgccacatatcagagaacgagagctctagtgc
gtactgggatggaccccaggatgtgctctctgatgcaagggt
caactctcccgaggagatctggagctgccggtgcagcagtga
aggggggtagggacaatggtgatggagctgattaggatgataa
aacgaggggtcaacgaccggaatttctggagaggcgaaaat
ggaagaagaactaggattgcatatgagagaatgtgcaacatc
ctcaaagggaaattccaaacagcagcacaaagagcaatgat
ggatcaagtgcgagagagcagaaatcctggaaatgctgaaat
tgaagatctcattttctggcacggtctgcactcatcctgagagg
atcagtggcccataagtcctgcttgcctgcttgtgtatacggact
tgcagtggccagtggatatgactttgagagagaagggtactct
ctggttggaatagatcctttccgtctgcttcaaaacagccaggt
ctttagtctcattaggccaaacgagaatccagcacataagagt
caattagtgtggatggcatgtcactctgcagcatttgaggacct
tagagtctcaagcttcatcagaggaacaagagtggtcccaag
aggacagctatccaccagaggggttcaaattgcttcaaatgag
aacatgaagtaatggactccaacactcttgaactgaggagta
gatattgggctataagaaccagaagcgggggaaacaccaac
cagcagaaggcatctgcagggcagatcagcgttcagcccac
tttctcggtacagagaaaccttcccttcgaaagagcgaccatta
tggcagcatttacaggaaatgctgagggcagaacgtctgaca
tgaggactgaaatcataagaatgatggaaagtgccagaccag
aagatgtgtcattccaggggcggggagtcttcgagctctcgg
acgaaaaggcaacgaacccgatcgtgccttcctttgacatgaa
taatgaaggatcttattcttcggagacaatgcagaggagtatg
acaattaa |
| SEQ ID NO.: 102 H7N9 | atgaacactcaaatcctggtattcgctctgattgcgatcattcca
acaaatgcagacaaaatctgcctcggacatcatgccgtgtcaa |

TABLE 2-continued

Viral gene sequences shown in FIGS. 3 and 15

| Viral genes | Corresponding sequence |
|---|---|
| | acggaaccaaagtaaacacattaactgaaagaggagtggaa |
| | gtcgtcaatgcaactgaaacagtggaacgaacaaacatcccc |
| | aggatctgctcaaaagggaaaaggacagttgacctcggtcaa |
| | tgtggactcctggggacaatcactggaccacctcaatgtgacc |
| | aattcctagaattttcagccgatttaattattgagaggcgagaag |
| | gaagtgatgtctgttatcctgggaaattcgtgaatgaagaagct |
| | ctgaggcaaattctcagagaatcaggcggaattgacaaggaa |
| | gcaatgggattcacatacagtggaataagaactaatggagca |
| | accagtgcatgtaggagatcaggatcttcattctatgcagaaat |
| | gaaatggctcctgtcaaacacagataatgctgcattcccgcag |
| | atgactaagtcatataaaaatacaagaaaaagcccagctctaa |
| | tagtatgggggatccatcattccgtatcaactgcagagcaaac |
| | caagctatatgggagtggaaacaaactggtgacagttgggag |
| | ttctaattatcaacaatcttttgtaccgagtccaggagcgagacc |
| | acaagttaatggtctatctggaagaattgactttcattggctaat |
| | gctaaatcccaatgatacagtcactttcagtttcaatgggctt |
| | catagctccagaccgtgcaagcttcctgagaggaaaatctatg |
| | ggaatccagagtggagtacaggttgatgccaattgtgaaggg |
| | gactgctatcatagtggagggacaataataagtaacttgccatt |
| | tcagaacatagatagcagggcagttggaaaatgtccgagatat |
| | gttaagcaaaggagtctgctgctagcaacagggatgaagaat |
| | gttcctgagattccaaagggaagaggcctatttggtgctatag |
| | cgggtttcattgaaaatggatgggaaggcctaattgatggttg |
| | gtatggtttcagacaccagaatgcacagggagagggaactgc |
| | tgcagattacaaaagcactcaatcggcaattgatcaaataaca |
| | ggaaaattaaaccggcttatagaaaaaaccaaccaacaatttg |
| | agttgatagacaatgaattcaatgaggtagagaagcaaatcgg |
| | taatgtgataaattggaccagagattctataacagaagtgtggt |
| | catacaatgctgaactcttggtagcaatggagaaccagcatac |
| | aattgatctggctgattcagaaatggacaaactgtacgaacga |
| | gtgaaaagacagctgagagagaatgctgaagaagatggcac |
| | tggttgctttgaaatatttcacaagtgtgatgatgactgtatggc |
| | cagtattagaaataacacctatgatcacagcaaatacagggaa |
| | gaggcaatgcaaaatagaatacagattgacccagtcaaacta |
| | agcagcggctacaaagatgtgatactttggtttagcttcgggg |
| | catcatgtttcatacttctagccattgtaatgggccttgtcttcata |
| | tgtgtaaagaatggaaacatgcggtgcactatttgtatataa |

3.2 Verification of Target Genes Using Luciferase Detection Method. The Specific Steps are as Follows:

(1) Constructing a 3'-UTR region such that a specific fragment of the predicted target gene sequence of MIR2911 can be inserted into the luciferase expression plasmid;

(2) Screening positive clones, sequencing, proliferating the positive clones, and purifying plasmid for use;

(3) Proliferating the plasmid carrying the predicted target gene, purifying same for use, meanwhile preparing corresponding empty plasmid control, and purifying same for use;

(4) Culturing related cells, inoculating same to 24-well plates, and allowing growth for 10-24 h;

(5) Co-transfecting cells with luciferase expression plasmid carrying the predicted target gene and MIR2911;

(6) Adding luciferase substrate, allowing luciferase to react with the substrate to produce fluorescein, and determining the activity of luciferase through detecting the intensity of fluorescence; and (7) Comparing with empty control (NC) to judge whether the predicted target can be inhibited by MIR2911 or not.

Figure 4:
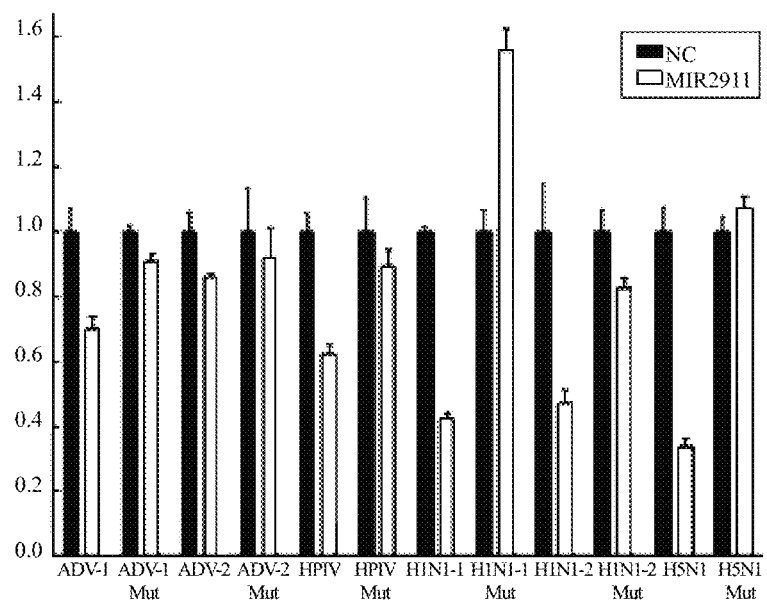
FIG. 4 shows the results of the detection of the predicted target genes by luciferase. The predicted genes include ADV gene, HPIV gene, H1N1 gene, and H5N1 gene.

The particular results are shown in FIG. 4. FIG. 4 is the results of the detection of the predicted target genes by luciferase. NC (i.e., equal quantity of RNAs containing the mismatching control sequences of MIR2911) is used as control. The results show that the majority of predicted target genes can bind to mature MIR2911 to form a double-stranded structure. This suggests that MIR2911 can exert the function of regulating the genes such as ADV gene, HPIV gene, H1N1 gene, H5N1 gene and the like through binding thereto.

3.3 Detection of Effects of MIR2911 on Viral Genes of ADV, H1N1, and H5N1 in Madin-Darby Canine Kidney (MDCK) Cells. The Specific Steps are as Follows:

(1) Culturing MDCK cells in 24-well cell culture plates.

(2) Transfecting MIR2911 (20 pmol/$10^6$ cells) into MDCK cells (MIR2911 group) through a commercial transfection reagent lipofectamine 2000, meanwhile transfecting the antisense sequence RNA of MIR2911 into MDCK cells in the same dose as control (NC), and setting positive drug control (Tamiflu).

(3) Using H1N1, H5N1 and adenovirus ADV to infect the above mentioned cells according to 0.001 of multiplicity of infection (MOI).

(4) Detecting the contents of viral genes of ADV, H1N1, and H5N1 in the cells through real-time PCR 24 hours after viral infection, and judging whether MIR2911 has effects of inhibiting the viral replication or not through comparing with the control group.

The specific steps for detecting the viral genes are: digesting and collecting cells, then repeatedly rinsing same with PBS buffer 3 times, extracting total RNA using a protein-denaturing reagent, then identifying the content of viral marker PB 1 mRNA therein through real-time PCR method, comparing with the standard curve, and calculating the content of viruses.

Figure 5A:
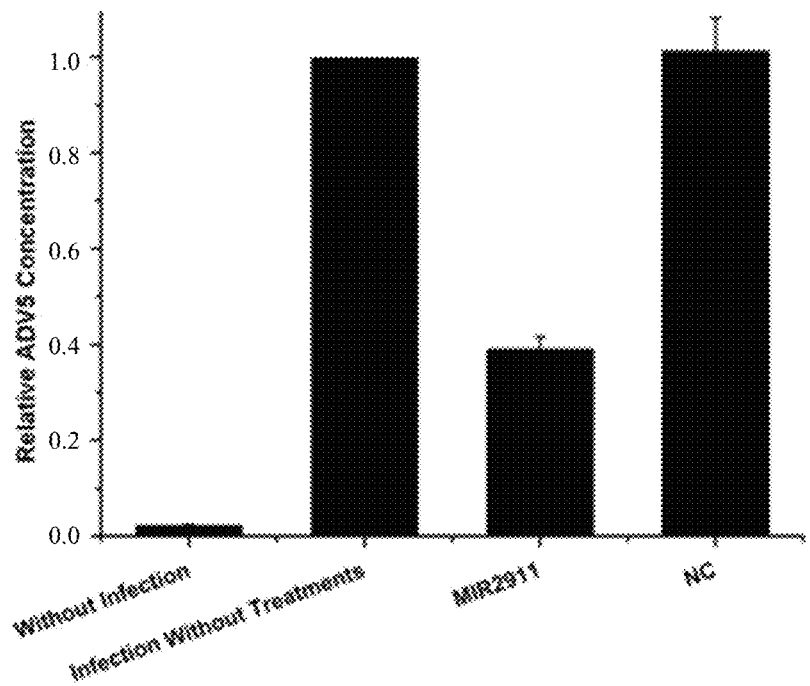
FIG. 5A is the content of viral gene of ADV5 in MDCK cells detected using real-time PCR technology.
Figure 5B:
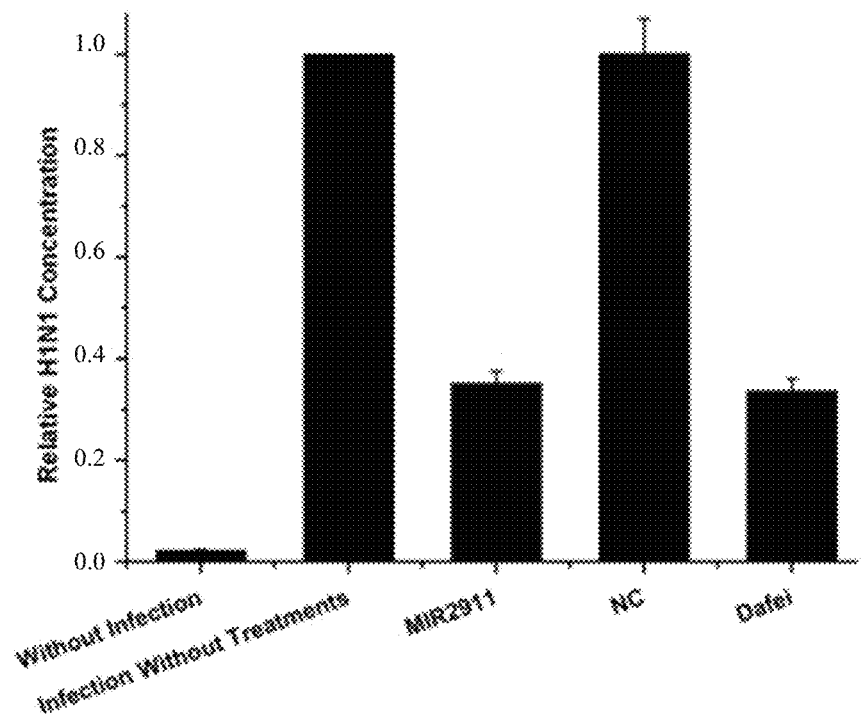
FIG. 5B is the content of viral gene of H1N1 in MDCK cells detected using real-time PCR technology.
Figure 5C:
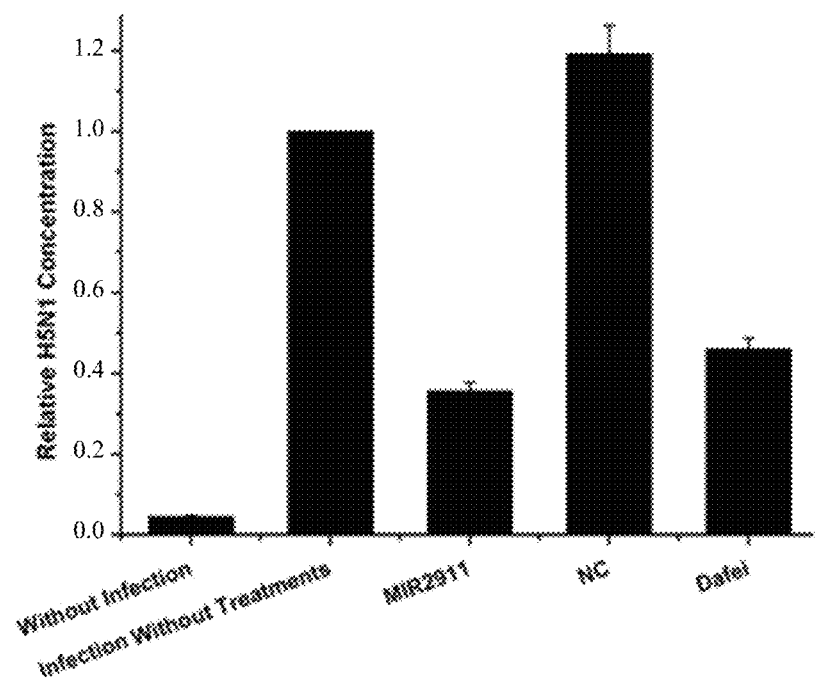
FIG. 5C is the content of viral gene of H5N1 in MDCK cells detected using real-time PCR technology.

The particular results are shown in FIG. 5A, FIG. 5B and FIG. 5C. FIG. 5A is the content of the viral gene of ADV in MDCK cells detected using real-time PCR technology. FIG. 5B is the content of the viral gene of H1N1 in MDCK cells detected using real-time PCR technology. FIG. 5C is the content of viral gene of H5N1 in MDCK cells detected using real-time PCR technology. The results show that MIR2911 has significant inhibiting and blocking effects on ADV5, H1N1 and H5N1.

Example 4 *Lonicera japonica* microRNA Enter Other Cells Through Caco-2 Cell Microvesicles (MVs) of Intestinal Epithelial Cells and Exert Regulating Effects in Other Cells This example demonstrates that *Lonicera japonica* microRNA can enter animal body through being enclosed by microvesicles of intestinal epithelial Caco-2 cells, and it can be delivered to and enter other cells via the cell microvesicles and exerts influences on the physiological and pathological conditions of other cells, such as inhibiting influenza virus.

4.1 Introduction of *Lonicera japonica* microRNAs into intestinal epithelial cells Caco-2, with the specific steps being:

(1) Inoculating intestinal epithelial cells Caco-2 to 12-well plates or petri dishes of 10 millimeters;
(2) Transfecting the cells with liposome 2000 on the next day;
(3) Transfecting Caco-2 cells with MIR2911;
(4) Culturing the cells for 24 or 48 hours after transfection for real-time PCR analysis.

4.2 Separating cell microvesicles released from the intestinal epithelial cells Caco-2 using differential centrifugation:

(1) Firstly centrifuging the cultured intestinal epithelial cells Caco-2 at 300 g for 5 minutes and collecting supernatant;
(2) Centrifuging the supernatant at 1200 g for 20 minutes and collecting the resulting supernatant;
(3) Centrifuging the above resulting supernatant at 10000 g for 30 minutes and collecting the resultant supernatant; and
(4) Centrifuging the above resultant supernatant at 110000 g for 2 hours, with all of the above operations being carried out at 4° C., and collecting the pellets in a FBS-free medium to obtain the total cell microvesicles.

4.3 Detection of the MIR2911 level in the cell microvesicles released from Caco-2 cells, It is demonstrated that MIR2911 has been enclosed by the cell microvesicles released from Caco-2 cells: RNA is extracted from the microvesicles and the content of MIR2911 therein is determined by absolute quantitative real-time PCR technology.

4.4 Cell microvesicles carrying MIR2911 are collected and applied to treat the HEK 293T cells, so as to demonstrated that *Lonicera japonica* microRNA is delivered into other cells via the cell microvesicles.

HEK 293T cells are treated with cell microvesicles carrying MIR2911, followed by detecting the expression level of MIR2911 in HEK 293T cells using real-time PCR experiment. The particular procedures for real-time PCR experiment are as described in example 2.

Figure 6:
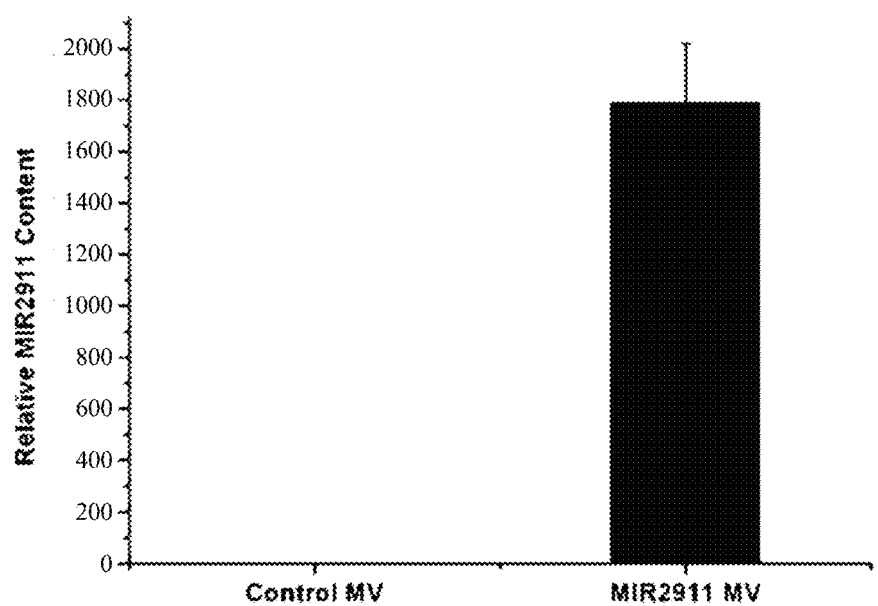
FIG. 6 shows the real-time PCR results of MIR2911 in cell microvesicles carrying MIR2911 secreted by the HEK 293T cells transfected with MIR2911. The cell microvesicles secreted by the HEK 293T cells not transfected with MIR2911 are used as control MV.

The particular results are shown in FIG. 6. FIG. 6 is the real-time PCR results of the cell microvesicles secreted by HEK 293T cells after being treated with the cell microvesicles carrying MIR2911 secreted by Caco-2 cells. The cell microvesicles secreted by HEK 293T cells having not been treated with the cell microvesicles carrying MIR2911 secreted by Caco-2 cells are used as control MV. It can be seen from the results that the expression of MIR2911 in HEK 293T cells after being treated with cell microvesicles carrying MIR2911 increases significantly as compared with control.

The results show that *Lonicera japonica* microRNAs can enter animal body through being enclosed by the cell microvesicles secreted by Caco-2 and can be delivered to other cells.

4.5 The effects of *Lonicera japonica* microRNA on the physiological/pathological states of cells after the microRNAs being delivered into other cells by cell microvesicles:

HEK 293T cells infected by influenza virus ADV or H1N1 are treated with cell microvesicles carrying MIR2911 (preparation method thereof being the same as the differential centrifugation method in section 4.2 of this example). The specific steps are as follows:

(1) Culturing HEK 293T cells in 24-well plates.
(2) Adding the microvesicles obtained in section 4.4 of this example to a cell culture medium, with dosage of microvesicles being 0.1 pmol MIR2911/$10^6$ cells.
(3) 6 hours after treatment in step (2), infecting adenovirus ADV or H1N1 influenza virus according to MOI=0.001.
(4) Detecting the content of viruses 24 hours after viral infection through real-time PCR. The content of influenza virus ADV or H1N1 in HEK 293T cells is detected using real-time PCR method. The particular procedures are as described in example 3.

Figure 7A:
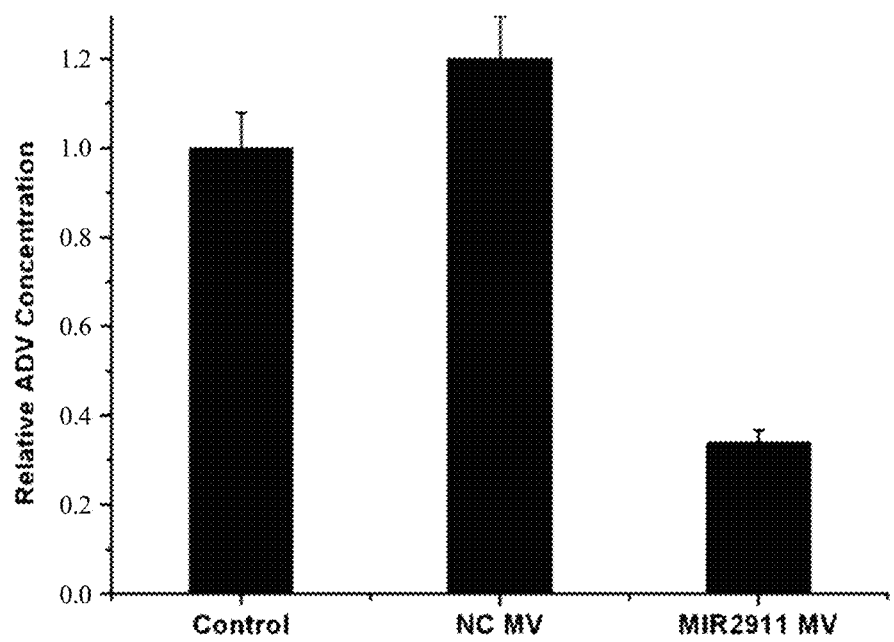
FIG. 7A is the expression amount of the influenza virus ADV in the HEK 293T cells treated with cell microvesicles carrying MIR2911.
Figure 7B:
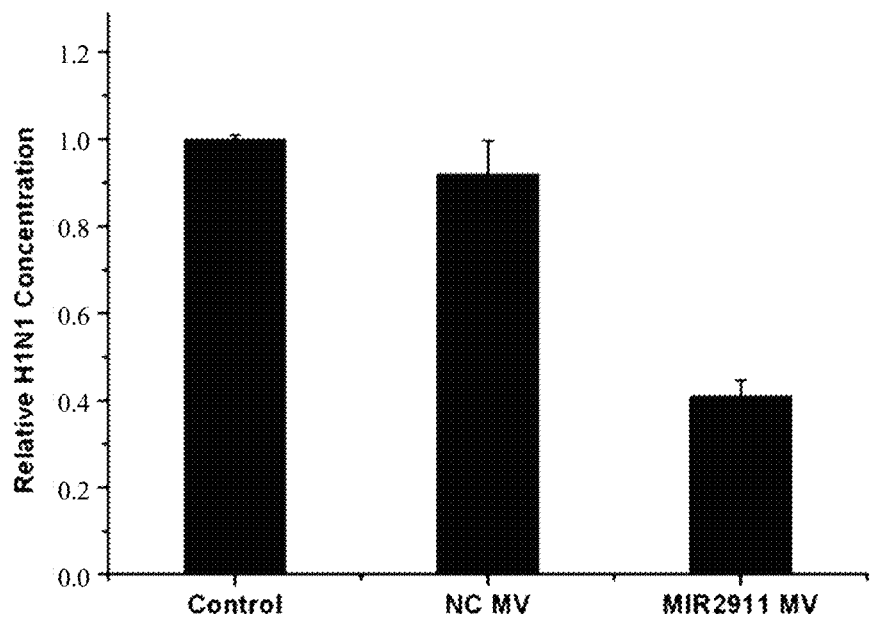
FIG. 7B is the expression amount of the influenza virus H1N1 in the HEK 293T cells treated with cell microvesicles carrying MIR2911.

The particular results are shown in FIG. 7. FIG. 7A is the expression amount of the influenza virus ADV in the HEK 293T cells treated with cell microvesicles carrying MIR2911. FIG. 7B is the expression amount of the influenza virus H1N1 in the HEK 293T cells treated with cell microvesicles carrying MIR2911. FIG. 7A and FIG. 7B employ the following cells as controls: after infected with influenza viruses, the non-treated HEK 293T cells (blank control) and the HEK 293T cells treated with cell microvesicles not carrying MIR2911 (negative control).

It can be seen from the results that the expressions of influenza virus ADV and H1N1 decrease significantly in HEK 293T cells treated with cell microvesicles carrying MIR2911. The results show that MIR2911 has significant inhibiting effects on influenza virus ADV and H1N1.

This example demonstrates that *Lonicera japonica* microRNAs can enter animal body through pathways such as oral intake, are enclosed by cell microvesicles and delivered into other cells, and exert functions in cells, such as inhibiting influenza virus. It can be seen therefrom that *Lonicera japonica* microRNAs can enter animal tissues and organs through pathways such as oral intake and regulate the physiological and pathological states of the animal.

Example 5 *Lonicera japonica* microRNAs can Inhibit Influenza Virus Significantly in Animal Body This example demonstrates that the effective ingredients which inhibit influenza virus are *Lonicera japonica* microRNAs rather than other ingredients.

The mice are allowed to randomly drink unconcentrated *Lonicera japonica* water extract (prepared in example 1) for 3 days, followed by inoculating ADV or H1N1 virus, continuing to drink unconcentrated *Lonicera japonica* water extract for 3 days, and detecting the content of viruses in lungs of the mice using real-time PCR. The results show that *Lonicera japonica* decoction has strong inhibiting effects on the proliferation of ADV and H1H1 viruses.

In order to verify it is just *Lonicera japonica* microRNA MIR2911 that exerts the virus-inhibiting effect, the following control groups are employed:

1. The mice are allowed to drink *Lonicera japonica* decoction containing anti-MIR2911 (usage amount thereof is equivalent to that of MIR2911), including drinking *Lonicera japonica* water extract+anti-MIR2911(oral group) and *Lonicera japonica* water extract+anti-MIR2911(lung lavage group); in which anti-MIR2911 is the antisense nucleic acid of MIR2911 and is completely complementary to MIR2911.

Mice are subjected to lung lavage, with the specific steps being:

(1) Narcotizing and fixing the mice and placing on a superclean bench;

(2) Dehairing on the neck and sterilizing;

(3) Exposing trachea under a sterile condition, and inserting a tracheal catheter and fixing same; and (4) Drawing *Lonicera japonica* water extract+anti-MIR2911 to perform lung lavage using a disposable syringe and repeatedly aspirating.

2. Mice drinking purified water with the same volume as that of *Lonicera japonica* decoction are used as blank control group. Afterwards, the contents of influenza viruses ADV or H1N1 in the lungs of each group of mice are detected using real-time PCR method.

The primer sequences for detecting the influenza virus ADV by real-time PCR are as follows:

```
Forward primer sequence:
                          (SEQ ID NO.: 89)
5'-CAAAGACTTCTCATCGGTTGC-3';

Reverse primer sequence:
                          (SEQ ID NO.: 90)
5'-AATGCAACACTCGGTTCACA-3';

Probe sequence:
                          (SEQ ID NO.: 91)
TCAGGC CCC CTCAAAGCCGA.
```

The primer sequences for detecting the influenza virus H1N1 by real-time PCR are as follows:

```
Forward primer sequence:
                          (SEQ ID NO.: 92)
5'-CCCAAAGTGAGGGATCAAGA-3';

Reverse primer sequence:
                          (SEQ ID NO.: 93)
5'-CCCTTGGGTGTCTGACAAGT-3';

Probe sequence:
                          (SEQ ID NO.: 94)
TCAACAGTGGCGAGTTCCCTAGCA.
```

Figure 8A:
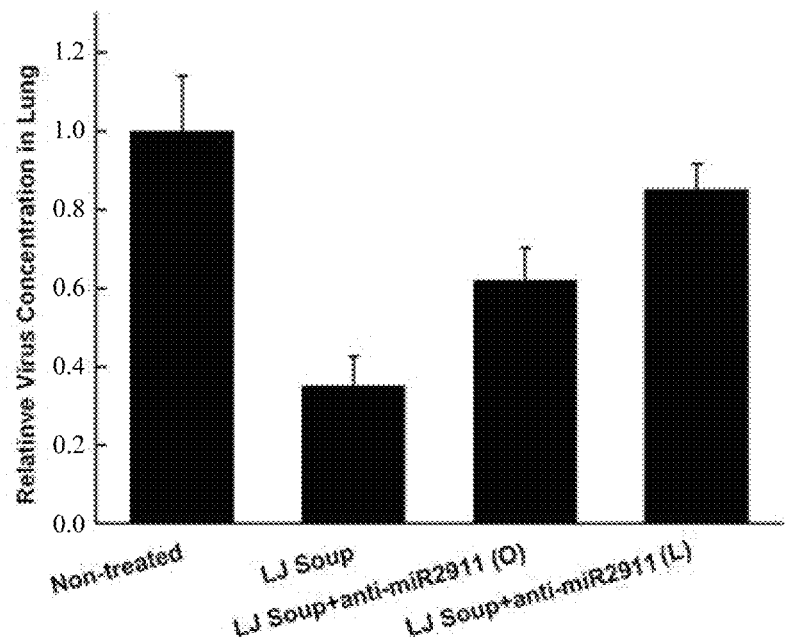
FIG. 8A shows the real-time PCR results of influenza virus ADV expressed in the lungs of mice after drinking *Lonicera japonica* water extract, *Lonicera japonica* water extract+anti-MIR2911 (oral group), and lung lavage with *Lonicera japonica* water extract+anti-MIR2911 (lung lavage group).
Figure 8B:
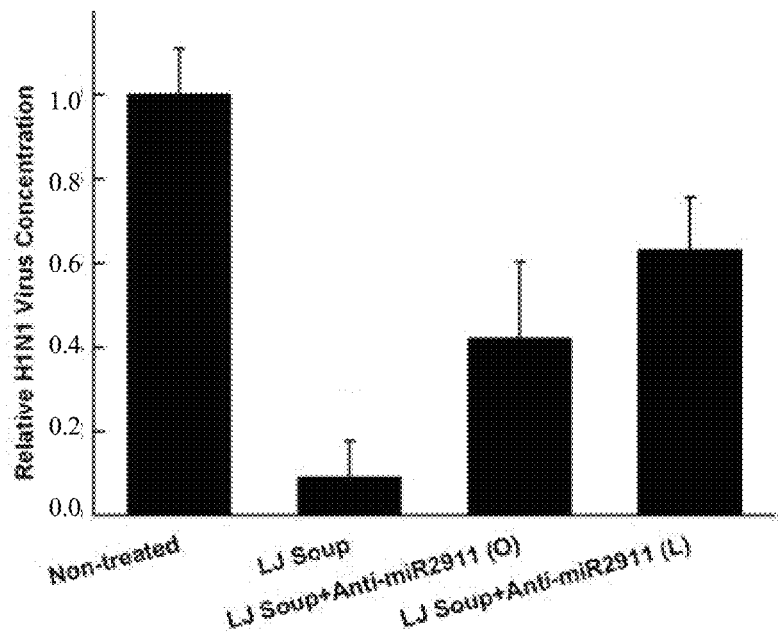
FIG. 8B shows the real-time PCR results of influenza virus H1N1 expressed in the lungs of mice after drinking *Lonicera japonica* water extract, *Lonicera japonica* water extract+anti-MIR2911 (oral group), and lung lavage with *Lonicera japonica* water extract+anti-MIR2911 (lung lavage group).

The particular results are shown in FIG. 8A and FIG. 8B.

FIG. 8A is the real-time PCR results of influenza virus ADV expressed in the lungs of mice after drinking *Lonicera japonica* water extract, *Lonicera japonica* water extract+anti-MIR2911 (oral group), and lung lavage with *Lonicera japonica* water extract+anti-MIR2911 (lung lavage group).

It can be seen from the results that the expression of ADV in the lungs of mice decreases significantly after drinking *Lonicera japonica* water extract as compared with the mice fed with the same volume of water as blank control, which indicates that *Lonicera japonica* microRNAs inhibit the expression of influenza virus ADV. As compared with drinking *Lonicera japonica* water extract, the expression of ADV in the lungs of mice increases after drinking *Lonicera japonica* water extract+anti-MIR2911, which demonstrates that anti-MIR2911 destructs the inhibiting effects of MIR2911 on influenza virus ADV. The results show that *Lonicera japonica* microRNAs have a direct antiviral effect.

FIG. 8B is the real-time PCR results of influenza virus H1N1 expressed in the lungs of mice after drinking *Lonicera japonica* water extract, *Lonicera japonica* water extract+anti-MIR2911 (oral group), and lung lavage with *Lonicera japonica* water extract+anti-MIR2911 (lung lavage group).

It can be seen from the results that the expression of H1N1 in the lungs of mice decreases significantly after drinking *Lonicera japonica* water extract as compared with the mice drinking purified water as blank control group, which indicates that *Lonicera japonica* microRNAs inhibit the expression of influenza virus H1N1. However, the expression of H1N1 in the lungs of mice increases after drinking *Lonicera japonica* water extract+anti-MIR2911. The results showed that *Lonicera japonica* microRNAs have a direct antiviral effect, as the anti-MIR2911 destructs MIR2911.

Example 6 *Lonicera japonica* microRNAs Enter Human Body Via Digestive Tract

This example demonstrates that *Lonicera japonica* microRNAs are absorbed in human body via the digestive tract and enter the circulatory system.

First of all, dry *Lonicera japonica* is decocted in water for 30 min to give 1000 ml of water extract, with content of MIR2911 in the water extract being about 0.4 n mol/L. Afterwards, 20 healthy volunteers are recruited, each orally takes the prepared water extract 1000 ml, blood of the volunteers are collected at 0 h (0 hour), 1 h (1 hour), 2 h (2 hour), 3 h (3 hour), 4 h (4 hour), 5 h (5 hour), and 6 h (6 hour), and the contents of MIR2911 therein are detected using real-time PCR, the specific steps of the real-time PCR experiment are as described in example 2.

Figure 9:
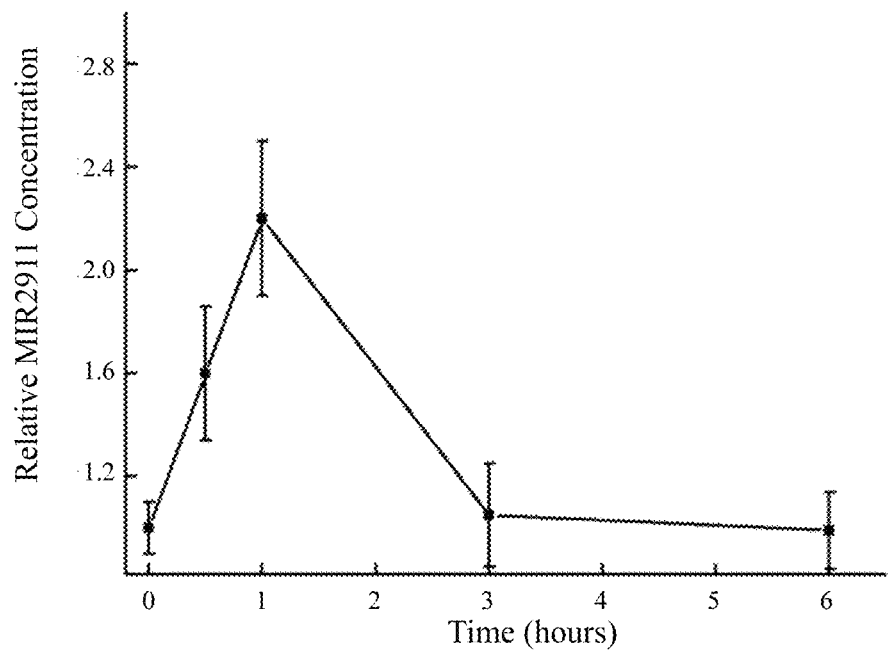
FIG. 9 shows the real-time PCR results of MIR2911 in human blood after oral intake of *Lonicera japonica* water extract.

The particular results are shown in FIG. 9. FIG. 9 is the real-time PCR results of MIR2911 in human blood after *Lonicera japonica* water extract is orally taken. It can be seen from the results that the content of MIR2911 in human blood increases significantly after *Lonicera japonica* water extract is orally taken. The content of MIR2911 in human blood reaches the maximum value 1.5 hours after *Lonicera japonica* water extract is orally taken, and decreases to the original level after 3 hours. These results are consistent with the experimental results on mice in example 2 (FIG. 2A). The results show that *Lonicera japonica* microRNAs can enter human body via ingestion, be absorbed in human body and enter the circulatory system.

Example 7 *Lonicera japonica* microRNAs can Significantly Inhibit Influenza Virus in Human Body This example demonstrates that the effective ingredients which inhibit influenza virus in human body are *Lonicera japonica* microRNAs rather than other ingredients.

Firstly, 15 viral cold patients carrying ADV viruses and 15 viral cold patients carrying H1N1 viruses are recruited, the above-mentioned viral cold patients are divided into 6 groups with each group 5 persons, in which groups 1-3 are viral cold patients carrying ADV viruses, and groups 4-6 are viral cold patients carrying H1N1 viruses:

Group 1: orally taking *Lonicera japonica* water extract (prepared in example 6) 1000 mL Group 2: orally taking *Lonicera japonica* water extract 1000 mL+anti-MIR2911(usage amount thereof is equivalent to the usage amount of MIR2911); in which anti-MIR2911 is the antisense nucleic acid of MIR2911, which is completely complementary to MIR2911 and can specifically degrade MIR2911.

Group 3: orally taking purified water of the same volume as that of the water extract.

Group 4: orally taking *Lonicera japonica* water extract (prepared in example 6) 1000 mL Group 5: orally taking *Lonicera japonica* water extract 1000 mL+anti-MIR2911(usage amount thereof is equivalent to the usage amount of MIR2911); in which anti-MIR2911 is the antisense nucleic acid of MIR2911, which is completely complementary to MIR2911 and can specifically degrade MIR2911.

Group 6: orally taking purified water of the same volume as that of the water extract.

6 days after oral administration, the contents of influenza viruses ADV or H1N1 in human blood are detected using real-time PCR. The particular procedures are as described in example 5.

The results show that:

1. With the cold patients orally taking water (group 3 and group 6) as controls, the expression of ADV or H1N1 in human blood decreases significantly after *Lonicera japonica* water extract is orally taken, which indicates that *Lonicera japonica* microRNAs inhibit the expression of influenza virus ADV or H1N1.

2. With the cold patients orally taking *Lonicera japonica* water extract (group 1 and group 4) as controls, the expression of ADV or H1N1 in human blood increases after the cold patients orally taking *Lonicera japonica* water extract+anti-MIR2911. It can be seen therefrom that anti-MIR2911 destructs the inhibiting effect of MIR2911 on influenza virus ADV or H1N1. The results showed that *Lonicera japonica* microRNAs have a direct antiviral effect.

Example 8 Stability Research on MIR2911 and the Absorption and Distribution of MIR2911 in Human and Mice 8.1 Types of Plant miRNAs Existing in Fresh *Lonicera japonica* and *Lonicera japonica* Water Extract Experimental Method:

First of all, *Lonicera japonica* microRNAs are extracted using a water extraction method. Appropriate amount (100 grams) of fresh medicinal material of *Lonicera japonica* is taken, followed by heating same in 100° C. water bath with the water being 1000 ml (the ratio of the mass of *Lonicera japonica* to the volume of water is 1:10) for 0.5 hours, and concentrating the water extract at 60° C. under reduced pressure to 1/10 of its original volume. The water extract is collected for subsequent experiments.

Appropriate amount (1 gram) of fresh *Lonicera japonica* is taken, followed by grinding same under liquid nitrogen condition and extracting total RNA using Trizol method for subsequent experiments.

Afterwards, the plant microRNAs stably existing in the fresh *Lonicera japonica* and *Lonicera japonica* water extract prepared via the above-mentioned steps are detected using Solexa sequencing technology, the loading amount for Solexa sequencing is 10 μg RNA.

Experimental Results:

a. Solexa Sequencing Results of the Plant miRNAs in Fresh *Lonicera japonica*;

A variety of plant microRNAs exist stably in fresh *Lonicera japonica*, in which MIR167a, MIR166f, MIR166b, MIR164a, MIR168a, MIR156h, MIR172a, MIR162b, MIR159d, MIR827b, MIR396b, MIR2911, and MIR2916 have relatively high contents. They are shown in FIG. 10.

b. Solexa Sequencing Results of the Plant miRNAs in *Lonicera japonica* Water Extract;

A variety of plant microRNAs exist stably in *Lonicera japonica* water extract, including MIR167a, MIR166f, MIR166b, MIR164a, MIR168a, MIR156h, MIR172a, MIR162b, MIR159d, MIR827b, MIR396b, MIR2911, and MIR2916, in which MIR2911 is the highest in content. They are shown in FIG. 11.

8.2 Stability Analysis of Extracted or Synthesized MIR2911

Experimental Method:

*Lonicera japonica* microRNAs are extracted using a water extraction method. The particular experimental procedures are as described in example 8.1. MIR2911 is artificially synthesized according to a conventional method.

The concentration of MIR2911 in *Lonicera japonica* water extract or of synthesized MIR2911 is detected using real-time PCR method, with the particular experimental procedures being as described in example 2.

The concentrations of MIR2911 and MIR167 in sera and water are detected using real-time PCR method, with the particular experimental procedures being as described in example 2.

Experimental Results:

It can be seen from FIG. 12 that as compared with MIR2911 mutant (having one point mutation), either the MIR2911 extracted from *Lonicera japonica* or the synthesized MIR2911 does not degrade and has high stability. The concentration of the MIR2911 mutant falls quickly after just one hour, which indicates that the degradation speed thereof is relatively high. It can be seen therefrom that the MIR2911 extracted from *Lonicera japonica* or synthesized MIR2911 has a relatively high stability. This is a basis for them to play a role as a pharmaceutical.

It can be seen from FIG. 13 that as compared with MIR167, MIR2911 either synthesized or extracted from *Lonicera japonica* does not degrade in water and sera at various time points and has a high stability; in contrast, MIR167 degrades fast and its content decreases substantially after only one hour. It can be seen therefrom that MIR2911 is stable in water and sera.

8.3 Dynamic Research Results of MIR2911 in Mice Sera of Mice after Intragastrical Administration of the Synthesized MIR2911.

The content of MIR2911 in sera significantly increases after intragastrically administering 2 nmol synthesized MIR2911 to mice. It is shown as in FIG. 14A. The content of MIR2911 in sera reaches the maximum value 0.5 hours after intragastric administration, and the content of MIR2911 in sera decreases to the original level after 24 hours.

The results demonstrate that the synthesized MIR2911 can enter animal body and undergo normal metabolic pathway, which conforms to the rule of pharmacokinetics and can be used as a potential therapeutic drug.

8.4 Distribution of MIR2911 in Mice Organs after Intragastrical Administration of *Lonicera japonica* Water Extract.

The fluorescently labeled synthesized MIR2911 are specifically delivered to the lungs of the mice 3 hours after intragastrically administering *Lonicera japonica* water extract to the mice. As shown in FIG. 14B, labeled MIR2911 (in red) accumulates in the lungs of the mice rapidly. It is demonstrated that MIR2911, after entering blood, can reach the sites where require it to play a role, that is, it can smoothly reach a target organ and play a role.

Example 9 MIR2911 can Regulate Physiological and Pathological Activities

This example demonstrates that MIR2911 targets various influenza viruses and inhibits replication thereof in the cells infected by the viruses.

9.1 Sequence Analysis Results of the Predicted Viral Target Genes of MIR2911.

Viral genes of H1N1, H3N2, H5N1, and H7N9 are predicted to match with MIR2911 using bioinformatics. The particular results are shown in FIG. 15. FIG. 15 is the sequence analysis results of the predicted target genes of MIR2911. The results show that viral genes of H1N1, H3N2, H5N1, and H7N9 are potential target genes of *Lonicera japonica* microRNAs. The sequences of H1N1 genes, H3N2 gene, H5N1 gene, and H7N9 gen are shown in Table 2.

9.2 Verification of Predicted Viral Target Genomic Sequence of MIR2911 Using Luciferase Reporter Gene.

Experimental Method:

Verification of target genes using a luciferase detection method. The particular operating procedures are as described in example 3.2.

Experimental Results:

The results are shown in FIG. 16. It is verified and analyzed that H1N1, H3N2, H5N1, and H7N9 are potential target genes of *Lonicera japonica* MIR2911.

9.3 Plant MIR2911 can Bind to AGO2 Complex in MDCK Cells and AGO2 can Help Deliver MIR2911 into Cells.

Experimental method: the specific steps being as follows:

(1) Allowing MIR2911 to bind to AGO2 complex;

(2) Culturing MDCK cells in 24-well cell culture plates.

(3) Introducing MIR2911 and AGO2 complex into the above-mentioned cells.

(4) Detecting the expression level of MIR2911 in the cells after 24 hours through real-time PCR.

Experimental results: the results being as shown in FIG. 17. The research discovers that MIR2911 can bind to AGO2 complex and AGO2 can help deliver MIR2911 into cells.

9.4 Effects of MIR2911 on H1N1 Influenza Virus a Gene (Anti-H1N1) in MDCK Cells.

Experimental Method:

The particular operating procedures are as described in example 3.3, except for the difference that MIR2911 is transfected into MDCK cells together with AGO2 complex. The transfection times are 12 hours and 24 hours, respectively.

Experimental Results:

The results are shown in FIG. 18. The research discovers that MIR2911 has a significant inhibiting effect on H1N1 viruses over different action times (administration time of 12 hours or 24 hours).

9.5 Effects of MIR2911 on H5N1 Avian Influenza Virus Gene (Anti-H5N1) in MDCK Cells.

Experimental Method:

The particular operating procedures are as described in example 3.3, except for the difference that MIR2911 is transfected into MDCK cells together with AGO2 complex. The transfection times are 12 hours and 24 hours, respectively.

Experimental Results:

The results are shown in FIG. 19. The research discovers that MIR2911 has a significant inhibiting effect on H5N1 viruses over different action times (administration time of 12 hours or 24 hours).

9.6 Effects of MIR2911 on H7N9 Avian Influenza Virus Gene (Anti-H7N9) in MDCK Cells.

Experimental Method:

The particular operating procedures are as described in example 3.3, except for the difference that MIR2911 is transfected into MDCK cells together with AGO2 complex. The transfection times are 12 hours and 24 hours, respectively. Avian influenza virus gene of H7N9 is used to infect MDCK cells.

Experimental Results:

The results are shown in FIG. 20. The research discovers that MIR2911 has a significant inhibiting effect on H7N9 viruses over different action times (administration time of 12 hours or 24 hours).

Example 10 Inhibition of MIR2911 on Replication of IAVs (Influenza A Virus) in Mice Before inoculation, the mice are treated with three different subtypes of influenza viruses. 3, 5, and 7 days after virus infection, the changes of body weight are recorded daily. The mice are sacrificed and the quantity of viruses in lungs is measured.

10.1 H1N1 Virus

1. Research on effects of MIR2911 on the body weight of mice inoculated with H1N1 viruses The research discovers that the body weight of the mice inoculated with H1N1 viruses has no significant change after the mice drinking MIR2911-containing solution or *Lonicera japonica* decoction; and the body weight of the mice significantly decreases after the mice drinking the solution free of MIR2911. It can be seen therefrom that MIR2911 has a significant inhibiting effect on H1N1 viruses, maintains the body weight balance of mice, and improves the physiological state of mice.

2. Changes of virus titer $EID_{50}$ in lungs of mice infected by H1N1 viruses after infection is confirmed at different time points Experimental Method:

The specific operating steps are as follows:

(1) Allowing viruses to be subjected to 10-fold serial dilution and inoculating mice of 1 week-old respectively;

(2) Inoculating one group of 6 mice with each dilution and cultivating the mice at 37° C.-38° C.;

(3) Sacrificing the mice 3, 5, and 7 days after infection respectively and taking blood from lungs to carry out hemagglutination test; and (4) Detecting hemagglutination activity and calculating $EID_{50}$ of lungs using Reed-Muench method.

Experimental results are as shown in FIG. 21 and FIG. 22:

H1N1 represents viral infection group administered H1N1 directly;

H1N1+NC represents H1N1 virus infection with negative control (antisense sequence) administrated;

H1N1+MIR2911 represents H1N1 virus infection with direct administration of MIR2911).

FIG. 21 shows that there is no significant difference between the two control groups (H1N1, H1N1+NC) 3 days after infection, which demonstrates that the antisense sequence has no viricidal effect; the virus content in lungs in drug administration group (H1N1+MIR2911) decreases greatly with a significant difference compared with the control group (H1N1+NC), which demonstrates that the drug has extremely obvious effect of killing viruses in lungs.

FIG. 22 shows that 3 days and 5 days after infection, the virus content in lungs in the experimental group (mice infected by H1N1 and administered with *Lonicera japonica* decoction+anti-MIR2911, H1N1+LJ soup+MIR2911) is greatly higher than that of the control group (mice infected by H1N1 and administered with *Lonicera japonica* decoction, H1N1+LJ soup), with difference being significant between the two groups. The result demonstrates that after the anti-MIR2911 degrades MIR2911 in the *Lonicera japonica* decoction, the *Lonicera japonica* decoction loses its antiviral effect, which demonstrates that it is MIR2911 that plays the role.

10.2 H5N1 Virus

1. Research on effects of MIR2911 on the body weight of mice inoculated with H5N1 viruses The research discovers that the body weight of the mice inoculated with H5N1 viruses has no significant change after the mice drinking MIR2911-containing solution or *Lonicera japonica* decoction; and the body weight of the mice significantly decreases after the mice drinking the solution free of MIR2911. It can be seen therefrom that MIR2911 has a significant inhibiting effect on H5N1 viruses, maintains the body weight balance of mice, and improves the in vivo physiological state of mice.

2. Changes of virus titer $EID_{50}$ in lungs of mice infected by H5N1 viruses after infection is confirmed at different time points The particular operating procedures are as described in example 10.1. The experimental results show that the drug has a killing effect on the viruses in lungs.

10.3 H7N9 Virus

1. Research on effects of MIR2911 on the body weight of mice inoculated with H7N9 viruses The research discovers that the body weight of the mice inoculated with H7N9 viruses has no significant change after the mice drinking MIR2911-containing solution or *Lonicera japonica* decoction; and the body weight of the mice significantly decreases in the experimental group in which the mice drink the solution free of MIR2911. It can be seen therefrom that MIR2911 has a significant inhibiting effect on H7N9 viruses, maintains the body weight balance of mice, and improves the in vivo physiological state of mice.

2. Changes of virus titer $EID_{50}$ in lungs of mice infected by H7N9 viruses after infection is confirmed at different time points.

The particular operating procedures are as described in example 10.1.

Experimental results are as shown in FIG. 23 and FIG. 24.

H7N9 represents viral infection group administered H7N9 directly;

H7N9+NC represents H7N9 virus infection with negative control (antisense sequence) administrated;

H7N9+MIR2911 represents H7N9 virus infection with direct administration of MIR2911).

FIG. 23 shows that there is no significant difference between the two control groups (H7N9, H7N9+NC) after infection, which demonstrates that the antisense sequence has no viricidal effect; the virus content in lungs in drug administration group (H7N9+MIR2911) decreases greatly with a significant difference compared with the control group (H7N9+NC), which demonstrates that the drug has extremely obvious effect of killing viruses in lungs.

FIG. 24 shows that after infection, the virus content in lungs in the experimental group (mice infected by H7N9 and administered with *Lonicera japonica* decoction+anti-MIR2911, H7N9+LJ soup+MIR2911) is greatly higher than that of the control group (mice infected by H7N9 and administered with *Lonicera japonica* decoction, H7N9+LJ soup), with difference being significant between the two groups. The result demonstrates that after the anti-MIR2911 degrades MIR2911 in the *Lonicera japonica* decoction, the *Lonicera japonica* decoction loses its antiviral effect, which demonstrates that it is MIR2911 that plays a role.

Example 11 Content Comparison of MIR2911 in Fresh *Lonicera japonica*, Dry *Lonicera japonica*, and Mouse Feed Detection Method:

The contents of MIR2911 in fresh *Lonicera japonica*, dry *Lonicera japonica*, and mouse feed are detected using real-time PCR method, with the particular experimental procedures being as described in example 2.

Experimental Results:

The results are shown in FIG. 25, and it can be seen in above-mentioned experiments that the mouse feed is substantially free of MIR2911 and has no influence on the experimental results.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A method for preparing a pharmaceutical comprising:
extracting MIR2911 from a plant using water to obtain an extract containing MIR2911; and
mixing the extract containing MIR2911 with a carrier acceptable in pharmaceutics to form said pharmaceutical,
wherein the extract containing MIR2911 is a water extract of *Lonicera japonica*
and contains 0.01-100 nM MIR2911, and
the extract containing MIR2911 has a MIR2911 content that is greater than or equal to 70% of a total amount of microRNAs in the extract containing MIR2911.

2. The method of claim 1, wherein said extract containing MIR2911 contains 0.1-20 nM MIR2911.

3. The method of claim 1, wherein the extract containing MIR2911 is an aged extract obtained from an aging treatment.

4. The method of claim 3, wherein the aging treatment is a placement.

5. The method of claim 3, wherein the aging treatment is a placement at 20° C.-50° C. for 2 hours to 10 days.

6. A method for treating a viral cold comprises administering a microRNA molecule MIR2911 at a concentration of 0.01-100 nM to a subject in need thereof.

7. A method for treating a viral cold comprises administering a pharmaceutical comprising an extract containing MIR2911 and a carrier acceptable in pharmaceutics to a subject in need thereof,
wherein the extract containing MIR2911 is an extract of *Lonicera japonica*,
the extract containing MIR2911 is a water-soluble extract of plants, and
the extract containing MIR2911 contains 0.01-100 nM MIR2911.

8. The method of claim 7, wherein the extract containing MIR2911 is an aged extract obtained by aging treatment.

9. The method of claim 8, wherein the aging treatment is a placement.

10. The method of claim 8, wherein the aging treatment is a placement at 20° C.-50° C. for 2 hours to 10 days.

11. The method of claim 1, wherein the carrier is one or more of cellulose or a derivative thereof, gelatin, talc, solid lubricant, calcium sulfate, vegetable oil, polyol, an emulsifying agent, a wetting agent, a colorant, a flavoring agent, a stabilizing agent, an antioxidant, and a preservative.

* * * * *